US011614437B2

(12) United States Patent
Hickman et al.

(10) Patent No.: US 11,614,437 B2
(45) Date of Patent: Mar. 28, 2023

(54) DEVICES, SYSTEMS, AND METHODS FOR EVALUATING CARDIAC PARAMETERS

(71) Applicant: UNIVERSITY OF CENTRAL FLORIDA RESEARCH FOUNDATION, INC., Orlando, FL (US)

(72) Inventors: James Hickman, Orlando, FL (US); Maria Stancescu, Orlando, FL (US); Peter Molnar, Orlando, FL (US); Christopher Long, Orlando, FL (US); Christopher McAleer, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 184 days.

(21) Appl. No.: 16/913,528

(22) Filed: Jun. 26, 2020

(65) Prior Publication Data
US 2020/0400647 A1 Dec. 24, 2020

Related U.S. Application Data

(63) Continuation of application No. 14/764,683, filed as application No. PCT/US2014/013903 on Jan. 30, 2014, now abandoned.

(60) Provisional application No. 61/790,061, filed on Mar. 15, 2013, provisional application No. 61/758,628, filed on Jan. 30, 2013.

(51) Int. Cl.
G01N 33/483 (2006.01)
C12M 3/00 (2006.01)
C12M 1/36 (2006.01)

(52) U.S. Cl.
CPC ......... G01N 33/4836 (2013.01); C12M 21/08 (2013.01); C12M 41/48 (2013.01)

(58) Field of Classification Search
CPC .... G01N 33/4836; C12M 41/48; C12M 21/08
See application file for complete search history.

(56) References Cited

U.S. PATENT DOCUMENTS

| | | |
|---|---|---|
| 5,442,510 A | 8/1995 | Schwartz et al. |
| 5,682,899 A | 11/1997 | Nashef et al. |
| 5,948,621 A | 9/1999 | Turner et al. |
| 6,866,383 B2 | 3/2005 | Naik et al. |
| 6,916,541 B2 | 7/2005 | Pantano et al. |
| 6,935,165 B2 | 8/2005 | Bashir et al. |
| 7,384,786 B2 | 6/2008 | Freyman et al. |
| 7,541,146 B2 | 6/2009 | Lewis |
| 7,579,189 B2 | 8/2009 | Freyman et al. |
| 7,691,629 B2 | 4/2010 | Johe et al. |
| 7,860,563 B2 | 12/2010 | Foreman et al. |
| 7,923,015 B2 | 4/2011 | V-Martinez et al. |
| 7,927,671 B2 | 4/2011 | Kato |
| 8,071,319 B2 | 12/2011 | Metzger et al. |
| 8,178,602 B2 | 5/2012 | Mao et al. |
| 8,318,488 B1 | 11/2012 | Bohlen |
| 8,318,489 B2 | 11/2012 | Davidson et al. |
| 8,318,951 B2 | 11/2012 | Olson et al. |
| 8,828,721 B1 | 9/2014 | Hickman et al. |
| 9,404,140 B1 | 8/2016 | Molnar et al. |
| 2003/0054355 A1 | 3/2003 | Warthoe |
| 2003/0065452 A1 | 4/2003 | Hickman |
| 2003/0144823 A1 | 7/2003 | Fox et al. |
| 2003/0211542 A1 | 11/2003 | Lee et al. |
| 2005/0074834 A1 | 4/2005 | Chaplen et al. |
| 2006/0058607 A1 | 3/2006 | Garcia-Webb et al. |
| 2006/0105457 A1 | 5/2006 | Rameshwar |
| 2006/0259992 A1 | 11/2006 | Koren et al. |
| 2007/0015138 A1 | 1/2007 | Barlow et al. |
| 2007/0037225 A1 | 2/2007 | Metzger et al. |
| 2007/0089515 A1 | 4/2007 | Shih et al. |
| 2007/0117217 A1 | 5/2007 | Lal et al. |
| 2007/0122896 A1 | 5/2007 | Shuler et al. |
| 2007/0129447 A1 | 6/2007 | Sra |
| 2007/0212723 A1 | 9/2007 | Dudley et al. |
| 2007/0218534 A1 | 9/2007 | Klenerman et al. |
| 2008/0124789 A1 | 5/2008 | Hickman |
| 2008/0138797 A1 | 6/2008 | Hunt et al. |
| 2008/0166795 A1 | 7/2008 | Shuler et al. |
| 2008/0227137 A1 | 9/2008 | Zhang et al. |
| 2009/0029463 A1 | 1/2009 | Collins |
| 2009/0078023 A1 | 3/2009 | Mutharasan et al. |

(Continued)

FOREIGN PATENT DOCUMENTS

| | | |
|---|---|---|
| CA | 2788905 | 8/2011 |
| CA | 2798777 | 10/2011 |

(Continued)

OTHER PUBLICATIONS

Examination Search Report dated Nov. 2, 2021, issued in Canadian Application No. 2,899,445 (3 pages).
Abbanat D, et al. (2003) Novel antibacterial agents for the treatment of serious Gram-positive infections. Expert Opin Investig Drugs. 12: 379-399.
Abdi H. (2003) Multivariate Analysis. Encyclopedia of Social Sciences Research Methods. M. Lewis-Beck, A. Bryman and T. Futing. Thousand Oaks (CA), Sage.
Adell A, et al. (2002) Origin and functional role of the extracellular serotonin in the midbrain raphe nuclei. Brain Res Brain Res Rev. 39: 154-180.
Agarwal A, et al. (2013) Microfluidic heart on a chip for higher throughput pharmacological studies. Lab Chip. 13: 3599-3608.
Ahern CA, et al. (2003) Ca2+ current and charge movements in skeletal myotubes promoted by the beta-subunit of the dihydropyridine receptor in the absence of ryanodine receptor type 1. Biophys J. 84: 942-959.

(Continued)

Primary Examiner — Nghi V Nguyen
(74) Attorney, Agent, or Firm — Meunier Carlin & Curfman LLC

(57) ABSTRACT

In an aspect, disclosed herein are physiological devices and systems, and components thereof, used to evaluate cardiac parameters and arrhythmogenic mechanisms. This abstract is intended as a scanning tool for purposes of searching in the particular art and is not intended to be limiting of the present invention.

17 Claims, 32 Drawing Sheets

(56) References Cited

U.S. PATENT DOCUMENTS

| | | |
|---|---|---|
| 2009/0226768 A1 | 9/2009 | Wang et al. |
| 2009/0227469 A1 | 9/2009 | Conklin et al. |
| 2009/0239940 A1 | 9/2009 | Del Monte et al. |
| 2009/0305319 A1 | 12/2009 | Baudenbacher |
| 2010/0028902 A1 | 2/2010 | Brown et al. |
| 2012/0135452 A1 | 5/2012 | Shuler et al. |
| 2012/0142556 A1 | 6/2012 | Parker et al. |
| 2014/0220555 A1* | 8/2014 | Chen ............... C12N 1/20 435/235.1 |
| 2014/0274796 A1 | 9/2014 | Hickman |
| 2015/0219622 A1 | 8/2015 | Hickman |
| 2015/0369791 A1 | 12/2015 | Hickman et al. |
| 2016/0041150 A1 | 2/2016 | Hickman et al. |
| 2016/0305927 A1 | 10/2016 | Molnar et al. |
| 2018/0095073 A1 | 4/2018 | Hickman |

FOREIGN PATENT DOCUMENTS

| | | |
|---|---|---|
| EP | 2434896 | 4/2012 |
| EP | 2435585 | 4/2012 |
| EP | 2531910 | 12/2012 |
| EP | 2585171 | 5/2013 |
| EP | 2951281 B1 | 12/2015 |
| WO | 2001/029206 | 4/2001 |
| WO | 2005/033264 | 4/2005 |
| WO | 2005/108598 | 11/2005 |
| WO | 2009/036573 | 3/2009 |
| WO | 2010/127280 | 11/2010 |
| WO | 2010/138679 | 12/2010 |
| WO | 2010/138782 | 12/2010 |
| WO | 2011/097574 | 8/2011 |
| WO | 2011/133985 | 10/2011 |
| WO | 2012/158923 | 11/2012 |
| WO | 2013/013206 | 1/2013 |
| WO | 2014/028940 | 2/2014 |
| WO | 2014120952 A1 | 8/2014 |

OTHER PUBLICATIONS

Ahmari SE, et al. (2000) Assembly of presynaptic active zones from cytoplasmic transport packets. Nat Neurosci. 3: 445-451.

Ahuja TK, et al. (2007) Hippocampal slice cultures integrated with multi-electrode arrays: A model for study oflong-term drug effects on synaptic activity. Drug Development Research. 68: 84-93.

Ainscow EK and Brand MD. (1999) Internal regulation of ATP turnover, glycolysis and oxidative phosphorylation in rat hepatocytes. Eur J Biochem. 266:737-749.

Akaaboune M, et al. (2000) Developmental regulation of amyloid precursor protein at the neuromuscular junction in mouse skeletal muscle. Mol Cell Neurosci. 15: 355-367.

Akanda N, et al. (2008) Effect of malonate, a metabolic pathway inhibitor, on action potential peak shape and the relationship to cellular pathways. 38th Annual Meeting of the Society for Neuroscience. vol 38.

Akanda N, et al. (2009) Analysis of toxin-induced changes in action potential shape for drug development. J Biomol Screen. 14: 1228-1235.

Alabed YZ, et al. (2006) Neuronal responses to myelin are mediated by rho kinase. J Neurochem. 96: 1616-1625.

Albensi BC. (2003) A comparison of drug treatment versus electrical stimulation for suppressing seizure activity. Drug News Perspect. 16: 347-352.

Albert R and Othmer H. (2003) The topology of the regulatory interactions predicts the expression pattern of the segment polarity genes in *Drosophila melanogaster*. J Theor Biol. 223: 1-18.

Albert Y, et al. (2005) Transcriptional regulation of myotube fate specification and intrafusal muscle fiber morphogenesis. J Cell Biol. 169: 257-268.

Alexander SL, et al. (1989) An atomic-resolution atomic-force microscope implemented using an optical lever. J Appl Phys. 65: 164-167.

Al-Shanti N, et al. (2008) Beneficial synergistic interactions of TNF-alpha and IL-6 in C2 skeletal myoblasts—potential cross-talk with IGF system. Growth Factors. 26: 61-73.

Alsina B, et al. (2001) Visualizing synapse formation in arborizing optic axons in vivo: dynamics and modulation by BDNF. Nat Neurosci. 4: 1093-1101.

Alterio J, et al. (1990) Acidic and basic fibroblast growth factor mRNAs are expressed by skeletal muscle satellite cells.Biochem Biophys Res Commun. 166:1205-1212.

Altmann L. (2000) Multielectrode recordings of synaptic plasticity in brain slices: A new method for the assessment of neurotoxic effects. European Journal of Neuroscience. 12: 29-29.

Amarenco P, et al. (2006) High-dose atorvastatin after stroke or transient ischemic attack. N Engl J Med. 355: 549-559.

Amit M. (2007) Feeder-layer free culture system for human embryonic stem cells. Methods Mol Biol. 407: 11-20.

Anderson DJ, et al. (1997) Cell lineage determination and the control of neuronal identity in the neural crest. Cold Spring Harb Symp Quant Biol. 62: 493-504.

Anderson JE, et al. (1991) Distinctive patterns of basic fibroblast growth factor (bFGF) distribution in degenerating and regenerating areas of dystrophic (mdx) striated muscles. Dev Biol. 147: 96-109.

Andersson Hand van den Berg A. (2004) Microfabrication and microfluidics for tissue engineering: state of the art and future opportunities. Lab Chip. 4: 98-103.

Antzelevitch C. (2001) Transmural dispersion of repolarization and the T wave. Cardiovasc Res. 50: 426-431.

Antzelevitch C. (2005) Cardiac repolarization. The long and short of it. Europace. 7: 3-9.

Aracil A, et al. (2004) Proceedings of Neuropeptides 2004, the XIV European Neuropeptides Club meeting. Neuropeptides. 38: 369-371.

Archer JD, et al. (2006) Persistent and improved functional gain in mdx dystrophic mice after treatment with L-arginine and deflazacort. F ASEB J. 20:738-740.

Armstrong DL and Rossie S. (1999) Ion channel regulation. Introduction. Adv Second Messenger Phosphoprotein Res. 33: ix-xx.

Arnold HH and Winter B. (1998) Muscle differentiation: more complexity to the network of myogenic regulators. Curr Opin Genet Dev. 8: 539-544.

Arnone MI and Davidson EH. (1997) The hardwiring of development: organization and function of genomic regulatory systems. Development. I24:I85I-I864.

Arsic N, et al. (2004) Vascular endothelial growth factor stimulates skeletal muscle regeneration in vivo. Mol Ther. 10: 844-854.

Askanas V, et al. (I987) De novo neuromuscular junction formation on human muscle fibres cultured in monolayer and innervated by foetal rat spinal cord: ultrastructural and ultrastructural—cytochemical studies. J Neurocytol. I6: 523-537.

Asotra K and Macklin WB. (I993) Protein kinase C activity modulates myelin gene expression in enriched oligodendrocytes. J Neurosci Res. 34: 57I-588.

Azzouz M, et al. (2004) VEGF delivery with retrogradely transported lentivector prolongs survival in a mouse ALS model. Nature. 429: 413-4I 7.

Badie N, et al. (2009) A method to replicate the microstructure of heart tissue in vitro using DTMRI-based cell micropatterning. Ann Biomed Eng. 37: 2510-2521.

Badie et al. (2009b) Novel micropatterned cardiac cell cultures with realistic ventricular microstructure. Biophysical Journal 96: 3873-3885.

Bahr M, et al. (1991) In vitro myelination of regenerating adult rat retinal ganglion cell axons by Schwann cells. Glia. 4: 529-533.

Baker DC, et al. (2002) The origin and neuronal function of in vivo nonsynaptic glutamate. J Neurosci. 22: 9134-9I41.

Bandi E, et al. (2008) Neural agrin controls maturation of the excitation-contraction coupling mechanism in human myotubes developing in vitro. Am J Physiol Cell Physiol. 294: C66-C73.

Bansal R and Pfeiffer SE. (1992) Novel stage in the oligodendrocyte lineage defined by reactivity of progenitors with R-mAb pnor to QI antigalactocerebroside. J Neurosci Res. 32: 309-3 I 6.

(56) References Cited

OTHER PUBLICATIONS

Baraban SC, et al. (1997) Osmolarity modulates K+ channel function on rat AI56. hippocampal interneurons but not CAI pyramidal neurons. J Physiol. 498: 679-689.
Barbulovic-Nad l, et al. (2008) Digital microfluidics for cell-based assays. Lab Chip. 8: 519-526.
Baron W, et al. (2000) PDGF and FGF-2 signaling in oligodendrocyte progenitor cells: regulation of proliferation and differentiation by multiple intracellular signaling pathways. Mol Cell Neurosci. 15: 314-329.
Barone FC, et al. (1998) Ischemic preconditioning and brain tolerance: temporal histological and functional outcomes, protein synthesis requirement, and interleukin-I receptor antagonist and early gene expression. Stroke. 29: 1937-1950.
Behar TN. (2001) Analysis of fractal dimension of O2A glial cells differentiating in vitro. Methods. 24: 331-339.
Belardinelli L, et al. (2003) Assessing predictors of drug-induced torsade de pointes. Trends Pharmacol Sci. 24: 619-625.
Bellamkonda R, et al. (1995) Hydrogel-based three-dimensional matrix for neural cells. J Biomed Mater Res. 29: 663-671.
Bellas E, et al. (2012) In vitro 3D full-thickness skin-equivalent tissue model using silk and collagen biomaterials. Macromol Biosci. 12: 1627-1236.
Benabid AI. (2003) Deep brain stimulation for Parkinson's disease. Curr Opin Neurobiol. 13: 696-706.
Bender A, et al. (2007) Analysis of pharmacology data and the prediction of adverse drug reactions and off-target effects from chemical structure. ChemMedChem. 2: 861-873.
Bentley A and Atkinsona, A. (2001) Whole cell biosensors—electrochemical and optical approaches to ecotoxicity testing. Toxicol In Vitro. 15: 469-475.
Berg MC, et al. (2004) Controlling mammalian cell interactions on patterned polyelectrolyte multilayer surfaces. Langmuir. 20: 1362-1368.
Berger TW, et al. (2001) Brain-implantable biomimetic electronics as the next era in neural prosthetics. Proceedings of the IEEE. 89: 993-1012.
Bernstein M, et al. (1996) Receptor-mediated calcium signalling in glial cells from mouse corpus callosum slices. J Neurosci Res. 46: 152-163.
Bers DM. (2002) Cardiac excitation-contraction coupling. Nature. 415: 198-205.
Bettinger CJ, et al. (2009) Engineering substrate topography at the micro- and nanoscale to control cell function. Angew Chem Int Ed Engl. 48: 5406-5415.
Bhalla US and Iyengar R. (1999) Emergent properties of networks of biological signaling pathways. Science. 283: 381-387.
Bhat NR, et al. (2007) p38 MAP kinase regulation of oligodendrocyte differentiation with CREB as a potential target. Neurochem Res. 32: 293-302.
Bian WN and Tung L. (2006) Structure-related initiation of reentry by rapid pacing in monolayers of cardiac cells. Circ Res. 98: e29-38.
Biesecker G. (1990) The complement SC5b-9 complex mediates cell adhesion through a vitronectin receptor. J Immunol. 145: 209-214.
Bikfalvi A, et al. (1997) Biological roles of fibroblast growth factor-2. Endocr Rev. 18: 26-45.
Bischoff U, et al. (2000) Effects of fluoroquinolones on HERG currents. Eur J Pharmacol. 406: 341-343.
Bloch-Gallego E, et al. (1991) Survival in vitro of motoneurons identified or purified by novel antibody-based methods is selectively enhanced by musclederived factors. Development. 111: 221-232.
Bodine SC, et al. (2001) Identification of ubiquitin ligases required for skeletal muscle atrophy. Science. 294: 1704-1708.
Bogler O, et al. (1990) Cooperation between two growth factors promotes extended self-renewal and inhibits differentiation of oligodendrocyte-type-2 astrocyte (0-2A) progenitor cells. Proc Natl Acad Sci US A. 87: 6368-6372.
Boillee S, et al. (2006) ALS: a disease of motor neurons and their nonneuronal neighbors. Neuron. 52: 39-59.
Boldin SA and Futerman AH. (2000) Up-regulation of glucosylceramide synthesis upon stimulation of axonal growth by basic fibroblast growth factor. Evidence for post-translational modification of glucosylceramide synthase. J Biol Chem. 275: 9905-9909.
Bordet T, et al. (2001) Protective effects of cardiotrophin-1 adenoviral gene transfer on neuromuscular degeneration in transgenic ALS mice. Hum Mol Genet. 10: 1925-1933.
Bottenstein JE, et al. (1988a) CNS neuronal cell line-derived factors regulate gliogenesis in neonatal rat brain cultures. J Neurosci Res. 20: 291-303.
Bottenstein JE. (1981) Proliferation of glioma cells in serum-free defined medium. Cancer Treat Rep. 65 Suppl 2: 67-70.
Bottenstein JE. (1988b) Advances in vertebrate cell culture methods. Science. 239: G 42, G 48.
Bourgeois EB, et al. (2009) Change in conduction velocity due to fiber curvature in cultured neonatal rat ventricular myocytes. IEEE Trans Biomed Eng. 56: 855-861.
Bousse L. (1996) Whole cell biosensors. Sens Actuators B: Chem. 34: 270-275.
Bowman WC. (2006) Neuromuscular block. Br J Pharmacol. 147 Suppl 1: S277-S286.
Bracciali A, et al. (2008) Stochastic models for the in silico simulation of synaptic processes. BMC Bioinformatics. 9 Suppl 4: S7.
Brand T, et al. (2000) EMBO Workshop Report: Molecular genetics of muscle development and neuromuscular diseases, Kloster Irsee, Germany, Sep. 26-Oct. 1, 1999. EMBO J. 19: 1935-1941.
Brand-Saberi B and Christ B. (1999) Genetic and epigenetic control of muscle development in vertebrates. Cell Tissue Res. 296: 199-212.
Brand-Saberi B. (2005) Genetic and epigenetic control of skeletal muscle development. Ann Anat. 187: 199-207.
Bregman BS, et al. (1997) Neurotrophic factors increase axonal growth after spinal cord injury and transplantation in the adult rat. Exp Neurol. 148: 475-494.
Bren-Mattison Y and Olwin BB. (2002) Sonic hedgehog inhibits the terminal A195. differentiation of limb myoblasts committed to the slow muscle lineage. Dev Biol. 242: 130-148.
Brewer GJ, et al. (1993) Optimized survival of hippocampal neurons in B27 supplemented Neurobasal, a new serum-free medium combination. J Neurosci Res. 35: 567-576.
Brewer GJ, et al. (2008) NbActiv4 medium improvement to Neurobasal/B27 increases neuron synapse densities and network spike rates on multielectrode arrays. J Neurosci Methods. 170: 181-187.
Brewer GJ. (1997) Isolation and culture of adult rat hippocampal neurons. J Neurosci Methods. 71: 143-155.
Brewer GJ. (1999) Regeneration and proliferation of embryonic and adult rat hippocampal neurons in culture. Exp Neurol. 159: 237-247.
Brito-Martins M, et al. (2008) beta(I)- and beta(2)-adrenoceptor responses in cardiomyocytes derived from human embryonic stem cells: comparison with failing and non-failing adult human heart. Br J Pharmacol. 153: 751-759.
Brockes JP, et al. (1979) Studies on cultured rat Schwann cells. I. Establishment of purified populations from cultures of peripheral nerve. Brain Res. 165: 105-118.
Brokhman I, et al. (2008) Peripheral sensory neurons differentiate from neural precursors derived from human embryonic stem cells. Differentiation. 76: 145-155.
Brumovsky P, et al. (2007) Expression of the vesicular glutamate transporters-I and -2 in adult mouse dorsal root ganglia and spinal cord and their regulation by nerve injury. Neuroscience. 147: 469-490.
Bult CJ, et al. (1996) Complete genome sequence of the methanogenic archaeon, *Methanococcus jannaschii*. Science. 273: 1058-1073.
Bunge MB, et al. (1962) Electron microscopic demonstration of connections between glia and myelin sheaths in the developing mammalian central nervous system. J Cell Biol. 12: 448-453.
Bunge RP. (1968) Glial cells and the central myelin sheath. Physiol Rev. 48: 197-251.
Bunge RP. (1993) Expanding roles for the Schwann cell: ensheathment, myelination, trophism and regeneration. Curr Opin Neurobiol. 3: 805-809.

(56) References Cited

OTHER PUBLICATIONS

Burdick JA and Vunjak-Novakovic G. (2009) Engineered microenvironments for controlled stem cell differentiation. Tissue Eng Part A. 15: 205-219.

Burgess C, et al. (2008) An endogenous glutamatergic drive onto somatic motoneurons contributes to the stereotypical pattern of muscle tone across the sleep-wake cycle. J Neurosci. 28: 4649-4660.

Butt HJ. (1996) Sensitive Method to Measure Changes in the Surface Stress of Solids. Journal of Colloid and Interface Science. 180: 251-260.

Buzanska L, et al. (2002) Human cord blood-derived cells attain neuronal and glial features in vitro. J Cell Sci. 115: 2131-2138.

Cai J, et al. (2007) Directed differentiation of human embryonic stem cells into functional hepatic cells. Hepatology. 45: 1229-1239.

Caiozzo VJ, at al. (1992) Response of slow and fast muscle to hypothyroidism: maximal shortening velocity and myosin isoforms. Am J Physiol. 263: C86-C94.

Cakir T, et al. (2007) Reconstruction and flux analysis of coupling between metabolic pathways of astrocytes and neurons: application to cerebral hypoxia. Theor Biol Med Model. 4: 48.

Campbell TJ and Williams KM. (2001) Therapeutic drug monitoring: antiarrhythmic drugs. Br J Clin Pharmacol. 52 Suppl 1: 21S-34S.

Camu Wand Henderson CE. (1992) Purification of embryonic rat motoneurons by panning on a monoclonal antibody to the low-affinity NGF receptor. J Neurosci Methods. 44: 59-70.

Camu W and Henderson CE. (1994) Rapid purification of embryonic rat motoneurons: an in vitro model for studying MND/ALS pathogenesis. J Neurol Sci. 124 Suppl: 73-74.

Cannon JG. (1998) Intrinsic and extrinsic factors in muscle aging. Ann NY Acad Sci. 854: 72-77.

Caratsch CG, et al. (1994) Interferon-alpha, beta and tumor necrosis factor-alpha enhance the frequency of miniature end-plate potentials at rat neuromuscular junction. Neurosci Lett. 166: 97-100.

Carlsson L. (2006) In vitro and in vivo models for testing arrhythmogenesis in drugs. J Intern Med. 259: 70-80.

Carpenedo RL, et al. (2007) Rotary suspension culture enhances the efficiency, yield, and homogeneity of embryoid body differentiation. Stem Cells. 25: 2224-2234.

Carr PA, et al. (1989) Parvalbumin is highly colocalized with calbindin D28k and rarely with calcitonin gene-related peptide in dorsal root ganglia neurons of rat. Brain Res. 497: 163-170.

Carrasco DI and English AW. (2003) Neurotrophin 4/5 is required for the normal development of the slow muscle fiber phenotype in the rat soleus. J Exp Biol. 206: 2191-2200.

Caspi O, et al. (2009) In vitro electrophysiological drug testing using human embryonic stem cell derived cardiomyocytes. Stem Cells Dev. 18: 161-172.

Catoire H, et al. (2008) Sirtuin inhibition protects from the polyalanine muscular dystrophy protein PABPN1. Hum Mol Genet. 17: 2108-2117.

Cerignoli F, et al. (2012) High throughput measurement of Ca2+ dynamics for drug risk assessment in human stem cell-derived cardiomyocytes by kinetic image cytometry. J Pharmacol Toxicol Methods. 66: 246-256.

Chambers SM, et al. (2009) Highly efficient neural conversion of human ES and iPS cells by dual inhibition of SMAD signaling. Nat Biotechnol. 27: 275-280.

Chandran S, et al. (1998) Regional potential for oligodendrocyte generation in the rodent embryonic spinal cord following exposure to EGF and FGF-2. Glia. 24: 382-389.

Chang JC, et al. (2001) Modulation of neural network activity by patterning. Biosens Bioelectron. 16: 527-533.

Charpentier A, et al. (1993) RRR-alpha-tocopheryl succinate inhibits proliferation and enhances secretion of transforming growth factor-beta (TGFbeta) by human breast cancer cells. Nutr Cancer. 19: 225-239.

Chaudhary KW, et al. (2006) Embryonic stem cells in predictive cardiotoxicity: laser capture microscopy enables assay development. Toxicol Sci. 90: 149-158.

Chaves M, et al. (2005) Robustness and fragility of Boolean models for genetic regulatory networks. J Theor Biol. 235: 431-449.

Chaves M, et al. (2006) Methods of robustness analysis for Boolean models of gene control networks. Syst Biol (Stevenage). 153: 154-167.

Chen CS, et al. (1997) Geometric control of cell life and death. Science. 276: 1425-1428.

Chen EW, et al. (1995) Target regulation of a motor neuron-specific epitope. J Neurosci. 15: 1555-1566.

Chen J and von Bartheld CS. (2004) Role of exogenous and endogenous trophic factors m the regulation of extraocular muscle strength during development.Invest Ophthalmol Vis Sci. 45: 3538-3545.

Chen QS, et al. (2000) Impairment of hippocampal long-term potentiation by Alzheimer amyloid beta-peptides. J Neurosci Res. 60: 65-72.

Chen X, et al. (2005) Dedifferentiation of adult human myoblasts induced by ciliary neurotrophic factor in vitro. Moll Biol Cell. 16: 3140-3151.

Chen XF, et al. (2008) Dynamic simulation of the effect of calcium-release activated calcium channel on cytoplasmic Ca2+ oscillation. Biophys Chem. 136: 87-95.

Chen XP, (2003) Exogenous rhCNTF inhibits myoblast differentiation of skeletal muscle of adult human in vitro. Sheng Li Xue Bao. 55: 464-468.

Chiu A Y, et al. (1993) A motor neuron-specific epitope and the low-affinity nerve growth factor receptor display reciprocal patterns of expression during development, axotomy, and regeneration. J Comp Neurol. 328: 351-363.

Choi-Lundberg DL and Bohn MC. (1995) Ontogeny and distribution of glial cell line-derived neurotrophic factor (GDNF) mRNA in rat. Brain Res Dev Brain Res. 85: 80-88.

Choudhury A, et al. (2007) A piezoresistive microcantilever array for surface stress measurement: curvature model and fabrication. J Micromech Microeng. 17: 2065-2076.

Chow I and Poo MM. (1985) Release of acetylcholine from embryonic neurons upon contact with muscle cell. J Neurosci. 5: 1076-1082.

Christ B and Brand-Seberi B. (2002) Limb muscle development. Int J Dev Biol. 46: 905-914.

Cizkova D, et al. (2007) Functional recovery in rats with ischemic paraplegia after spinal grafting of human spinal stem cells. Neuroscience. 147: 546-560.

Clegg CH, et al. (1987) Growth factor control of skeletal muscle differentiation: commitment to terminal differentiation occurs in G1 phase and is repressed by fibroblast growth factor. J Cell Biol. 105: 949-956.

Clements JD, et al. (1992) The time course of glutamate in the synaptic cleft. Science. 258: 1498-1501.

Coggan JS, et al. (2005) Evidence for ectopic neurotransmission at a neuronal synapse. Science. 309: 446-451.

Cohen RI and Almazan G. (1993) Norepinephrine-stimulated PI hydrolysis in oligodendrocytes is mediated by alpha IA-adrenoceptors. Neuroreport. 4: 1115-1118.

Cohen-Cory S. (2002) The developing synapse: construction and modulation of synaptic structures and circuits. Science. 298: 770-776.

Collins CA and Morgan JE. (2003) Duchenne's muscular dystrophy: animal models used to investigate pathogenesis and develop therapeutic strategies. Int J Exp Pathol. 84: 165-172.

Colomar A and Robitaille R. (2004) Glial modulation of synaptic transmission at the neuromuscular junction. Glia. 4 7: 284-289.

Cooper A, et al. (1976) The growth of mouse neuroblastoma cells in controlled orientations on thin films of silicon monoxide. Exp Cell Res. 103: 435-439.

Corey JM, et al. (1991) Compliance of hippocampal neurons to patterned substrate networks. J Neurosci Res. 30: 300-307.

(56) References Cited

OTHER PUBLICATIONS

Corey JM, et al. (1996) Micrometer resolution silane-based patterning of hippocampal neurons: critical variables in photoresist and laser ablation processes for substrate fabrication. IEEE Trans Biomed Eng. 43: 944-955.
Corey JM, et al. (1997) Differentiated B 104 neuroblastoma cells are a highresolution assay for micropatterned substrates. J Neurosci Methods. 75: 91-97.
Cortassa S, et al. (2003) An integrated model of cardiac mitochondrial energy metabolism and calcium dynamics. Biophys J. 84: 2734-2755.
Cossu G, et al. (1996) How is myogenesis initiated in the embryo? Trends Genet. 12: 218-223.
Courdier-Fruh I, et al. (2002) Glucocorticoid-mediated regulation of utrophin levels in human muscle fibers. Neuromuscul Disord. 12(Suppl 1): S95-S104.
Cross-Doersen D and Isfort RJ. (2003) A novel cell-based system for evaluating skeletal muscle cell hypertrophy-inducing agents. In Vitro Cell Dev Biol Animal. 39: 407-412.
Cukierman E, et al. (2002) Cell interactions with three-dimensional matrices. Curr Opin Cell Biol. 14: 633-639.
Cunningham JJ and Roussel MF. (2001) Cyclin-dependent kinase inhibitors in the development of the central nervous system. Cell Growth Differ. 12: 387-396.
Cuppini R, et al. (2001) Alpha-tocopherol controls cell proliferation in the adult rat dentate 12:vrus. Neurosci Lett. 303: 198-200.
Currie PD and Ingham PW. (1996) Induction of a specific muscle cell type by a hedgehog-like protein in zebrafish. Nature. 382: 452-455.
Curtis R, et al. (1988) Development of macroglial cells in rat cerebellum. I. Use of antibodies to follow early m VIVO development and migration of oligodendrocytes. J Neurocytol. 17: 43-54.
Cysyk J and Tung L. (2008) Electric field perturbations of spiral waves attached to millimeter-size obstacles. Biophys J. 94: 1533-1541.
Dakhel Y and Jamali F. (2006) Erythromycin potentiates PR interval prolonging effect of verapamil in the rat: a pharmacodynamic drug interaction. Toxicol Appl Pharmacol. 214: 24-29.
Daniels MP, et al. (2000) Rodent nerve-muscle cell culture system for studies of neuromuscular junction development: refinements and applications. Microsc Res Tech. 49: 26-37.
Daniels MP. (1990) Localization of actin, beta-spectrin, 43 × 10(3) Mr and 58 × 10(3) Mr proteins to receptor-enriched domains of newly formed acetylcholine receptor aggregates in isolated myotube membranes. J Cell Sci. 97(Pt 4): 615-626.
Daniels MP. (1997) Intercellular communication that mediates formation of the neuromusculariunction. Mol Neurobiol. 14: 143-170.
Das M, et al. (2003) Electrophysiological and morphological characterization of rat embryonic motoneurons in a defined system. Biotechnol Prog. 19: 1756-1761.
Das M, et al. (2004) Long-term culture of embryonic rat cardiomyocytes on an organosilane surface in a serum-free medium. Biomaterials. 25: 5643-5647.
Das M, et al. (2005) Adult rat spinal cord culture on an organosilane surface in a novel serum-free medium. In Vitro Cell Dev Biol Anim. 41: 343-348.
Das M, et al. (2006) A defined system to allow skeletal muscle differentiation and subsequent integration with silicon microstructures. Biomaterials. 27: 4374-4380.
Das M, et al. (2007a) Auto-catalytic ceria nanoparticles offer neuroprotection to adult rat spinal cord neurons. Biomaterials. 28: 1918-1925.
Das M, et al. (2007b) Differentiation of skeletal muscle and integration of myotubes with silicon microstructures using serum-free medium and a synthetic silane substrate. Nat Protoc. 2: 1795-1801.
Das M, et al. (2007c) Embryonic motoneuron-skeletal muscle co-culture in a defined system. Neuroscience. 146: 481-488.
Das M, et al. (2008) Temporal neurotransmitter conditioning restores the functional activity of adult spinal cord neurons in long-term culture. Exp Neurol. 209: 171-180.
Das M, et al. (2009a) Developing a novel serum-free cell culture model of skeletal muscle differentiation by systematically studying the role of different growth factors in myotube formation. In Vitro Cell Dev Biol Anim. 45: 378-387.
Das M, et al. (2009b) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.
Das M, et al. (2010) A defined long-term in vitro tissue engineered model of neuromuscular junctions. Biomaterials. 31: 4880-4888.
Datar R, et al. (2009) Cantilever Sensors: Nanomechanical Tools for Diagnostics. MRS Bulletin. 34: 449-454.
David JA and Pitman RM. (1982) The effects of axotomy upon the extrasynaptic acetylcholine sensitivity of an identified motoneurone m the cockroach *Periplaneta americana*. J Exp Biol. 98: 329-341.
Davis H, et al. (2012) Rat Cortical Oligodendrocyte-Embryonic Motoneuron Co-Culture: An In Vitro Axon-Oligodendrocyte Interaction Model. J Biomater Tissue Eng. 2: 206-214.
De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.
De Felice FG, et al. (2001) Inhibition of Alzheimer's disease beta-amyloid aggregation, neurotoxicity, and in vivo deposition by nitrophenols: implications for Alzheimer's therapy. FASEB J. 15: 1297-1299.
De Lange P, et al. (2006) Sequential changes in the signal transduction responses of skeletal muscle following food deprivation. FASEB J. 20: 2579-2581.
De Wilde J, et al. (2008) Short-term high fat-feeding results in morphological and metabolic adaptations m the skeletal muscle of C57BL/6J mice. Physiol Genomics. 32: 360-369.
Dell'Era P, et al. (2003) Fibroblast growth factor receptor-I is essential for in vitro cardiomyocyte development. Circ Res. 93: 414-420.
Denning C and Anderson D. (2008) Cardiomyocytes from human embryonic A291. stem cells as predictors of cardiotoxicity. Drug Discovery Today: Therapeutic Strategies. 5: 223-232.
Dennis RG and Kosnik IPE. (2000) Excitability and isometric contractile A292. properties of mammalian skeletal muscle constructs engineered in vitro. In Vitro Cell Dev Biol Anim. 36: 327-335.
Dennis RG, et al. (2001) Excitability and contractility of skeletal muscle A293. engineered from primary cultures and cell lines. Am J Physiol Cell Physiol. 280: C288-C295.
Denyer MCT, et al. (1998) Preliminary study on the suitability of a A294. pharmacological bio-assay based on cardiac myocytes cultured over microfabricated microelectrode arrays. Med Biol Eng Comput. 36: 638-644.
Descarries L, et al. (1997) Diffuse transmission by acetylcholine in the CNS. Prog Neurobiol. 53: 603-625.
Dhavan R and Tsai L. (2001) A decade of CDK5. Nat Rev Mol Cell Biol. 2: 749-759.
Dhir, V. (2003) Application of polyelectrolyte multilayers for photolithographic patterning of diverse mammalian cell types in serum free medium. Masters Thesis in the Department of Mechanical, Materials and Aerospace Engineering in the College of Engineering and Computer Science. University of Central Florida. Orlando, Florida, Fall Term 2008.
Dhir V, et al. (2009) Patterning of diverse mammalian cell types in serum free medium with photoablation. Biotechnol Prog. 25: 594-603.
Di Giovanni S, et al. (2005) Cell cycle inhibition provides neuroprotection and reduces glial proliferation and scar formation after traumatic brain injury. Proc Natl Acad Sci U SA. 102: 8333-8338.
Dimitrova DS and Gilbert DM. (2000) Temporally coordinated assembly and disassembly of replication factories in the absence of DNA synthesis. Nat Cell Biol. 2: 686-694.

(56) References Cited

OTHER PUBLICATIONS

Djouhri L and Lawson SN. (1999) Changes in somatic action potential shape in guinea-pig nociceptive primary afferent neurones during inflammation in vivo. J Physiol. 520 Pt 2: 565-576.

Dolcet X, et al. (2001) Cytokines promote motoneuron survival through the Janus kinase-dependent activation of the phosphatidylinositol 3-kinase pathway. Mol Cell Neurosci. 18: 619-631.

Du Y, et al. (2006) Distinct effects of p75 in mediating actions of neurotrophins on basal forebrain oligodendrocytes. Mol Cell Neurosci. 31: 366-375.

Dulcey CS, et al. (1991) Deep UV photochemistry of chemisorbed monolayers: patterned coplanar molecular assemblies. Science. 252: 551-554.

Dumont RJ, et al. (2001) Acute spinal cord injury, part I: pathophysiologic mechanisms. Clin Neuropharmacolo12:v. 24: 254-264.

Duport S, et al. (1999) A metallic multisite recording system designed for continuous long-term monitoring of electrophysiological activity in slice cultures. Biosens Bioelectron. 14: 369-376.

Dusterhoft S and Pette D. (1999) Evidence that acidic fibroblast growth factor promotes maturation of rat satellite-cell-derived myotubes m vitro. Differentiation. 65: 161-169.

Dutton EK, et al. (1995) Acetylcholine receptor aggregation at nerve-muscle contacts in mammalian cultures: induction by ventral spinal cord neurons is specific to axons. J Neurosci. 15: 7401-7416.

Edwards D, et al. (2010) Addition of glutamate to serum-free culture promotes recovery of electrical activity in adult hippocampal neurons in vitro. J Neurosci Methods. 190: 155-163.

Egert U, et al. (1998) A novel organotypic long-term culture of the rat hippocampus on substrate-integrated multielectrode arrays. Brain Res Brain Res Protoc. 2: 229-242.

Egert U, et al. (2006) Analysis of cardiac myocyte activity dynamics with microeletrode arrays. In: Taketani M BM, editor. Advances m netwrok electrophysiology using multi electrode arrays: Springer 2006. p. 274-290.

Eisen A and Swash M. (2001) Clinical neurophysiology of ALS. Clin Neurophysiol. 112: 2190-2201.

Eisenberg T, et al. (2009) Induction of autophagy by spermidine promotes longevity. Nat Cell Biol. 11: 1305-1314.

Eldridge CF, et al. (1989) Differentiation of axon-related Schwann cells in vitro: II. Control of myelin formation by basal lamina. J Neurosci. 9: 625-638.

Elia D, et al. (2007) Sonic hedgehog promotes proliferation and differentiation of adult muscle cells: Involvement of MAPK/ERK and PI3K/ Akt pathways. Biochim Biophys Acta. 1773: 1438-1446.

Emery AEH. (2002) The muscular dystrophies. Lancet. 359: 687-695.

Engler AJ, et al. (2006) Matrix elasticity directs stem cell lineage specification. Cell. 126: 677-689.

English AW. (2003) Cytokines, growth factors and sprouting at the neuromuscular junction. J Neurocytol. 32: 943-960.

Entcheva EK, et al. (2004) Fluorescence imaging of electrical activity in cardiac cells using an all-solid-state system. IEEE Trans Biomed Eng. 51: 331-341.

Ericson J, et al. (1992) Early stages of motor neuron differentiation revealed by expression ofhomeobox gene Islet-I. Science. 256: 1555-1560.

Esch MB, et al. (2011) The role of body-on-a-chip devices in drug and toxicity studies. Annu Rev Biomed Eng. 13: 55-72.

Esch MB, et al. (2012) On chip porous polymer membranes for integration of gastrointestinal tract epithelium with microfluidic 'body-on-a-chip' devices. Biomed Microdevices. 14: 895-906.

Eschenhagen T and Zimmermann WH. (2005) Engineering myocardial tissue. Circ Res. 97: 1220-1231.

Evans MS, et al. (1998) Electrophysiology of embryonic, adult and aged rat hippocampal neurons in serum-free culture. J Neurosci Methods. 79: 37-46.

Fan CM and Tessier-Lavigne M. (1994) Patterning of mammalian somites by surface ectoderm and notochord: evidence for sclerotome induction by a hedgehog homolog. Cell. 79: 1175-1186.

Faraut B, et al. (2004) Thrombin reduces MuSK and acetylcholine receptor expression along with neuromuscular contact size in vitro. Eur J Neurosci. 19: 2099-2108.

FDA (2004) Innovation or Stagnation: Challenge and Opportunity on the Critical Path to New Medical Products.

Fernandez-Valle C, et al. (1993) Expression of the protein zero myelin gene in axon-related Schwann cells is linked to basal lamina formation. Development. 119: 867-880.

Fernandez-Valle C, et al. (1995) Schwann cells degrade myelin and proliferate in the absence of macrophages: evidence from in vitro studies of Wallerian degeneration. J Neurocytol. 24: 667-679.

Fields GB, et al. (1998) Protein-like molecular architecture: biomaterial applications for inducing cellular receptor binding and signal transduction. Biopolymers. 47: 143-151.

Fields GB. (1999) Induction of protein-like molecular architecture by selfassembly processes. Bioorg Med Chem. 7: 75-81.

Figenschou A, et al. (1996) Cholinergic modulation of the action potential in rat hippocampal neurons. EurJ Neurosci. 8: 211-219.

Fink CC, et al. (1999) Determination of time-dependent inositol-1,4,5-trisphosphate concentrations during calcium release in a smooth muscle cell. Biophys J. 77: 617-628.

Fischbach GD and Cohen SA. (1973) The distribution of acetylcholine sensitivity over uninnervated and innervated muscle fibers grown in cell culture. Dev Biol. 31: 147-162.

Fischbach GD. (1972) Synapse formation between dissociated nerve and muscle cells in low density cell cultures. Dev Biol. 28: 407-429.

Fisher OZ, et al. (2010) Bioinspired materials for controlling stem cell fate. Ace Chem Res. 43: 419-428.

Fishman RA. (2002) The cerebrospinal fluid production rate is reduced in dementia of the Alzheimer's type. Neurology. 58: 1866; author reply 1866.

Flucher BE, et al. (1990) Localization of the alpha 1 and alpha 2 subunits of the dihydropyridine receptor and ankyrin in skeletal muscle triads. Neuron. 5:339-351.

Flucher BE, et al. (1991) Biogenesis of transverse tubules in skeletal muscle in vitro. Dev Biol. 145: 77-90.

Flucher BE, et al. (1992) Coordinated development of myofibrils, sarcoplasmic reticulum and transverse tubules in normal and dysgenic mouse skeletal muscle, in vivo and in vitro. Dev Biol. 150: 266-280.

Flucher BE, et al. (1994) Molecular organization of transverse tubule/sarcoplasmic reticulum junctions during development of excitationcontraction coupling in skeletal muscle. Mol Biol Cell. 5: 1105-1118.

Forry SP, et al. (2006) Facilitating the culture of mammalian nerve cells with polyelectrolyte multilayers. Langmuir. 22: 5770-5775.

Foster RF, et al. (1987) A laminin substrate promotes myogenesis in rat skeletal muscle cultures: analysis of replication and development using antidesmin and anti-BrdUrd monoclonal antibodies. Dev Biol. 122: 11-20.

Fowler VM, et al. (1993) Tropomodulin is associated with the free (pointed) ends of the thin filaments in rat skeletal muscle. J Cell Biol. 120: 411-420.

Fox MA, et al. (2007) Distinct target-derived signals orgamze formation, maturation, and maintenance of motor nerve terminals. Cell. 129: 179-193.

Francis PT. (2008) Glutamatergic approaches to the treatment of cognitive and behavioural symptoms of Alzheimer's disease. Neurodegener Dis. 5: 241-243.

Frank E and Fischbach GD. (1979) Early events in neuromuscular junction formation in vitro: induction of acetylcholine receptor clusters in the postsynaptic membrane and morphology of newly formed synapses. J Cell Biol. 83: 143-158.

Franzini-Armstrong C and Protasi F. (1997) Ryanodine receptors of striated muscles: a complex channel capable of multiple interactions. Physiol Rev. 77: 699-729.

Friedman B, et al. (1995) BDNF and NT-4/5 exert neurotrophic influences on injured adult spinal motor neurons. J Neurosci. 15: 1044-1056.

Fu X, et al. (1995) Acidic fibroblast growth factor reduces rat skeletal muscle damage caused by ischemia and reperfusion. Chin Med J (Engl). 108: 209-214.

(56) References Cited

OTHER PUBLICATIONS

Fuentes-Medel Y, et al. (2012) Integration of a retrograde signal during synapse formation by glia-secreted TGF-B ligand. Curr Biol. 22: 1831-1838.
Funakoshi H, et al. (1995) Muscle-derived neurotrophin-4 as an activitydependent trophic signal for adult motor neurons. Science. 268: 1495-1499.
Gajsek N, et al. (2006) Expression of MuSK in in vitro-innervated human muscle. J Mol Neurosci. 30: 27-28.
Gajsek N, et al. (2008) Synaptogenetic mechanisms controlling postsynaptic differentiation of the neuromuscular junction are nerve-dependent in human and nerve-independent in mouse C2C12 muscle cultures. Chem Biol Interact. 175:50-57.
Galizia CG and Menzel R. (2000) Probing the olfactory code. Nat Neurosci. 3: 853-854.
Gao BX and Ziskind-Conhaim L. (1995) Development of glycine- and GABAgated currents in rat spinal motoneurons. J Neurophysiol. 74: 113-121.
Gao Bx and Ziskind-Conhaim L. (1998) Development of ionic currents underlying changes in action potential waveforms in rat spinal motoneurons. J Neurophysiol. 80: 3047-3061.
Gao J, et al. (2005) Human neural stem cell-derived cholinergic neurons innervate muscle in motoneuron deficient adult rats. Neuroscience. 131: 257-262.
Garcez RC, et al. (2009) Epidermal growth factor (EGF) promotes the in vitro differentiation of neural crest cells to neurons and melanocytes. Cell Mol Neurobiol. 29: 1087-1091.
Garell PC, et al. (1998) Introductory overview of research instruments for recording the electrical activity of neurons in the human brain. Rev Sci Instrum. 69:4027-4037.
Gaud A, et al. (2004) Prednisone reduces muscle degeneration in dystrophindeficient Caenorhabditis elegans. Neuromuscul Disord. 14: 365-370.
Gaztañaga, L., Marchlinski, F. E., & Betensky, B. P. (2012). Mechanisms of cardiac arrhythmias. Revista Española de Cardiología (English Edition), 65(2), 174-185.
Georger JH, et al. (1992) Coplanar patterns of self-assembled monolayers for selective cell adhesion and outgrowth. Thin Solid Films. 210: 716-719.
Germani A, et al. (2003) Vascular endothelial growth factor modulates skeletal myoblast function. Am J Pathol. 163: 1417-1428.
Gerrard L, et al. (2005) Differentiation of human embryonic stem cells to neural lineages in adherent culture by blocking bone morphogenetic protein signaling. Stem Cells. 23: 1234-1241.
Ghiani CA, et al. (1999) Neurotransmitter receptor activation triggers p27(Kipl) and p21(CIP 1) accumulation and G 1 cell cycle arrest in oligodendrocyte progenitors. Development. 126: 1077-1090.
Ginsberg SD. (2005) Glutamatergic neurotransmission expression profiling in the mouse hippocampus after perforant-path transection. Am J Geriatr Psychiatry. 13: 1052-1061.
Glass Land Kauffman SA. (1973) The logical analysis of continuous, non-linear biochemical control networks. J Theor Biol. 39: 103-129.
Glass L. (197 5) Classification of biological networks by their qualitative dynamics. J Theor Biol. 54: 85-107.
Glass, D. J. (2003). Signalling pathways that mediate skeletal muscle hypertrophy and atrophy. Nat Cell Biol. 5: 87-90.
Golan H, et al. (2000) GABA withdrawal modifies network activity in cultured hippocampal neurons. Neural Plast. 7: 31-42.
Gold MR. (1982) The effects of vasoactive intestinal peptide on neuromuscular transmission in the frog. J Physiol. 327: 325-335.
Golden JP, et al. (1999) Expression of neurturin, GDNF, and GDNF family-receptor mRNA in the developing and mature mouse. Exp Neurol. 158: 504-528.
Gonzalez AM, et al. (1990) Distribution of basic fibroblast growth factor in the 18-day rat fetus: localization in the basement membranes of diverse tissues. J Cell Biol. 110: 753-765.
Goodyear S and Sharma MC. (2007) Roscovitine regulates invasive breast cancer cell (MDA-MB231) proliferation and survival through cell cycle regulatory protein cdk5. Exp Mol Pathol. 82: 25-32.
Goodyear S. (2005) Roscovitine induced cell death is mediated through specific inhibition of cell cycle regulatory protein cdk5. AACR Meeting Abstracts. 1045-d-1046.
Gordon AM, et al. (2000) Regulation of Contraction in Striated Muscle. Physiol Rev. 80: 853-924.
Goritz C, et al. (2005) Multiple mechanisms mediate cholesterol-induced synaptogenesis in a CNS neuron. Mol Cell Neurosci. 29: 190-201.
Gozes I, et al. (2004) NAP mechanisms of neuroprotection. J Mol Neurosci. 24: 67-72.
Graham SC, et al. (1992) Enzyme and size profiles in chronically inactive cat soleus muscle fibers. Muscle Nerve 15: 27-36.
Gramowski A, et al. (2006) Functional screening of traditional antidepressants with primary cortical neuronal networks grown on multielectrode neurochips. Eur J Neurosci. 24: 455-465.
Granchelli JA, et al. (2000) Pre-clinical screening of drugs using the mdx mouse. Neuromuscul Disord. 10: 235-239.
Greaves P, et al. (2004) First dose of potential new medicines to humans: how animals help. Nat Rev Drug Discov. 3: 226-236.
Greenstein JL and Winslow RL. (2002) An integrative model of the cardiac ventricular myocyte incorporating local control of Ca2+ release. Biophys J. 83:2918-2945.
Greenwood AL, et al. (1999) Identification of dividing, determined sensory neuron precursors in the mammalian neural crest. Development. 126: 3545-3559.
Gross GW, et al. (1993) Stimulation of monolayer networks in culture through thin-film indium-tin oxide recording electrodes. J Neurosci Methods. 50: 131-143.
Gross GW, et al. (1995) The Use of Neuronal Networks on Multielectrode Arrays as Biosensors. Biosens Bioelectron. 10: 553-567.
Gross GW, et al. (1997) Odor, drug and toxin analysis with neuronal networks in vitro: extracellular array recording of network responses. Biosens Bioelectron. 12: 373-393.
Groves MJ and Scaravelli F. (2005) Chapter 31—Pathology of Peripheral Neuron Cell Bodies. In: Dyck, PJ and Thomas, PK, (eds.) Peripheral neuropathy. 683-732. Elsevier Saunders: Philadelphia.
Grubic Z, et al. (1995) Myoblast fusion and innervation with rat motor nerve alter distribution of acetylcholinesterase and its mRNA in cultures of human muscle. Neuron. 14: 317-327.
Guenou H, et al. (2009) Human embryonic stem-cell derivatives for full reconstruction of the pluristratified epidermis: a preclinical study. Lancet. 374:1745-175.
Guettier-Sigrist S, et al. (1998) Muscle could be the therapeutic target in SMA treatment. J Neurosci Res. 53: 663-669.
Guettier-Sigrist S, et al. (2000) Cell types required to efficiently innervate human muscle cells in vitro. Exp Cell Res. 259: 204-212.
Gullberg D, et al. (1995) Analysis of fibronectin and vitronectin receptors on human fetal skeletal muscle cells upon differentiation. Exp Cell Res. 220: 112-123.
Guo JZ, et al. (2005) Synaptically released and exogenous ACh activates different nicotinic receptors to enhance evoked glutamatergic transmission in the lateral geniculate nucleus. J Neurophysiol. 94: 2549-2560.
Guo X, et al. (2011) Neuromuscular junction formation between human stem cell-derived motoneurons and human skeletal muscle in a defined system. Biomaterials. 32: 9602-9611.
Guo X, et al. (2012) Tissue engineering the monosynaptic circuit of the stretch reflex arc with co-culture of embryonic motoneurons and proprioceptive sensory neurons. Biomaterials. 33: 5723-5731.
Guo X, et al. (2013) Derivation of sensory neurons and neural crest stem cells from human neural progenitor hNPI. Biomaterials. 34: 4418-4427.
Guo XF, et al. (2010a) Characterization of a human fetal spinal cord stem cell line, NSI-566RSC, and its induction to functional motoneurons. J Tissue Eng Regen Med. 4: 181-193.
Guo XF, et al. (2010b) Neuromuscular junction formation between human stem-cell-derived motoneurons and rat skeletal muscle in a defined system. Tissue Eng Part C Methods. 16: 1347-1355.
Gupta S, et al. (2007) Boolean network analysis of a neurotransmitter signaling pathway. J Theor Biol. 244: 463-469.

(56) References Cited

OTHER PUBLICATIONS

Gureviciene I, et al. (2004) Normal induction but accelerated decay of LTP in APP+ PSI transgenic mice. Neurobiol Dis. 15: 188-195.
Haas HL and Selbach 0. (2000) Functions of neuronal adenosine receptors. Naunyn Schmiedebergs Arch Pharmacol. 362: 375-381.
Halbach M, et al. (2003) Estimation of action potential changes from field potential recordings in multicellular mouse cardiac myocyte cultures. Cell Physiol Biochem. 13: 271-284.
Hall BK and Miyake T. (2000) All for one and one for all: condensations and the initiation of skeletal development. Bioessays. 22: 138-147.
Hamaguchi T, et al. (2006) Anti-amyloidogenic therapies: strategies for prevention and treatment of Alzheimer's disease. Cell Mol Life Sci. 63: 1538-1552.
Hammarback JA, et al. (1985) Guidance of neurite outgrowth by pathways of substratum-adsorbed laminin. J Neurosci Res. 13: 213-220.
Han DK and Hubbell JA. (1997) Synthesis of Polymer Network Scaffolds from 1-Lactide and Poly( ethylene glycol) and Their Interaction with Cells. Macromolecules. 30: 607-6083.
Hantai D, et al. (1991) Developmental appearance of thrombospondin in neonatal mouse skeletal muscle. Eur J Cell Biol. 55: 286-294.
Harding SE, et al. (2007) The human embryonic stem cell-derived cardiomyocyte as a pharmacological model. Pharmacol Ther. 113: 341-353.
Hardy J and Selkoe DJ. (2002) The amyloid hypothesis of Alzheimer's disease: progress and problems on the road to therapeutics. Science. 297: 353-356.
Hari L, et al. (2002) Lineage-specific requirements of beta-catenin in neural crest development. J Cell Biol. 159: 867-880.
Harms H, et al. (2006) Whole-cell living biosensors—are they ready for environmental application? Appl Microbiol Biotechnol. 70: 273-280.
Harper JM, et al. (2004) Axonal growth of embryonic stem cell-derived motoneurons in vitro and in motoneuron-injured adult rats. Proc Natl Acad Sci U s A. 101: 7123-7128.
Harsch A, et al. (1997) Strychnine analysis with neuronal networks in vitro: extracellular array recording of network responses. Biosens Bioelectron. 12: 827-835.
Heiduschka P and Thanos S. (1998) Implantable bioelectric interfaces for lost nerve functions. Prog Neurobiol. 55: 433-461.
Heinrich G. (2003) A novel BDNF gene promoter directs expression to skeletal muscle. BMC Neurosci. 4: 11.
Henderson CE, et al. (1993) Neurotrophins promote motor neuron survival and are present in embryonic limb bud. Nature. 363: 266-270.
Henderson CE, et al. (1994) GDNF: a potent survival factor for motoneurons present in peripheral nerve and muscle. Science. 266: 1062-1064.
Hennessey JV, et al. (1997) Increase in percutaneous muscle biopsy yield with a suction-enhancement technique. J Appl Physiol. 82: 1739-1742.
Hennessey N, et al. (2001) Growth hormone administration and exercise effects on muscle fiber type and diameter in moderately frail older people. J Am Geriatr Soc. 49: 852-858.
Hermann M, et al. (2006) Exposure of atorvastatin is unchanged but lactone and acid metabolites are increased several-fold in patients withatorvastatin-induced myopathy. Clin Pharmacol Ther. 79: 532-539.
Herrup K and Yang Y. (2007) Cell cycle regulation in the postmitotic neuron: oxymoron or new biology? Nat Rev Neurosci. 8: 368-378.
Hickman J, et al. (1993) The use of monlayers as templates for biocompatibility studies. Abstracts of Papers of the American Chemical Society. 205: 146-Coll.
Hickman J. (2005) Building Minimalistic Hybrid Neuroelectric Devices in Toward Replacement Parts for the Brain: Implantable Biomimetic Electronics as Neural Prosthetic (T.W. Berger and D.L. Glanzman Eds.), 1st edition. Cambridge, MA: MIT Press.
Hickman JJ, et al. (1994) Rational Pattern Design for in-Vitro Cellular Networks Using Surface Photochemistry. J Vac Science Technol A. 12: 607-616.
Hirano A. (1968) A confirmation of the oligodendroglial origin of myelin in the adult rat. J Cell Biol. 38: 637-640.
Hjerling-Leffler J, et al. (2005) The boundary cap: a source of neural crest stem cells that generate multiple sensory neuron subtypes. Development. 132: 2623-2632.
Hoffman EP and Escolar D. (2006) Translating mighty mice into neuromuscular therapeutics: is bigger muscle better? Am J Pathol. 168: 177 5-1778.
Hoffmann F and Bading H. (2006) Long term recordings with microelectrode arrays: studies of transcription-dependent neuronal plasticity and axonal regeneration. J Physiol Paris. 99: 125-132.
Holleran AL, et al. (1995) Glutamine metabolism in AS-30D hepatoma cells. Evidence for its conversion into lipids via reductive carboxylation. Mol Cell Biochem. 152: 95-101.
Hondeghem LM and Hoffinan P. (2003b) Blinded test in isolated female rabbit heart reliably identifies action potential duration prolongation and proarrhythmic drugs: importance of triangulation, reverse use dependence, and instability. J Cardiovasc Pharmacol. 41: 14-24.
Hondeghem LM, et al. (2001) Instability and triangulation of the action potential predict serious proarrhythmia, but action potential duration prolongation is antiarrhythmic. Circulation. 103: 2004-2013.
Hondeghem LM, et al. (2003a) Detection of proarrhythmia in the female rabbit heart: blinded validation. J Cardiovasc Electrophysiol. 14: 287-29.
Hondeghem LM. (2006) Thorough QT/QTc not so thorough: removes torsadogenic predictors from the T-wave, incriminates safe drugs, and misses profibrillatory drugs. J Cardiovasc Electrophysiol. 17: 337-340.
Hondeghem LM. (2007) Relative contributions of TRiaD and QT to proarrhythmia. J Cardiovasc Electrophysiol. 18: 655-657.
Hsiao CF, et al. (2005) Voltage-dependent calcium currents in trigeminal motoneurons of early postnatal rats: modulation by 5-HT receptors. J Neurophysiol. 94: 2063-2072.
Hu BY, et al. (2009) Human oligodendrocytes from embryonic stem cells: conserved SHH signaling networks and divergent FGF effects. Development. 136: 1443-1452.
Hua JY and Smth SJ. (2004) Neural activity and the dynamics of central nervous system development. Nat Neurosci. 7: 327-332.
Huang Y, et al. (2007) An alphaiA-adrenergic-extracellular signal-regulated kinase survival signaling pathway in cardiac myocytes. Circulation. 115: 763-772.
Huang YC, et al. (2005) Rapid formation of functional muscle in vitro using fibrin gels. J Appl Physiol. 98: 706-713.
Hucka M, et al. (2003) The systems biology markup language (SBML): a medium for representation and exchange of biochemical network models. Bioinformatics. 19: 524-531.
Hughes B. (2008) 2007 FDA drug approvals: a year of flux. Nat Rev Drug Discov. 7: 107-109.
Huh D, et al. (2010) Reconstituting organ-level lung functions on a chip. Science. 328: 1662-1668.
Huh D, et al. (2012) Microengineered physiological biomimicry: organs-onchips. Lab Chip. 12: 2156-2164.
Hui EE and Bhatia SN. (2007) Microscale control of cell contact and spacing via three-component surface patterning. Langmuir. 23: 4103-4107.
Hung SC, et al. (2002) In vitro differentiation of size-sieved stem cells into electrically active neural cells. Stem Cells. 20: 522-529.
Husmann I, et al. (1996) Growth factors in skeletal muscle regeneration. Cytokine Growth Factor Rev. 7: 249-258.
Huxley, A. F. (1975). The origin of force in skeletal muscle. Ciba Found Symp. 31: 271-290.
Ichikawa H, et al. (2004) Effect of Bm-3a deficiency on parvalbumin-immunoreactive primary sensory neurons in the dorsal root ganglion. Brain Res Dev Brain Res. 150: 41-45.
Inoue N, et al. (2004) Rapid electrical stimulation of contraction modulates gap junction protein m neonatal rat cultured cardiomyocytes: involvement of mitogen-activated protein kinases and effects of angiotensin II-receptor antagonist. J Am Coll Cardiol. 44: 914-922.

(56) References Cited

OTHER PUBLICATIONS

Iravanian S, et al. (2003) Functional reentry in cultured monolayers of neonatal rat cardiac cells. Am J Physiol Heart Circ Physiol. 285: H449-H456.
Ito Y. (1999) Surface micropatterning to regulate cell functions. Biomaterials. 20:2333-2342.
Izrael M, et al. (2007) Human oligodendrocytes derived from embryonic stem cells: Effect of noggin on phenotypic differentiation in vitro and on myelination in vivo. Mol Cell Neurosci. 34: 310-323.
Izumiya Y, et al. (2008) Fast/glycolytic muscle fiber growth reduces fat mass and improves metabolic parameters in obese mice. Cell Metabolism. 7: 159-172.
Jackson JH 4th, et al. (2004) Assessment of drug therapy management and the prevalence of heart failure in a managed care population with hypertension. J Manag Care Pharm. 10: 513-520.
Jaworska-Wilczynska M, et al. (2002) Three lipoprotein receptors and cholesterol in inclusion-body myositis muscle. Neurology. 58: 438-445.
Jensen J, et al. (2009) Human embryonic stem cell technologies and drug discovery. J Cell Physiol. 219: 513-519.
Jessen KR and Mirsky R. (2005) The origin and development of glial cells in peripheral nerves. Nat Rev Neurosci. 6: 671-682.
Jevsek M, et al. (2004) Origin of acetylcholinesterase in the neuromuscular junction formed in the in vitro innervated human muscle. Eur J Neurosci. 20:2865-2871.
Jhamandas JH, et al. (2001) Cellular mechanisms for amyloid beta-protein activation of rat cholinergic basal forebrain neurons. J Neurophysiol. 86: 1312-1320.
Jiang XH, et al. (2009) Isolation and characterization of neural crest stem cells derived from in vitro-differentiated human embryonic stem cells. Stem Cells Dev. 18: 1059-1070.
Jiang Z and Clemens PR. (2006) Cellular caspase-8-like inhibitory protein (cFLIP) prevents inhibition of muscle cell differentiation induced by cancer cells. FASEB J. 20: 2570-2572.
Jiang ZG, et al. (1990) Excitatory and inhibitory transmission from dorsal root afferents to neonate rat motoneurons in vitro. Brain Res. 535: 110-118.
Jin P, et al. (1991) Recombinant platelet-derived growth factor-BB stimulates growth and inhibits differentiation of rat L6 myoblasts. J Biol Chem. 266: 1245-1249.
Johnson TE, et al. (2005) Statins and PPARalpha agonists induce myotoxicity in differentiated rat skeletal muscle cultures but do not exhibit synergy with cotreatment. Toxicol Appl Pharmacol. 208: 210-221.
Julius D and Basbaum AI. (2001) Molecular mechanisms of nociception. Nature. 413: 203-210.
Jung DR, et al. (1998) Cell-Based Sensor Microelectrode Array Characterized by Imaging X-ray Photoelectron Spectroscopy, Scanning Electron Microscopy, /mpedance Measurements, and Extracellular Recordings. Journal of Vacuum Science & Technology A (Vacuum, Surfaces, and Films). 16: 1183-1188.
Jung DR, et al. (2001) Topographical and physicochemical modification of material surface to enable patterning of living cells. Crit Rev Biotechnol. 21: 111-154.
Jurdana M, et al. (2009) Neural agrin changes the electrical properties of developing human skeletal muscle cells. Cell Mol Neurobiol. 29: 123-131.
Kaeberlein M. (2009) Spermidine surprise for a long life. Nat Cell Biol. 11:1277-1278.
Kaji H, et al. (2003) Pharmacological characterization of micropatterned cardiac myocytes. Biomaterials. 24: 4239-4244.
Kamp TJ. (2009) Human pluripotent stem cell-derived cardiomyocytes for safety pharmacology applications. Journal of Pharmacological and Toxicological Methods. 60: 259.
Kane RS, et al. (1999) Patterning proteins and cells using soft lithography. Biomaterials. 20: 2363-2376.
Kang JH, et al. (2009) In vitro 3D model for human vascularized adipose tissue. Tissue Eng Part A. 15: 2227-2236.
Kato AC and Lindsay RM. (1994) Overlapping and additive effects of neurotrophins and CNTF on cultured human spinal cord neurons. Exp Neurol. 130: 196-20.
Katsuki H, et al. (2000) Distinct signaling pathways involved in multiple effects of basic fibroblast growth factor on cultured rat hippocampal neurons. Brain Res. 885: 240-250.
Katz LC and Shatz CJ. (1996) Synaptic activity and the construction of cortical circuits. 274: 1133-1138.
Kauffman S, et al. (2003) Random Boolean network models and the yeast transcriptional network. Proc Natl Acad Sci US A. 100: 14796-14799.
Kauffman S. (1971) Gene regulation networks: a theory for their global structure and behaviors. Curr Top Dev Biol. 6: 145-182.
Kaufmann P, et al. (2006) Toxicity of statins on rat skeletal muscle mitochondria. Cell Mol Life Sci. 63: 2415-2425.
Keefer EW, et al. (2001a) Acute toxicity screening of novel AChE inhibitors using neuronal networks on microelectrode arrays. Neurotoxicology. 22: 3-1.
Keefer EW, et al. (2001b) Characterization of acute neurotoxic effects of trimethylolpropane phosphate via neuronal network biosensors. Biosens Bioelectron. 16: 513-525.
Kessaris N, et al. (2008) Specification of CNS glia from neural stem cells in the embryonic neuroepithelium. Philos Trans R Soc Lond B Biol Sci. 363: 71-85.
Khademhosseini A, et al. (2006a) Interplay of biomaterials and micro-scale technologies for advancing biomedical applications. J Biomater Sci Polym Ed. 17: 1221-1240.
Khademhosseini A, et al. (2006b) Microscale technologies for tissue engineering and biology. Proc Natl Acad Sci USA. 103: 2480-2487.
Khorchid A, et al. (1999) Characterization of the signal transduction pathways mediating noradrenaline-stimulated MAPK activation and c-fos expression in oligodendrocyte progenitors. JNeurosci Res. 58: 765-778.
Khorchid A, et al. (2002) Developmental regulation of alpha IA-adrenoceptor function in rat brain oligodendrocyte cultures. Neuropharmacology. 42: 685-696.
Kidambi S, et al. (2004) Controlling primary hepatocyte adhesion and spreading on protein-free polyelectrolyte multilayer films. J Am Chem Soc. 126: 16286-16287.
Kidambi S, et al. (2007a) Patterned co-culture of primary hepatocytes and fibroblasts using polyelectrolyte multilayer templates. Macromol Biosci. 7: 344-353.
Kidambi S, et al. (2007b) Cell adhesion on polyelectrolyte multilayer coated polydimethylsiloxane surfaces with varying topographies. Tissue Eng. 13: 2105-2117.
Kidd, J. (2006). Life after statin patent expiries. Nat Rev Drug Discov. 5: 813-814.
Kim C, et al. (2010) Non-cardiomyocytes influence the electrophysiological maturation of human embryonic stem cell-derived cardiomyocytes during differentiation. Stem Cells Dev. 19: 783-795.
Kim D-H, et al. (2005) Modulation of adhesion and growth of cardiac myocytes by surface nanotopography. Proceedings of the 2005 IEEE. Engineering in Medicine and Biology 27th Annual Conference. Shanghai, China, Sep. 1-4, 2005.
Kim J, et al. (2002) Dopamine neurons derived from embryonic stem cells function in an animal model of Parkinson's disease. Nature. 418: 50-56.
Kim K, et al. (2011) Calibrated micropost arrays for biomechanical characterization of cardiomyocytes. Micro and Nano Letters. 6: 317-322.
Kim SU, et al. (2002) Production of immortalized human neural crest stem cells. Methods Mol Biol. 198: 55-65.
Kim, Jinseok, et al. "Biohybrid microsystems actuated by cardiomyocytes: microcantilever, microrobot, and micropump." Robotics and Automation, 2008. ICRA 2008. IEEE International Conference on. IEEE, 2008.
Kim, IEEE poster. Micropatterning of Cardiomyocytes Using Adhesion-Resistant Polymeric Microstructures, The 13th International Conference on Solid-State Sensors, Actuators and Microsystems, Seoul, Korea, Jun. 5-9, 2005.

(56) References Cited

OTHER PUBLICATIONS

King T, et al. (2000) Piezoactuators for 'real-world' applications—Can they deliver sufficient displacement? Power Engineering. 14: 105-110.

Kingshott P and Griesser HJ. (1999) Surfaces that resist bioadhesion. Current Opinion in Solid State and Materials Science. 4: 403-412.

Kirazov E, et al. (2008) Amyloid beta peptides exhibit functional neurotoxicity to cortical network cultures. Compt Rend Acad Bulg Sci. 61: 905-910.

Kita-Matsuo H, et al. (2009) Lentiviral vectors and protocols for creation of stable hESC lines for fluorescent tracking and drug resistance selection of cardiomyocytes. PLoS One. 4: e5046.

Kleber AG and Rudy Y. (2004) Basic mechanisms of cardiac impulse propagation and associated arrhythmias. Physiol Rev. 84: 431-488.

Klein C, et al. (2002) Zinc inhibition of cAMP signaling. J Biol Chem. 277: 11859-11865.

Klein WL. (2002) Abeta toxicity in Alzheimer's disease: globular oligomers (ADDLs) as new vaccine and drug targets. Neurochem Int. 41: 345-352.

Kleinfeld D, et al. (1988) Controlled outgrowth of dissociated neurons on patterned substrates. J Neurosci. 8: 4098-4120.

Knobloch M and Mansuy IM. (2008) Dendritic spine loss and synaptic alterations in Alzheimer's disease. Mol Neurobiol. 37: 73-82.

Kobayashi T, et al. (1985) Acetylcholine receptors and acetylcholinesterase accumulate at the nerve-muscle contacts of de novo grown human monolayer muscle cocultured with fetal rat spinal cord. Exp Neurol. 88: 327-335.

Kobayashi T, et al. (1987) Human muscle cultured in monolayer and cocultured with fetal rat spinal cord: importance of dorsal root ganglia for achieving successful functional innervation. JNeurosci. 7: 3131-3141.

Koike T, et al. (2008) Axon & dendrite degeneration: its mechanisms and protective experimental paradigms. Neurochem Int. 52: 751-760.

Koirala S, et al. (2003) Roles of glial cells in the formation, function, and maintenance of the neuromuscular junction. J Neurocytol. 32: 987-1002.

Koleva M, et al. (2005) Pleiotropic effects of sonic hedgehog on muscle satellite cells. Cell Mol Life Sci. 62: 1863-1870.

Koliatsos VE, et al. (2008) Human stem cell grafts as therapies for motor neuron disease. Expert Opin Biol Ther. 8: 137-141.

Kontrogianni-Konstantopoulos A, et al. (2009) Muscle giants: molecular scaffolds in sarcomerogenesis. Physiol Rev. 89: 1217-1267.

Kornblum HI, et al. (1999) Multiple trophic actions of heparin-binding epidermal A511. growth factor (HB-EGF) in the central nervous system. Eur J Neurosci. 11: 3236-3246.

Kucera J and Dorovini-Zis K. (1979). Types of human intrafusal muscle fibers. Muscle Nerve. 2: 437-451.

Kucera J and Walro J. (1992) Axotomy induces fusimotor-free muscle spindles in neonatal rats. Neurosci Lett. 136: 216-218.

Kucera J, et al. (1989) Role of nerve and muscle factors in the development of rat muscle spindles. Am J Anat. 186: 144-160.

Kucera J. (1982a) One-bag-fiber muscle spindles in tenuissimus muscles of the cat. Histochemistry and Cell Biology. 76: 315-328.

Kucera, J. (1982b). The topography of long nuclear chain intrafusal fibers in the cat muscle spindle. Histochemistry. 74: 183-197.

Kucera, J. (1983). Multiple-bag-fiber muscle spindles in tenuissimus muscles of the cat. Histochemistry. 79: 457-476.

Kudla AJ, et al. (1995) A requirement for fibroblast growth factor in regulation of A518. skeletal muscle growth and differentiation cannot be replaced by activation of platelet-derived growth factor signaling pathways. Mol Cell Biol. 15: 3238-3246.

Kuhl U, et al. (1982) Synthesis of type IV collagen and laminin in cultures of skeletal muscle cells and their assembly on the surface of myotubes. Dev Biol. 93: 344-354.

Kuhl U, et al. (1986) Role of laminin and fibronectin in selecting myogenic versus fibrogenic cells from skeletal muscle cells in vitro. Dev Biol. 117: 628-635.

Kumar S, et al. (1998) NT-3-mediated TrkC receptor activation promotes proliferation and cell survival of rodent progenitor oligodendrocyte cells in vitro and in vivo. J Neurosci Res. 54: 754-765.

Kurek JB, et al. (1996) Leukemia inhibitory factor and interleukin-6 are produced by diseased and regenerating skeletal muscle. Muscle Nerve. 19: 1291-1301.

Lacor PN, et al. (2007a) Abeta oligomer-induced aberrations m synapse composition, shape, and density provide a molecular basis for loss of connectivity in Alzheimer's disease. J Neurosci. 27: 796-807.

Lacor PN. (2007b) Advances on the understanding of the origins of synaptic pathology in AD. Curr Genomics. 8: 486-508.

Laflamme MA, et al. (2007) Cardiomyocytes derived from human embryonic stem cells in pro-survival factors enhance function of infarcted rat hearts. Nat Biotechnol. 25: 1015-1024.

Lamb TM, et al. (1993) Neural induction by the secreted polypeptide noggin. Science. 262: 713-718.

Lambert MP, et al. (1998) Diffusible, nonfibrillar ligands derived from Abeta1-42 are potent central nervous system neurotoxins. Proc Natl Acad Sci US A. 95:6448-6453.

Lambeth MJ and Kushmerick MJ. (2002) A computational model for glycogenolvsis in skeletal muscle. Ann Biomed Eng. 30: 808-827.

Lambrechts D, et al. (2003) VEGF is a modifier of amyotrophic lateral sclerosis in mice and humans and protects motoneurons against ischemic death. Nat Genet. 34: 383-394.

Langen RC, et al. (2003) Enhanced myogenic differentiation by extracellular matrix is regulated at the early stages of myogenesis. In Vitro Cell Dev Biol Anim. 39: 163-169.

Langer Rand Vacanti JP. (1993) Tissue engineering. Science. 260: 920-926.

Larkin LM, et al. (2006) Functional evaluation of nerve-skeletal muscle constructs engineered in vitro. In Vitro Cell Dev Biol Anim. 42: 75-82.

Larsson L and Ansved T. (1995) Effects of ageing on the motor unit. Prog Neurobiol. 45: 397-415.

Lasser KE, et al. (2002) Timing of new black box warnings and withdrawals for prescription medications. JAMA. 287: 2215-2220.

Lawrence CL, et al. (2005) Nonclinical proarrhythmia models: predicting Torsades de Pointes. J Pharmacol Toxicol Methods. 52: 46-59.

Lawrence CL, et al. (2006) A rabbit Langendorff heart proarrhythmia model: predictive value for clinical identification of Torsades de Pointes. Br J Pharmacol. 149: 845-860.

Le Douarin NM and Dupin E. (2003) Multipotentiality of the neural crest. Curr Opin Genet Dev. 13: 529-536.

Lee A. (2005) Isolation of neural stem cells from the postnatal cerebellum. Nat Neurosci. 8: 723-729.

Lee EW, et al. (2003) Neuropeptide Y induces ischemic angiogenesis and restores function of ischemic skeletal muscles. J Clin Invest. 111: 1853-1862.

Lee G, et al. (2007) Isolation and directed differentiation of neural crest stem cells derived from human embryonic stem cells. Nat Biotechnol. 25: 1468-1475.

Lee G, et al. (2010) Derivation of neural crest cells from human pluripotent stem cells. Nat Protoc. 5: 688-701.

Lee HY, et al. (2004) Instructive role of Wnt/beta-catenin in sensory fate specification in neural crest stem cells. Science. 303: 1020-1023.

Lee MJ, et al. (2003) Hereditary sensory neuropathy is caused by a mutation in the delta subunit of the cytosolic chaperonin-containing t-complex peptide-I (Cct4) gene. Hum Mol Genet. 12: 1917-1925.

Lesbordes JC, et al. (2002) In vivo electrotransfer of the cardiotrophin-1 gene into skeletal muscle slows down progression of motor neuron degeneration in pmn mice. Hum Mol Genet. 11: 1615-1625.

Lescaudron L, et al. (1999) Blood borne macrophages are essential for the triggering of muscle regeneration following muscle transplant. Neuromuscul Disord. 9: 72-80.

(56) References Cited

OTHER PUBLICATIONS

Levenberg S, et al. (2003) Differentiation of human embryonic stem cells on three-dimensional polymer scaffolds. Proc Natl Acad Sci U S A. 100: 12741-12746.
LeVine SM and Goldman JE. (1988) Embryonic divergence of oligodendrocyte and astrocyte lineages in developing rat cerebrum. J Neurosci. 8: 3992-4006.
Li B-S, et al. (2001) Regulation of NMDA receptors by cyclin-dependent kinase-5 Proc Natl Acad Sci US A. 98: 12742-12747.
Li L and Olson EN. (1992) Regulation of muscle cell growth and differentiation by the MyoD family of helix-loop-helix proteins. Adv Cancer Res. 58: 95-119.
Li M, et al. (2005) Comparison of selective attachment and growth of smooth muscle cells on gelatin- and fibronectin-coated micropatterns. J Nanosci Nanotechnol. 5: 1809-1815.
Li MX, et al. (2001) Opposing actions of protein kinase A and C mediate Hebbian synaptic plasticity. Nat Neurosci. 4: 871-872.
Li S, et al. (2006) Predicting essential components of signal transduction networks: a dynamic model of guard cell abscisic acid signaling. PLoS Biol. 4:e312.
Li XJ, et al. (2005) Specification of motoneurons from human embryonic stem cells. Nat Boltechnol. 23: 215-221.
Lim GP, et al. (2001) The curry spice curcumin reduces oxidative damage and amyloid pathology in an Alzheimer transgenic mouse. J Neurosci. 21: 8370-8377.
Lim UM, et a. (2006) Derivation of Motor Neurons from three Clonal Human Embryonic Stem Cell Lines. CurrNeurovasc Res. 3: 281-288.
Lin JW, et al. (2008) Region of slowed conduction acts as core for spiral wave reentry in cardiac cell monolayers. Am J Physiol Heart Circ Physiol. 294: H58-H65.
Lin LF, et al. (1993) GDNF: a glial cell line-derived neurotrophic factor for midbrain dopaminergic neurons. Science. 260: 1130-1132.
Lipsett MA, et al. (2007) Acinar plasticity: development of a novel in vitro model to study human acinar-to-duct-to-islet differentiation. Pancreas. 34: 452-457.
Lipton SA. (2006) Paradigm shift in neuroprotection by NMDA receptor blockade: Memantine and beyond. Nat Rev Drug Discov. 5: 160-170.
Lisak RP, et al. (1997) The role of cytokines in Schwann cell damage, protection, and repair. J Infect Dis. 176 Suppl 2: S173-S179.
Liu CN, et al. (2000) Spinal nerve injury enhances subthreshold membrane potential oscillations m DRG neurons: relation to neuropathic pam. J Neurophysiol. 84: 205-215.
Liu J, et al. (2008) Electrophysiological and Immunocytochemical Characterization of DRG Neurons on an Organosilane Surface in Serum Free Medium. In Vitro Cell Dev Biol Anim. 44: 162-168.
Liu S, et al. (2000) Embryonic stem cells differentiate into oligodendrocytes and myelinate in culture and after spinal cord transplantation. Proc Natl Acad Sci USA. 97: 6126-6131.
Liu TX, et al. (2006) Blinded validation of the isolated arterially perfused rabbit ventricular wedge in preclinical assessment of drug-induced proarrhythmias. Heart Rhythm. 3: 948-956.
Liu WP, et al. (2005) Enantioselectivity in environmental safety of current chiral insecticides. Proc Natl Acad Sci US A. 102: 701-706.
Lochter AJ, et al. (1995) Control of neuronal morphology in vitro: interplay between adhesive substrate forces and molecular instruction. J Neurosci Res. 42:145-158.
Long C, et al. (2012) Design optimization of liquid-phase flow patterns for microfabricated lung on a chip. Ann Biomed Eng. 40: 1255-1267.
Lou XJ. (2009) Polarization fatigue in ferroelectric thin films and related materials. Journal of Applied Physics. 105: 024101-024124.
Lou XJ. (2009b) Statistical switching kinetics of ferroelectrics. J Phys Condens Matter. 21(1):012207.
Love S. (2003) Neuronal expression of cell cycle-related proteins after brain ischaemia in man. Neurosci Lett. 353: 29-32.
Lu B, et al. (1996) Expression of synapsin 1 correlates with maturation of the neuromuscular synapse. Neuroscience. 74: 1087-1097.
Lu HR, et al. (2006) In-vitro experimental models for the risk assessment of antibiotic-induced QT prolongation. Eur J Pharmacol. 553: 229-239.
Ludwig T and A Thomson J. (2007) Defined, feeder-independent medium for human embryonic stem cell culture. Curr Protoc Stem Cell Biol. Chapter 1: Unit IC.2.
Lund AE and Narahashi T. (1982) Dose-dependent interaction of the pyrethroid isomers with sodium channels of squid axon membranes. Neurotoxicology. 3: 11-24.
Luo Y, et al. (2006) Effects of growth factors on extracellular matrix production by vocal fold fibroblasts in 3-dimensional culture. Tissue Eng. 12: 3365-3374.
Lyles JM, et al. (1992) Matrigel enhances myotube development in a serum-free defined medium. Intl Dev Neurosci. 10: 59-73.
Ma W, et al. (1998) Neuronal and glial epitopes and transmitter-synthesizing enzymes appear in parallel with membrane excitability during neuroblastoma x glioma hybrid differentiation. Brain Res Dev Brain Res. 106: 155-163.
Machida S, et al. (2004) Primary rat muscle progenitor cells have decreased proliferation and myotube formation during passages. Cell Prolif. 37: 267-277.
Maduell F. (2005) Hemodiafiltration. Hemodial Int. 9: 47-55.
Mahler GJ, et al. (2009a) Characterization of a gastrointestinal tract microscale cell culture analog used to predict drug toxicity. Biotechnol Bioeng. 104: 193-205.
Mahler GJ, et al. (2009b) Characterization of Caco-2 and HT29-MTX cocultures in an in vitro digestion/cell culture model used to predict iron bioavailability. J Nutr Biochem. 20: 494-50.
Malerba A, et al. (2009) Selection of multipotent cells and enhanced muscle reconstruction by myogenic macrophage-secreted factors. Exp Cell Res. 315:915-927.
Malm C, et al. (2004) Leukocytes, cytokines, growth factors and hormones in human skeletal muscle and blood after uphill or downhill running. J Physiol. 556:983-1000.
Malo N, et al. (2006) Statistical practice in high-throughput screening data analysis. Nat Biotechnol. 24: 167-175.
Marhl M, et al. (2000) Complex calcium oscillations and the role of mitochondria and cytosolic proteins. Biosystems. 57: 75-86.
Marona HRN, et al. (1999) Determination of sparfloxacin and its degradation products by HPLC-PDA. J Antimicrob Chemother. 44: 301-302.
Marques MJ and Neto HS. (1997) Ciliary neurotrophic factor stimulates in vivo myotube formation in mice. Neurosci Lett. 234: 43-46.
Mars T, et al. (2001) Differentiation of glial cells and motor neurons during the formation of neuromuscular junctions in cocultures of rat spinal cord explant and human muscle. J Comp Neurol. 438: 239-251.
Mars T, et al. (2003) Functional innervation of cultured human skeletal muscle proceeds by two modes with regard to agrin effects. Neuroscience. 118: 87-97.
Martin-Caraballo M and Greer JJ. (2000) Development of potassium conductances in perinatal rat phrenic motoneurons. J Neurophysiol. 83: 3497-3508.
Martinou JC, et al. (1992) Cholinergic differentiation factor (CDF/LIF) promotes survival of isolated rat embryonic motoneurons in vitro. Neuron. 8: 737-744.
Masu Y, et al. (1993) Disruption of the CNTF gene results in motor neuron degeneration. Nature. 365: 27-32.
Matsakas A and Patel K. (2009) Skeletal muscle fibre plasticity in response to selected environmental and physiological stimuli. Histol Histopathol. 24: 611-629.
Matsuda T, et al. (1992) Two-dimensional cell manipulation technology. An artificial neural circuit based on surface microphotoprocessing. ASAIO J. 38:M243-M247.
Matthews PB. (1964) Muscle spindles and their motor control. Physiol Rev. 44:219-288.
Mattson MP, et al. (1992) Beta-Amyloid Peptides Destabilize Calcium Homeostasis and Render Human Cortical-Neurons Vulnerable to Excitotoxicity. J Neurosci. 12: 376-389.

(56) References Cited

OTHER PUBLICATIONS

Matzno S, et al. (2003) Evaluation of the synergistic adverse effects of concomitant therapy with statins and fibrates on rhabdomyolysis. J Pharm Pharmacol. 55: 795-802.
Maves L, et al. (2007) Pbx homeodomain proteins direct Myod activity to promote fast-muscle differentiation. Development. 134: 3371-3382.
Maynard EM. (2001) Visual prostheses. Annu Rev Biomed Eng. 3: 145-168.
McAuliffe GJ, et al. (2008) Development of a gastrointestinal tract microscale cell culture analog to predict drug transport. Mol Cell Biomech. 5: 119-132.
McBeath R, et al. (2004) Cell shape, cytoskeletal tension, and RhoA regulate stem cell lineage commitment. Dev Cell. 6: 483-495.
McDevitt TC, et al. (2002) In vitro generation of differentiated cardiac myofibers on micropatterned laminin surfaces. J Biomed Mater Res. 60: 472-479.
McMahon JA, et al. (1998) Noggin-mediated antagonism of BMP signaling is required for growth and patterning of the neural tube and somite. Genes Dev. 12:1438-1452.
Megeney LA, et al. (1996) bFGF and LIF signaling activates STAT3 in proliferating myoblasts. Dev Genet. 19: 139-145.
Mehra S, et al. (2004) A boolean algorithm for reconstructing the structure of regulatory networks. Metab Eng. 6: 326-339.
Meijer L and Raymond E. (2003) Roscovitine and other purines as kinase inhibitors. From starfish oocytes to clinical trials. Ace Chem Res. 36: 417-425.
Melendez-Vasquez CV, et al. (2001) Nodes of Ranvier form in association with ezrin-radixin-moesin (ERM)-positive Schwann cell processes. Proc Natl Acad Sci US A. 98: 1235-1240.
Mendelsohn JD, et al. (2003) Rational design of cytophilic and cytophobic polyelectrolyte multilayer thin films. Biomacromolecules. 2003 4: 96-106.
Menendez L, et al. (2011) Wnt signaling and a Smad pathway blockade direct the differentiation of human pluripotent stem cells to multipotent neural crest cells. Proc Natl Acad Sci US A. 108: 19240-19245.
Menn B, et al. (2010) Delayed treatment with systemic (S)-roscovitine provides neuroprotection and inhibits in vivo CDK5 activity increase in animal stroke models. PLoS One. 5: e1211.
Metzger SW, et al. (1999) Development and characterization of surface chemistries for microfabricated biosensors. J of Vacuum Sci & Tech a-Vacuum Surfaces and Films. 17: 2623-2628.
Meyer G and Nabil MA. (1988) Novel optical approach to atomic force microscopy. Applied Physics Letters. 53: 1045-1047.
Meyer T, et al. (2004a) Micro-electrode arrays in cardiac safety pharmacology—A novel tool to study QT interval prolongation. Drug Saf. 27: 763-772.
Meyer T, et al. (2004b) QT-screen: high-throughput cardiac safety pharmacology by extracellular electrophysiology on primary cardiac myocytes. Assay Drug Dev Technol. 2: 507-514.
Miles GB, et al. (2004) Functional properties of motoneurons derived from mouse embryonic stem cells. J Neurosci. 24: 7848-7858.
Miller FD. (2007) Riding the waves: neural and nonneural ongms for mesenchymal stem cells. Cell Stem Cell. 1: 129-130.
Miller SC, et al. (1988) Tumor necrosis factor inhibits human myogenesis in vitro. Mol Cell Biol. 8: 2295-2301.
Mitsumoto H, et al. (2001) Effects of cardiotrophin-1 (CT-1) in a mouse motor neuron disease. Muscle Nerve. 24: 769-777.
Mizuseki K, et al. (2003) Generation of neural crest-derived peripheral neurons and floor plate cells from mouse and primate embryonic stem cells. Proc Natl Acad Sci US A. 100: 5828-5833.
Moe GK. (1962) On the multiple wavelet hypothesis of atrial fibrillation. Arch Int Pharmacodyn Ther. 183-188.
Mohammed JS, et al. (2004) Micropatterning of nanoengineered surfaces to study neuronal cell attachment in vitro. Biomacromolecules. 5: 1745-1755.

Mohan DK, et al. (2006) Toxin detection based on action potential shape analysis using a realistic mathematical model of differentiated NG 108-15 cells. Biosens Bioelectron. 21: 1804-1811.
Mokry J, et al. (2007) Differentiation of neural stem cells into cells of oligodendroglial lineage. Acta Medica (Hradec Kralove). 50: 35-41.
Molnar P, et al. (2007) Photolithographic Patterning of C2C12 Myotubes using Vitronectin as Growth Substrate in Serum-Free Medium. Biotechnol Prog. 23:265-268.
Molnar P, et al. (2007b) Synaptic connectivity in engineered neuronal networks. Methods Mol Biol. 403: 165-173.
Molnar P, et al. (2007c) Modeling of action potential generation in NG 108-15 cells. Methods Mol Biol. 403: 175-184.
Monaco EA 3rd and Vallano ML. (2005) Roscovitine triggers excitotoxicity in cultured granule neurons by enhancing glutamate release. Mol Pharmacol. 68:1331-1342.
Monaco EA 3rd. (2004) Recent evidence regarding a role for Cdk5 dysregulation in Alzheimer's disease. Curr Alzheimer Res. 1: 33-38.
Monyer H, et al. (1994) Developmental and regional expression in the rat brain and functional properties of four NMDA receptors. Neuron. 12: 529-540.
Moore JW, et al. (1991) The mRNAs encoding acidic FGF, basic FGF and FGF receptor are coordinately downregulated during myogemc differentiation. Development. 111: 741-748.
Morefield SI, et al. (2000) Drug evaluations using neuronal networks cultured on microelectrode arrays. Biosens Bioelectron. 15: 383-396.
Morimoto, S., & Masuda, M. (1984). Dependence of conduction velocity on spike interval during voluntary muscular contraction in human motor units. European journal of applied physiology and occupational physiology, 53(3), 191-195.
Morin F, et al. (2006) Constraining the connectivity of neuronal networks cultured on microelectrode arrays with microfluidic techniques: a step towards neuron-based functional chips. Biosens Bioelectron. 21: 1093-1100.
Morrow NG, et al. (1990) Increased expression of fibroblast growth factors in a rabbit skeletal muscle model of exercise conditioning. J Clin Invest. 85: 1816-1820.
Motamed K, et al. (2003) Fibroblast growth factor receptor-I mediates the inhibition of endothelial cell proliferation and the promotion of skeletal myoblast differentiation by SPARC: a role for protein kinase A. J Cell Biochem. 90: 408-423.
Moulard G, et al. (1998) Improvement of the cantilever beam technique for stress measurement during the physical vapor deposition process. J Vac Science Technol A. 16(2): 736-742.
Mousavi K, et al. (2004) BDNF rescues myosin heavy chain IIB muscle fibers after neonatal nerve injury. Am J Physiol Cell Physiol. 287: C22-C29.
Mrksich M. (2000) A surface chemistry approach to studying cell adhesion. Biosensors & Bioelectronics. 29: 267-273.
Mufti NA and Shuler ML. (1998) Different In Vitro Systems Affect CYPIAI Activity in Response to 2,3,7,8-Tetrachlorodibenzo-p-dioxin. Toxicol In Vitro. 12: 259-272.
Mulkey D, et al. (2003) Hyperbaric oxygen and chemical oxidants stimulate CO2/H+-sensitive neurons in rat brain stem slices. J Appl Physiol. 95: 910-92.
Mullen RJ, et al. (1992) NeuN, a neuronal specific nuclear protein in vertebrates. Development. 116: 201-211.
Muller FJ, et al. (2006) Gene therapy: can neural stem cells deliver? Nat Rev Neurosci. 7: 75-84.
Muller P and Saul A. (2004) Elastic effects on surface physics. Surface Science Reports. 54: 157-258.
Muller T, et al. (1999) A 3-D microelectrode system for handling and caging single cells and particles. Biosens Bioelectron. 14: 247-256.
Munaron L. (2002) Calcium signalling and control of cell proliferation by tyrosine kinase receptors (review). Int J Mol Med. 10: 671-676.
Munsterberg AE, et al. (1995) Combinatorial signaling by Sonic hedgehog and Wnt family members induces myogenic bHLH gene expression in the somite. Genes Dev. 9: 2911-2922.

(56) References Cited

OTHER PUBLICATIONS

Muraki K, et al. (1994) Effects of noradrenaline on membrane currents and action potential shape in smooth muscle cells from guinea-pig ureter. J Physiol. 481:617-627.
Murgia M, et al. (2000) Ras is involved in nerve-activity-dependent regulation of muscle genes. Nat Cell Biol. 2: 142-147.
Murphy M, et al. (1994) FGF2 regulates proliferation of neural crest cells, with subsequent neuronal differentiation regulated by LIF or related factors. Development. 120: 3519-3528.
Mutyala MSK, et al. (2009) Mechanical and electronic approaches to improve the sensitivity of microcantilever sensors. Acta Mechanica Sinica. 25: 1-12.
Nagy Z, et al. (1997) Cell cycle markers in the hippocampus in Alzheimer's disease. Acta Neuropathol. 94: 6-15.
Nakamura S, et al. (2010) Analysis of cardiac toxicity caused by cyclophosphamide in the H9c2 cell line and isolated and perfused rat hearts. Gan To Kagaku Ryoho. 37: 677-680. Abstract only in English.
Nakamura Y, et al. (2007) The in vitro metabolism of a pyrethroid insecticide, permethrin, and its hydrolysis products in rats. Toxicology. 235: 176-184.
Nam Y, et al. (2006) Neural recording and stimulation of dissociated hippocampal cultures using microfabricated three-dimensional tip electrode array. J Neurosci Methods. 155: 296-299.
Nash MP, et al. (2006) Evidence for multiple mechanisms in human ventricular fibrillation. Circulation. 114: 536-542.
Nash, M. P., & Panfilov, A. V. (2004). Electromechanical model of excitable tissue to study reentrant cardiac arrhythmias. Progress in biophysics and molecular biology, 85(2), 501-522.
Nat R. (2011) Cortical network from human embryonic stem cells. J Cell Mol Med. 15: 1429-1431.
Natarajan A, et al. (2006) Microelectrode array recordings of cardiac action potentials as a high throughput method to evaluate pesticide toxicity. Toxicol In Vitro. 20: 375-381.
Natarajan A, et al. (2008) Growth and electrophysiological properties of rat embryonic cardiomyocytes on hydroxyl- and carboxyl-modified surfaces. J Biomater Sci Polym Ed. 19: 1319-1331.
Natarajan A, et al. (2011) Patterned cardiomyocytes on microelectrode arrays as a functional, high information content drug screening platform. Biomaterials. 32:4267-4274.
Natarajan A, et al. (2013) Engineered In Vitro Feed-Forward Networks. J Biotechnol Biomater. 3:153.
Natarajan AR, et al. (2004) Intrinsic cardiac catecholamines help maintain beating activity in neonatal rat cardiomyocyte cultures. Pediatr Res. 56: 411-417.
Nazaret C, et al. (2009) Mitochondrial energetic metabolism: a simplified model of TCA cycle with ATP production. J Theor Biol. 258: 455-464.
Nelson CE, et al. (1996) Analysis of Hox gene expression in the chick limb bud. Development. 122: 1449-1466.
Nelson CM and Bisell MJ. (2006) Of extracellular matrix, scaffolds, and signaling: tissue architecture regulates development, homeostasis, and cancer. Annu Rev Cell Dev Biol. 22: 287-309.
Nelson PG, et al. (1993) Synapse elimination from the mouse neuromuscular junction in vitro: a non-Hebbian activity-dependent process. J Neurobiol. 24:1517-1530.
Nelson PG. (1975) Nerve and muscle cells in culture. Physiol Rev. 55: 1-61.
Nerbonne JM and Kass RS. (2005) Molecular physiology of cardiac repolarization. Physiol Rev. 85: 1205-1253.
Nguemo F, et al. (2012) In vitro model for assessing arrhythmogenic properties of drugs based on high-resolution impedance measurements. Cell Physiol Biochem. 29: 819-832.
Nguyen L, et al. (2006) The Yin and Yang of cell cycle progression and differentiation in the oligodendroglial lineage. Ment Retard Dev Disabil Res Rev. 12: 85-96.
Nicolelis MAL and Ribeiro S. (2002) Multielectrode recordings: the next steps. Curr Opin Neurobiol. 12: 602-606.
Nimmrich V, et al. (2008) Amyloid beta oligomers (A beta(I-42) globulomer) suppress spontaneous synaptic activity by inhibition of P/Q-type calcium currents. J Neurosci. 28: 788-797.
Nishikawa J, et al. (2005) Increase of Cardiotrophin-1 immunoreactivity in regenerating and overloaded but not denervated muscles of rats. Neuropathology. 25: 54-65.
Nishimaru H, et al. (2005) Mammalian motor neurons corelease glutamate and acetylcholine at central synapses. Proc Natl Acad Sci US A. 102: 5245-5249.
Nistor GI, et al. (2005) Human embryonic stem cells differentiate into oligodendrocytes in high purity and myelinate after spinal cord transplantation. Glia. 49: 385-396.
Noble D. (2004) Modeling the heart. Physiology (Bethesda). 19: 191-197.
Noll E and Miller RH. (1993) Oligodendrocyte precursors originate at the ventral ventricular zone dorsal to the ventral midline region in the embryonic rat spinal cord. Development. 118: 563-573.
Normann RA, et al. (1999) A neural interface for a cortical vision prosthesis. Vision Res. 39: 2577-2587.
Norris W, et al. (2000) Slow muscle induction by Hedgehog signalling in vitro. J Cell Sci. 113: 2695-2703.
Nugaeva, N, et al. (2005). Micromechanical cantilever array sensors for selective fungal immobilization and fast growth detection. Biosensors and Bioelectronics, 21(6), 849-856.
Nyitrai G, et al. (2006) Extracellular level of GABA and Glu: III VIVO microdialysis-HPLC measurements. Curr Top Med Chem. 6: 935-940.
Oakley RA, et al. (1997) Neurotrophin-3 promotes the differentiation of muscle spindle afferents in the absence of peripheral targets. J Neurosci. 17: 4262-4274.
O'Connor SM, et al. (2000) Immobilization of neural cells in three-dimensional matrices for biosensor applications. Biosens Bioelectron. 14: 871-881.
Offenhausser A and Knoll W. (2001) Cell-transistor hybrid systems and their potential applications. Trends Biotechnol. 19: 62-66.
Offenhausser A, et al. (1997) Field-effect transistor array for monitoring electrical activity from mammalian neurons in culture. Biosensors and Bioelectronics. 12: 819-826.
Oh TI, et al. (2007) Real-time fluorescence detection of multiple microscale cell culture analog devices in situ. Cytometry A. 71: 857-865.
Oliver L, et al. (1992) Acidic fibroblast growth factor (aFGF) in developing normal and dystrophic (mdx) mouse muscles. Distribution in degenerating and regenerating mdx myofibres. Growth Factors. 7: 97-106.
Olson E. (1992a) Activation of muscle-specific transcription by myogenic helixloop-helix proteins. Symp Soc Exp Biol. 46: 331-341.
Olson EN and Perry WM. (1992b) MyoD and the paradoxes of myogenesis. Curr Biol. 2: 35-37.
Olson EN and Williams RS. (2000) Calcineurin Signaling and Muscle Remodeling. Cell. 101: 689-692.
Olson EN. (1992c) Interplay between proliferation and differentiation within the myogenic lineage. Dev Biol. 154: 261-272.
Olwin BB and Rapraeger A. (1992) Repression of myogenic differentiation by aFGF, bFGF, and K-FGF is dependent on cellular heparan sulfate. J Cell Biol. 118: 631-639.
Oppenheim RW, et al. (1991) Control of embryonic motoneuron survival in vivo by ciliary neurotrophic factor. Science. 251: 1616-1618.
Oppenheim RW, et al. (2001) Cardiotrophin-1, a muscle-derived cytokine, is required for the survival of subpopulations of developing motoneurons. J Neurosci. 21: 1283-1291.
Orentas DM and Miller RH. (1999) Regulation of oligodendrocyte development. Mol Neurobiol. 18: 247-259.
Orlov SN and Hamet P. (2006) Intracellular monovalent ions as second messengers. J Membr Biol. 210: 161-172.
Ostuni E, et al. (2000) Patterning mammalian cells using elastomeric membranes. Langmuir. 16: 7811-7819.
Oumata N, et al. (2008) Roscovitine-derived, dual-specificity inhibitors of cyclindependent kinases and casein kinases 1. J Med Chem. 51: 5229-5242.

(56) References Cited

OTHER PUBLICATIONS

Padmanabhan J, et al. (1999) Role of cell cycle regulatory proteins in cerebellar granule neuron apoptosis. J Neurosci. 19: 8747-8756.
Pagan SM, et al. (1996) Surgical removal of limb bud Sonic hedgehog results in posterior skeletal defects. Dev Biol. 180: 35-40.
Pancrazio JJ, et al. (1998) Portable cell-based biosensor system for toxin detection. Sensors and Actuators B Chem. 53: 179-185.
Park J, et al. (2005) Real-time measurement of the contractile forces of self-organized cardiomyocytes on hybrid biopolymer microcantilevers. Anal Chem. 77: 6571-6580.
Park, TH et al. (2003) Integration of Cell Culture and Microfabrication Technology. Biotechnol. Prog. 19: 243-253.
Parker KK, et al. (2008) Myofibrillar architecture m engineered cardiac myocytes. Circ Res. 103: 340-342.
Parng C, et al. (2002) Zebrafish: A Preclinical Model for Drug Screening. Assay Drug Dev Technol. 1: 41-48.
Parviz M and Gross GW. (2007) Quantification of zinc toxicity using neuronal networks on microelectrode arrays. Neurotoxicolo12:v. 28: 520-531.
Paspalas CD and Papadopoulos GC. (1996) Ultrastructural relationships between noradrenergic nerve fibers and non-neuronal elements in the rat cerebral cortex. Glia. 17: 133-146.
Payne ET, et al. (2006) Nutritional therapy improves function and complements corticosteroid intervention in mdx mice. Muscle Nerve. 33: 66-77.
Peng HB, et al. (2003) Differential effects of neurotrophins and schwann cell-derived signals on neuronal survival/growth and synaptogenesis. J Neurosci. 23:5050-5060.
Peroulakis ME and Forger NG. (2000) Ciliary neurotrophic factor increases muscle fiber number in the developing levator ani muscle of female rats. Neurosci Lett. 296: 73-76.
Perrier AL, et al. (2004) Derivation of midbrain dopamine neurons from human embryonic stem cells. Proc Natl Acad Sci USA. 101: 12543-12548.
Peters A. (1964) Observations on the Connexions Between A709. Myelin Sheaths and Glial Cells in the Optic Nerves of Young Rats. J Anat. 98: 125-134.
Peterson CA, et al. (1999) Effects of moisture on Fowler-Nordheim characterization of thin silicon-oxide films. J Vac Science Technol A. 17: 2753-2758.
Pette D and Staron S. (2001) Transitions of muscle fiber phenotypic profiles. Histochem and Cell Biol. 115: 359-372.
Pette D, et al. (2002) Partial fast-to-slow conversion of regenerating rat fast-twithc muscle by chronic low frequency stimulation. J Muscle Res Cell Motil. 3:215-221.
Pfeiffer SE, et al. (1993) The oligodendrocyte and its many cellular processes. Trends Cell Biol. 3: 191-197.
Pfrieger FW and Barres BA. (1997) Synaptic efficacy enhanced by glial cells in vitro. Science. 277: 1684-1687.
Pijnappels DA, et al. (2007) Resynchronization of separated rat cardiomyocyte fields with genetically modified human ventricular scar fibroblasts. Circulation. 116: 2018-2028.
Pillekamp F, et al. (2012) Contractile properties of early human embryonic stem cell-derived cardiomyocytes: beta-adrenergic stimulation induces positive chronotropy and lusitropy but not inotronv. Stem Cells Dev. 21: 2111-2121.
Podratz J, et al. (2004) Antioxidants are necessary for myelination of dorsal root ganglion neurons, in vitro. Glia. 45: 54-58.
Pomp O, et al. (2005) Generation of peripheral sensory and sympathetic neurons and neural crest cells from human embryonic stem cells. Stem Cells. 23: 923-930.
Pomp O, et al. (2008) PA6-induced human embryonic stem cell-derived neurospheres: a new source of human peripheral sensory neurons and neural crest cells. Brain Res. 1230: 50-60.
Pontier C, et al. (2001) HT29-MTX and Caco-2/TC7 monolayers as predictive models for human intestinal absorption: role of the mucus layer. J Pharm Sci. 90:1608-1619.
Popat KC, et al. (2004) Surface modification of nanoporous alumina surfaces with poly(ethylene glycol). Langmuir. 20: 8035-8041.
Popat KC, et al. (2004b) Quantitative xps analysis of peg-modified silicon surfaces. J Phys Chem. 108: 5185-5188.
Porto F, et al. (2008) Towards a Scientific Model Management System. ER Workshops 2008. NCS 5232: 55-65.
Pouton CW and Haynes JM. (2005) Pharmaceutical applications of embryonic stem cells. Adv Drug Deliv Rev. 57: 1918-1934.
Powell C, et al. (1999) Tissue engineered human bioartificial muscles expressing a foreign recombinant protein for gene therapy. Hum Gene Ther. 10: 565-577.
Powell C, et al. (2002) Mechanical stimulation improves tissue-engineered human skeletal muscle. Am J Physiol Cell Physiol. 283: C1557-C1565.
Price PJ and Brewer GJ. (2001) Serum-Free Media for Neural Cell Cultures. Protocols for Neural Cell Cultures, 3rd Ed, Humana Press Inc., Totowa, NJ, Chapter 19, 255-264.
Pringle NP, et al. (1996) Determination of neuroepithelial cell fate: induction of the oligodendrocyte lineage by ventral midline cells and sonic hedgehog. Dev Biol. 177: 30-42.
Quinn LS, et al. (1990) Paracrine control of myoblast proliferation and differentiation by fibroblasts. Dev Biol. 140: 8-19.
Raible DW and McMorris FA. (1989) Cyclic AMP regulates the rate of differentiation of oligodendrocytes without changing the lineage commitment of their progenitors. Dev Biol. 133: 437-446.
Raible DW and Mc Morris FA. (1990) Induction of oligodendrocyte differentiation by activators of adenylate cyclase. J Neurosci Res. 27: 43-46.
Raiteri R, et al. (2001) Micromechanical cantilever-based biosensors. Sensors and Actuators B—Chemical. 79: 115-126.
Rajnicek AM, et al. (1997) Contact guidance of CNS neurites on grooved quartz: influence of groove dimensions, neuronal age and cell type. J Cell Sci. 110: 2905-2913.
Raley-Susman KM, et al. (1991) Regulation of intracellular pH in cultured hippocampal neurons by an amiloride-insensitive Na+/H+ exchanger. J Biol Chem. 266: 2739-2745.
Rampe D, et al. (1997) A mechanism for the proarrhythmic effects of cisapride (Propulsid): high affinity blockade of the human cardiac potassium channel HERG. FEBS Lett. 417: 28-32.
Ravenscroft MS, et al. (1998) Developmental Neurobiology Implications from Fabrication and Analysis of Hippocampal Neuronal Networks on Patterned Silane-Modified Surfaces. J Am Chem Soc. 120: 12169-12177.
Ravenscroft-Chang MS, et al. (2010) Altered calcium dynamics in cardiac cells grown on silane-modified surfaces. Biomaterials. 31: 602-607.
Recanatini M, et al. (2005) QT prolongation through hERG K(+) channel blockade: current knowledge and strategies for the early prediction during drug development. Med Res Rev. 25: 133-166.
Rekling JC, et al. (2000) Synaptic control of motoneuronal excitability. Physiol Rev. 80: 767-852.
Reppel M, et al. (2004) Beta-adrenergic and muscarinic modulation of human embryonic stem cell-derived cardiomyocytes. Cell Physiol Biochem. 14: 187-196.
Reppel M, et al. (2005) The electrocardiogram of human embryonic stem cell-derived cardiomyocytes. J Electrocardiol. 38: 166-170.
Reppel M, et al. (2007) Effect of cardioactive drugs on action potential generation and propagation in embryonic stem cell-derived cardiomyocytes. Cell Physiol Biochem. 19: 213-224.
Revzin A, et al. (2003) Surface Engineering with Poly( ethylene glycol) Photolithography to Create High-Density Cell Arrays on Glass. Langmuir. 19:9855-9862.
Reyes D, et al. (2004) Micropatteming neuronal cells on polyelectrolyte multilayers. Langmuir. 20: 8805-8811.
Richards S, et al. (2008) Development of defined media for the serum-free expansion of primary keratinocytes and human embryonic stem cells. Tissue Eng Part C Methods. 14: 221-232.
Richert L, et al. (2004) pH dependent growth of poly(L-lysine )/poly(L-glutamic) acid multilayer films and their cell adhesion properties. Surface Science. 570: 13-29.
Riley M. (1993) Functions of the gene products of *Escherichia coli*. Microbiol Rev. 57: 862-952.
Robertson TA, et al. (2000) Comparison of astrocytic and myocytic metabolic dysregulation m apolipoprotein E deficient and human apolipoprotein E transgenic mice. Neuroscience. 98: 353-359.

(56) References Cited

OTHER PUBLICATIONS

Rodan SB, et al. (1989) Effects of acidic and basic fibroblast growth factors on osteoblastic cells. Connect Tissue Res. 20: 283-288.
Roden DM, et al. (2002) Cardiac ion channels. Annu Rev Physiol. 64: 431-475.
Rogister B, et al. (1999) From neural stem cells to myelinating oligodendrocytes. Mol Cell Neurosci. 14: 287-300.
Rohr S, et al. (1991) Patterned growth of neonatal rat heart cells in culture. Morphological and electrophysiological characterization. Circ Res. 68: 114-130.
Rosati B and McKinnon D. (2004) Regulation of ion channel expression. Circ Res. 94: 874-883.
Rosenberg SS, et al. (2008) The geometric and spatial constraints of the microenvironment induce oligodendrocyte differentiation. Proc Natl Acad Sci USA. 105: 14662-14667.
Rumsey JW, et al. (2008) Tissue Engineering Intrafusal Fibers: Dose and Time Dependent Differentiation of Nuclear Bag Fibers in a Defined In Vitro System using Neuregulin 1-beta-I. Biomaterials. 29: 994-1004.
Rumsey JW, et al. (2009) Node of Ranvier formation on motoneurons in vitro. Biomaterials. 30: 3567-3572.
Rumsey JW, et al. (2010) Tissue engineering the mechanosensory circuit of the stretch reflex arc: sensory neuron innervation of intrafusal muscle fibers. Biomaterials. 31: 8218-8227.
Rutten WLC. (2002) Selective electrical interfaces with the nervous system. Annu Rev Biomed Eng. 4: 407-452.
Sakuma K, et al. (2000) Differential adaptation of growth and differentiation factor 8/myostatin, fibroblast growth factor 6 and leukemia inhibitory factor in overloaded, regenerating and denervated rat muscles. Biochim Biophys Acta. 1497: 77-88.
Sala M, et al. (2009) Electrophysiological changes of cardiac function during antidepressant treatment. Ther Adv Cardiovasc Dis. 3: 29-43.
Sander D, et al. (1995) A simple technique to measure stress in ultrathin films during growth. Rev Sci Instrum. 66: 4734.
Sanes JR and Lichtman JW. (1999) Development of the vertebrate neuromuscular junction. Annu Rev Neurosci. 22: 389-442.
Sanes JR and Lichtman JW. (2001) Induction, assembly, maturation and maintenance of a postsynaptic apparatus. Nat Rev Neurosci. 2: 791-805.
Sanes JR. (1997) Genetic analysis of postsynaptic differentiation at the vertebrate neuromuscular junction. Curr Opin Neurobiol. 7: 93-100.
Sasahara K, et al. (2007) Mode of action and functional significance of estrogen-inducing dendritic growth, spinogenesis, and synaptogenesis in the developing Purkinje cell. JNeurosci. 27: 7408-7417.
Sathaye A, et al. (2006) Electrical pacing counteracts intrinsic shortening of action potential duration of neonatal rat ventricular cells in culture. J Mol Cell Cardiol. 41: 633-64.
Scaal M, et al. (1999) SF/HGF is a mediator between limb patterning and muscle development. Development. 126: 4885-4893.
Schaffner AE, et al. (1995) Investigation of the factors necessary for growth of hippocampal neurons in a defined system. J Neurosci Methods. 62: 111-11.
Scherer J, et al. (1995) Differentiation and maturation of rabbit retinal oligodendrocyte precursor cells in vitro. Brain Res Dev Brain Res. 89: 214-226.
Schiaffino S and Serrano A. (2002) Calcineurin signaling and neural control of skeletal muscle fiber type and size. Trends Pharmacol Sci. 23: 569-575.
Schiaffino S, et al. (2007) Activity-Dependent Signaling Pathways Controlling Muscle Diversity and Plasticity. Physiology. 22: 269-278.
Schluter H and Kaur P. (2009) Bioengineered human skin from embryonic stem cells. Lancet. 374: 1725-1726.
Schneider A, et al. (2006) Glycated polyelectrolyte multilayer films: differential adhesion of primary versus tumor cells. Biomacromolecules. 7: 2882-2889.
Schneider AG, et al. (1999) Muscle LIM protein: expressed in slow muscle and indcued in fast muscle by enhanced contractile activity. Am J Physiol. 276:C900-C906.
Scholzen T and Gerdes J. (2000) The Ki-67 protein: from the known and the unknown. J Cell Physiol. 182: 311-322.
Schulz TC, et al. (2004) Differentiation of human embryonic stem cells to dopaminergic neurons in serum-free suspension culture. Stem Cells. 22: 1218-1238.
Schuster D, et al. (2005) Why drugs fail—a study on side effects in new chemical entities. Curr Pharm Des. 11: 3545-3559.
Schuster Rand Holzhutter HG. (1995) Use of mathematical models for predicting the metabolic effect of large-scale enzyme activity alterations. Application to enzyme deficiencies ofred blood cells. Eur J Biochem. 229: 403-418.
Schwab ME. (2002) Repairing the injured spinal cord. Science. 295: 1029-1031.
Schwarz JJ, et al. (1992) The basic region of myogenin cooperates with two transcription activation domains to induce muscle-specific transcription. Mol Cell Biol. 12: 266-275.
Scollon EJ, et al. (2009) In vitro metabolism of pyrethroid pesticides by rat and human hepatic microsomes and cytochrome p450 isoforms. Drug Metab Dispos. 37: 221-228.
Scoote Mand Williams AJ. (2004) Myocardial calcium signalling and arrhythmia pathogenesis. Biochem Biophys Res Commun. 322: 1286-1309.
Scott W, et al. (2001) Human Skeletal Muscle Fiber Type Classifications. Phys Ther. 81: 1810-1816.
Selivanov VA, et al. (2004) Nucleotide-gated KA TP channels integrated with creatine and adenylate kinases: amplification, tuning and sensing of energetic signals in the compartmentalized cellular environment. Mol Cell Biochem. 256-257: 243-256.
Selivanova OM, et al. (2003) Compact globular structure of Thermus thermophilus ribosomal protein S 1 in solution: sedimentation and calorimetric study. J Biol Chem. 278: 36311-36314.
Semsarian C, et al. (1999) Skeletal muscle hypertrophy is mediated by a Ca2+ dependent calcineurin signalling pathway. Nature. 400: 576-581.
Sghirlanzoni A, et al. (2005) Sensory neuron diseases. Lancet Neurol. 4: 349-361.
Shah NM, et al. (1996) Alternative neural crest cell fates are instructively promoted by TGFbeta superfamily members. Cell. 85: 331-343.
Shainberg A, et al. (1976) Induction of acetylcholine receptors in muscle cultures. Pflugers Arch. 361: 255-261.
Shankar GM, et al. (2008) Amyloid-beta protein dimers isolated directly from Alzheimer's brains impair synaptic plasticity and memory. Nat Med. 14:837-842.
Shansky J, et al. (1997) A simplified method for tissue engineering skeletal muscle organoids in vitro. In Vitro Cell Dev Biol Anim. 33: 659-661.
Shansky J, et al. (2006a) Paracrine release of insulin-like growth factor 1 from a bioengineered tissue stimulates skeletal muscle growth in vitro. Tissue Eng. 12:1833-1841.
Shansky J, et al. (2006b) Tissue engineering human skeletal muscle for clinical applications. Culture of Cells for Tissue Engineering. 239-257.
Sheikh SI and Amato AA. (2010) The dorsal root ganglion under attack: the acquired sensory ganglionopathies. Pract Neurol. 10: 326-334.
Sheng Z, et al. (1996) Cardiotrophin-1 displays early expression in the murine heart tube and promotes cardiac myocyte survival. Development. 122: 419-428.
Sheridan DC, et al. (2003a) Ca2+-dependent excitation-contraction coupling triggered by the heterologous cardiac/brain DHPR beta2a-subunit in skeletal myotubes. Biophys J. 85: 3739-3757.
Sheridan DC, et al. (2003b) Truncation of the carboxyl terminus of the dihydropyridine receptor beta1a subunit promotes Ca2+ dependent excitation-contraction coupling in skeletal myotubes. Biophys J. 84: 220-237.
Sherman DL and Brophy PJ. (2005a) Mechanisms of axon ensheathment and myelin growth. Nat Rev Neurosci. 6: 683-690.
Sherman DL, et al. (2005b) Neurofascins are required to establish axonal domains for saltatory conduction. Neuron. 48: 737-742.

(56) References Cited

OTHER PUBLICATIONS

Shimono K, et al. (2000) Multielectrode Recording of Rhythmic Oscillations in Brain Slices: A Novel Technique for Screening Psychoactive Drugs. Faseb J. 14:1047.
Shin S, et al. (2005) Human motor neuron differentiation from human embryonic stem cells. Stem Cells Dev. 14: 266-269.
Shuler ML. (2012) Modeling life. Ann Biomed Eng. 40: 1399-1407.
Silver JH, et al. (1999) Surface properties and hemocompatibility of alkyl-siloxane monolayers supported on silicone rubber: effect of alkyl chain length and ionic functionality. Biomaterials. 20: 1533-1543.
Simmons A, et al. (2005) Painful lessons. Nat Rev Drug Discov. 4: 800-803.
Simon M, et al. (2003) Effect of NT-4 and BDNF delivery to damaged sciatic nerves on phenotypic recovery of fast and slow muscles fibres. Eur J Neurosci. 18: 2460-2466.
Simpson ML, et al. (2001) Whole-cell biocomputing. Trends Biotechnol. 19:317-323.
Sin A, et al. (2004) The design and fabrication of three-chamber microscale cell culture analog devices with integrated dissolved oxygen sensors. Biotechnol Prog. 20: 338-345.
Singh RP, et al. (2009) Retentive multipotency of adult dorsal root ganglia stem cells. Cell Transplant. 18: 55-68.
Singhvi R, et al. (1994) Engineering cell shape and function. Science. 264: 696-698.
Slepchenko BM, et al. (2003) Quantitative cell biology with the Virtual Cell. Trends Cell Biol. 13: 570-576.
Smith J and Schofield PN. (1994) The effects of fibroblast growth factors in long-term primary culture of dystrophic (mdx) mouse muscle myoblasts. Exp Cell Res. 210: 86-93.
Smith JR, et al. (2008) Inhibition of Activin/Nodal signaling promotes specification of human embryonic stem cells into neuroectoderm. Dev Biol. 313:107-1.
Smith PF, et al. (1991) HMG-CoA reductase inhibitor-induced myopathy in the rat: cyclosporine A interaction and mechanism studies. J Pharmacol Exp Ther. 257: 1225-1235.
Smolen PD, et al. (2004) Mathematical Modeling and Analysis of Intracellular Signaling Pathways. From Molecules to Networks—An Introduction to Cellular and Molecular Neuroscience. p. 391-430.
Sofia SJ and Merrill EW. (1997) Protein Adsorption on Poly(ethylene oxide)-Grafted Silicon Surfaces. ACS Symposium Series. 680: 342-360.
Song WK, et al. (1992) H36-alpha 7 is a novel integrin alpha chain that is developmentally regulated during skeletal myogenesis. J Cell Biol. 117: 643-657.
Soni AS, et al. (2008) Determination of critical network interactions: an augmented Boolean pseudo-dynamics approach. IET Syst Biol. 2: 55-63.
Soundarapandian MM, et al. (2007) Role of K(ATP) channels in protection against neuronal excitatory insults. J Neurochem. 103: 1721-172.
Soundararajan P, et al. (2007) Easy and rapid differentiation of embryonic stem cells into functional motoneurons using sonic hedgehog-producing cells. Stem Cells. 25: 1697-1706.
Spach MS and Heidlage JF. (1995) The stochastic nature of cardiac propagation at a microscopic level. Electrical description of myocardial architecture and its application to conduction. Circ Res. 76: 366-380.
Spach MS. (1983) The role of cell-to-cell coupling in cardiac conduction disturbances. Adv Exp Med Biol. 161: 61-77.
Spargo BJ, et al. (1994) Spatially controlled adhesion, spreading, and differentiation of endothelial cells on self-assembled molecular monolayers. Proc Natl Acad Sci USA. 91: 11070-11074.
Spencer CI, et al. (2001) Actions of pyrethroid insecticides on sodium currents, action potentials, and contractile rhythm in isolated mammalian ventricular myocytes and perfused hearts. J Pharmacol Exp Ther. 298: 1067-1082.
St John PM, et al. (1997) Preferential glial cell attachment to microcontact printed surfaces. J Neurosci Methods. 75: 171-177.

St. George-Hyslop PH and Petit A. (2004) Molecular biology and genetics of Alzheimer's disease.CR Biol. 328: 119-130.
Stavarachi M, et al. (2010) Spinal muscular atrophy disease: a literature review for therapeutic strategies. J Med Life. 3: 3-9.
Steffen LS, et al. (2007) Zebrafish orthologs of human muscular dystrophy genes. BMC Genomics. 8: 7.
Stenger DA, et al. (1992) Coplanar Molecular Assemblies of Aminoalkylsilane and Perfluorinated Alkylsilane—Characterization and Geometric Definition of Mammalian-Cell Adhesion and Growth. Journal of the American Chemical Society. 114: 8435-8442.
Stenger DA, et al. (1993) Surface determinants of neuronal survival and growth on selfassembled monolayers in culture. Brain Res. 630: 136-147.
Stenger DA, et al. (1998) Microlithographic determination of axonal/dendritic polarity in cultured hippocampal neurons. J Neurosci Methods. 82: 167-173.
Sternberger NH, et al. (1985) Immunocytochemistry of myelin basic proteins in adult rat oligodendroglia. J Neuroimmunol. 7: 355-363.
Stett A, et al. (2003) Biological application of microelectrode arrays in drug discovery and basic research. Anal Bioanal Chem. 377: 486-495.
Stevens JL. (2006) Future of toxicology-mechanisms of toxicity and drug safety: where do we go from here? Chem Res Toxicol. 19: 1393-1401.
Stinstra J, et al. (2006) A Model of 3D Propagation in Discrete Cardiac Tissue. Comput Cardiol. 33: 41-44.
Stockwell BR. (2004) Exploring biology with small organic molecules. Nature. 432: 846-854.
Stoney GG. (1909) The Tension of Metallic Films Deposited by Electrolysis. Proc Roy Soc London. 82: 172-175.
Subramanian B, et al. (2010) Tissue-engineered three-dimensional in vitro models for normal and diseased kidney. Tissue Eng Part A. 16: 2821-2831.
Sun L, et al. (2007) JAK1-STAT1-STAT3, a key pathway promoting proliferation and preventing premature differentiation of myoblasts. J Cell Biol. 179: 129-138.
Sung JH and Shuler ML. (2009a) A micro cell culture analog (microCCA) with 3-D hydrogel culture of multiple cell lines to assess metabolism-dependent cytotoxicity of anti-cancer drugs. Lab Chip. 9: 1385-1394.
Sung JH and Shuler ML. (2009b) Prevention of air bubble formation in a microfluidic perfusion cell culture system using a microscale bubble trap. Biomed Microdevices. 11: 731-738.
Sung JH, et al. (2009c) Fluorescence optical detection in situ for real-time monitoring of cytochrome P450 enzymatic activity of liver cells in multiple microfluidic devices. Biotechnol Bioeng. 104: 516-525.
Sung JH, et al. (2010) A microfluidic device for a pharmacokinetic-pharmacodynamic (PK-PD) model on a chip. Lab Chip. 10: 446-455.
Sung JH, et al. (2013) Microfabricated mammalian organ systems and their integration into models of whole animals and humans. Lab Chip. 13: 1201-1212.
Suter W. (2006) Predictive value of in vitro safety studies. Curr Opin Chem Biol. 10: 362-366.
Sutton NM, et al. (2007) Clinical effects and outcome of feline permethrin spot-on poisonings reported to the Veterinary Poisons Information Service (VPIS), London. J Feline Med Surg. 9: 335-339.
Swasdison Sand Mayne R. (1992) Formation of highly organized skeletal muscle fibers in vitro. Comparison with muscle development in vivo. J Cell Sci. 102:643-652.
Swynghedauw B. (1999) Molecular mechanisms of myocardial remodeling. Physiol Rev. 79: 215-262.
Takagishi Y, et al. (2000) Species-specific difference in distribution of voltage-gated L-type Ca(2+) channels of cardiac myocytes. Am J Physiol Cell Physiol. 279: C1963-C1969.
Takahashi T. (1978) Intracellular recording from visually identified motoneurons in rat spinal cord slices. Proc R Soc Lond B Biol Sci. 202: 417-421.
Takashima Y, et al. (2007) Neuroepithelial cells supply an initial transient wave of MSC differentiation. Cell. 129: 1377-1388.

(56) References Cited

OTHER PUBLICATIONS

Tan W and Desai TA. (2003) Microfluidic patterning of cells in extracellular matrix biopolymers: effects of channel size, cell type, and matrix composition on pattern integrity. Tissue Eng. 9: 255-267.
Tanaka M, et al. (2005) An Unbiased Cell Morphology Based Screen for New, Biologically Active Small Molecules. PLoS Biol. 3: e128.
Tanaka Y, et al. (2006) An actuated pump on-chip powered by cultured cardiomyocytes. Lab Chip. 6: 362-368.
Tarasenko Yl, et al. (2007) Human fetal neural stem cells grafted into contusion-injured rat spinal cords improve behavior. JN eurosci Res. 85: 4 7-57.
Tatosian DA and Shuler ML. (2009) A novel system for evaluation of drug mixtures for potential efficacy in treating multidrug resistant cancers. Biotechnol Bioeng. 103: 187-198.
Termin A and Pette D. (1992) Changes in myosin heavy-chain isoform synthesis of chronically stimulated rat fast-twitch muscle. Eur J Biochem. 204: 569-573.
Terstappen GC, et al. (2007) Target deconvolution strategies in drug discovery. Nat. Rev Drug Discov. 6: 891-9.
Thomas CA, et al. (1972) A miniature microelectrode array to monitor the bioelectric activity of cultured cells. Exp Cell Res. 74: 61-66.
Thomas R. (1973) Boolean formalization of genetic control circuits. J Theor Biol. 1973. 42: 563-585.
Thompson PD, et al. (2006) An assessment of statin safety by muscle experts. Am J Cardiol. 97: 69C-76C.
Thompson RB, et al. (2005) Intracardiac transplantation of a mixed population of bone marrow cells improves both regional systolic contractility and diastolic relaxation. J Heart Lung Transplant. 24: 205-214.
Thorrez L, et al. (2008) Growth, differentiation, transplantation and survival of human skeletal myofibers on biodegradable scaffolds. Biomaterials. 29: 75-84.
Timmerman W and Westerink BH. (1997) Brain microdialysis of GABA and glutamate: what does it signify? Synapse. 27: 242-261.
Tobert JA. (2003) Lovastatin and beyond: the history of the HMGCoA reductase inhibitors. Nat Rev Drug Discov. 2: 517-526.
Toga T, et al. (2007) The 5-HT( 4) agonists cisapride, mosapride, and CJ-033466, a Novel potent compound, exhibit different human ether-a-go-go-related gene (hERG)-blocking activities. J Pharmacol Sci. 105: 207-210.
Tomb JF, et al. (1997) The complete genome sequence of the gastric pathogen Helicobacter pylori. Nature. 388: 539-547.
Torgan CE and Daniels MP. (2001) Regulation of myosin heavy chain expression during rat skeletal muscle development in vitro. Mol Biol Cell. 12: 1499-1508.
Torgan CE and Daniels MP. (2006) Calcineurin localization in skeletal muscle offers insights into potential new targets. J Histochem Cytochem. 54: 119-128.
Torimitsu Kand Kawana A. (1990) Selective growth of sensory nerve fibers on metal oxide pattern in culture. Brain Res Dev Brain Res. 51: 128-131.
Townsend KP and Pratico D. (2005) Novel therapeutic opportunities for Alzheimer's disease: focus on nonsteroidal anti-inflammatory drugs. FASEB J.
Tung L and Cysyk J. (2007) Imaging fibrillation/defibrillation in a dish. J Electrocardiol. 40: S62-S65.
Tung L and Zhang YB. (2006) Optical imaging of arrhythmias in tissue culture. J Electrocardiol. 39: S2-S6.
Uhm CS, et al. (2001) Synapse-forming axons and recombinant agrin induce microprocess formation on myotubes. J Neurosci. 21: 9678-9689.
Ullian EM, et al. (2004) Schwann cells and astrocytes induce synapse formation by spinal motor neurons in culture. Mol Cell Neurosci. 25: 241-251.
Umbach JA, et al. (2012) Functional neuromuscular junctions formed by embryonic stem cell-derived motor neurons. PLoS One. 7: e36049.

Urakami H and Chiu A Y. (1990) A monoclonal antibody that recognizes somatic motor neurons in the mature rat nervous system. J Neurosci. 10: 620-630.
Urazaev AK, et al. (1995) Muscle NMDA receptors regulate the resting membrane potential through No. synthase. Physiol Res. 44: 205-208.
Vakakis N, et al. (1995) In vitro myoblast to myotube transformations in the presence ofleukemia inhibitory factor. Neurochem Int. 27: 329-335.
Valentin JP, et al. (2004) Review of the predictive value of the Langendorff heart model (Screenit system) in assessing the proarrhythmic potential of drugs. J Pharmacol Toxicol Methods. 49: 171-181.
Van de Ven C, et al. (2007) The potential of umbilical cord blood multipotent stem cells for nonhematopoietic tissue and cell regeneration. Exp Hematol. 35:1753-1765.
Van der Valk J, et al. (2010) Optimization of chemically defined cell culture mediareplacing fetal bovine serum in mammalian in vitro methods. Toxicol In Vitro. 24: 1053-1063.
Van Rijen HV, et al. (2006) Connexins and cardiac arrhythmias. Adv Cardiol. 42:150-160.
Van Soest PF and Kits KS. (1998) Conopressin affects excitability, firing, and action potential shape through stimulation of transient and persistent inward currents in mulluscan neurons. J Neurophysiol. 79: 1619-1632.
Vandenburgh HH, et al. (1991) Computer aided mechanogenesis of skeletal muscle organs from single cells in vitro. FASEB J. 5: 2860-2867.
Vandenburgh HH, et al. (1996) Tissue engineered skeletal muscle organoids for reversible gene therapy. Hum Gene Ther. 7: 2195-2200.
Vandenburgh HH, et al. (2008) A drug screening platform based on the contractility of tissue engineered muscle. Muscle Nerve. 37: 438-447.
Vandenburgh HH, et al. (2009) Automated drug screening with contractile muscle tissue engineered from dystrophic myoblasts. FASEB J. 23: 3325-3334.
Vandenburgh HH. (1988) A computerized mechanical cell stimulator for tissue A888. culture: Effects on skeletal muscle organogenesis. In Vitro Cell Dev Biol. 24:609-619.
Varghese K, et al. (2009) Regeneration and characterization of adult mouse A889. hippocampal neurons in a defined in vitro system. J N eurosci Methods. 177: 51-59.
Varghese K, et al. (2010) A new target for amyloid beta toxicity validated by standard and high-throughput electrophysiologv. PLoS One. 5: e8643.
Vargo TG, et al. (1992) Monolayer Chemical Lithography and Characterization of Fluoropolymer Films. Langmuir. 8: 130-1.
Vartanian T, et al. (1988) Oligodendrocyte substratum adhesion modulates expression of adenylate cyclase-linked receptors. Proc Natl Acad Sci US A. 85:939-943.
Ventimiglia R, et a. (1987) Localization of beta-adrenergic receptors on differentiated cells of the central nervous system in culture. Proc Natl Acad Sci USA. 84: 5073-507.
Vidarsson H, et al. (2010) Differentiation of human embryonic stem cells to cardiomyocytes for in vitro and in vivo applications. Stem Cell Rev. 6: 108-120.
Viravaidya K and Shuler ML. (2004) Incorporation of 3T3-LI cells to mimic bioaccumulation in a microscale cell culture analog device for toxicity studies. Biotechnol Prog. 20: 590-597.
Vogel V and Sheetz M. (2006) Local force and geometry sensing regulate cell functions. Nat Rev Mol Cell Biol. 7: 265-275.
Vogel Zand Daniels MP. (1976) Ultrastructure of acetylcholine receptor clusters on cultured muscle fibers. J Cell Biol. 69: 501-507.
Waataja JJ, et al. (2008) Excitotoxic loss of post-synaptic sites is distinct temporally and mechanistically from neuronal death. J Neurochem. 104: 364-375.
Waggoner PS and Craighead HG. (2007) Micro- and nanomechanical sensors for environmental, chemical, and biological detection. Lab Chip. 7: 1238-1255.
Wagner I, et al. (2013) A dynamic multi-organ-chip for long-term cultivation and substance testing proven by 3D human liver and skin tissue co-culture. Lab Chip. 13: 3538-3547.

(56) References Cited

OTHER PUBLICATIONS

Wakatsuki T, et al. (2004) Phenotypic screening for pharmaceuticals using tissue constructs. Curr Pharm Biotechnol. 5: 181-189.
Walro JM and Kucera J. (1999) Why adult mammalian intrafusal and extrafusal fibers contain different myosin heavy-chain isoforms. Trends Neurosci. 22: 180-184.
Walsh DM and Selkoe DJ. (2007) A beta oligomers—a decade of discovery. J N eurochem. 101: 1172-1184.
Walsh K, et al. (2005) Human central nervous system tissue culture: a historical review and examination of recent advances. Neurobiol Dis. 18: 2-18.
Wang HW, et al. (2002) Soluble oligomers of beta amyloid (1-42) inhibit long-term potentiation but not long-term depression in rat dentate gyrus. Brain Res. 924: 133-140.
Wang P, et al. (2005) Defective neuromuscular synapses in mice lacking amyloid precursor protein (APP) and APP-Like protein 2. J Neurosci. 25: 1219-1225.
Wang X, et al. (2008) Effects of interleukin-6, leukemia inhibitory factor, and A907. ciliary neurotrophic factor on the proliferation and differentiation of adult human myoblasts. Cell Mol Neurobiol. 28: 113-124.
Ward JH, et al. (2001) Micropatteming of biomedical polymer surfaces by novel UV polymerization techniques. J Biomed Mater Res. 56: 351-360.
Warf BC, et al. (1991) Evidence for the ventral origin of oligodendrocyte precursors in the rat spinal cord. J Neurosci. 11: 2477-2488.
Wende AR, et al. (2007) A Role for the Transcriptional Coactivator PGC-1 alpha in Muscle Refueling. J Biol Chem. 282: 36642-36651.
Wesierska-Gadek J, et al. (2003) Dual action of cyclin-dependent kinase inhibitors: induction of cell cycle arrest and apoptosis. A comparison of the effects exerted by roscovitine and cisplatin. Pol J Pharmacol. 55: 895-902.
White SM and Claycomb WC. (2005) Embryonic stem cells form an organized, functional cardiac conduction system in vitro. Am J Physiol Heart Circ Physiol. 288: H670-H679.
Wilson K, et al. (2006) Reflex-arc on a chip: An in silico cell culture analogue. NSTI-Nanotech. 2: 297-300.
Wilson K, et al. (2007) Integration of Functional Myotubes with a Bio-MEMS Device for Non-Invasive Interrogation. Lab Chip. 7: 920-922.
Wilson K, et al. (2010) Measurement of contractile stress generated by cultured rat muscle on silicon cantilevers for toxin detection and muscle performance enhancement. PLoS One. 5: e11042.
Wilson K, et al. (2011) Direct patterning of coplanar polyethylene glycol alkylsilane monolayers by deep-ultraviolet photolithography as a general method for high fidelity, long-term cell patterning and culture. J Vac Sci Technol B Nanotechnol Microelectron. 29: 21020.
Windebank AJ, et al. (1985) Myelination determines the caliber of dorsal root ganglion neurons in culture. J Neurosci. 5: 1563-1569.
Wink T, et al. (1997) Self-assembled Monolayers for Biosensors. Analyst. 122:R43-R50.
Winslow RL, et al. (2005) Using models of the myocyte for functional interpretation of cardiac proteomic data. J Physiol. 563: 73-81.
Wise KD, et al. (2004) Wireless Implantable Microsystems: High-Density Electronic Interfaces to the Nervous System. Proceedings of the IEEE. 92: 76-97.
Witzemann V. (2006) Development of the neuromuscular junction. Cell Tissue Res. 326: 263-271.
Wong ROL. (1998) Calcium imaging and multielectrode recordings of global patterns of activity in the developing nervous system. Histochem J. 30: 217-229.
Wood P, et al. (1990) Studies of the initiation of myelination by Schwann cells. Ann NY Acad Sci. 605: 1-14.
Wright CD, et al. (2008) Nuclear alpha1-adrenergic receptors signal activated ERK localization to caveolae in adult cardiac myocytes. Circ Res. 103: 992-1000.
Wu H, et al. (2010) To build a synapse: signaling pathways in neuromuscular junction assembly. Development. 137: 1017-1033.
Wu P, et al. (2002) Region-specific generation of cholinergic neurons from fetal human neural stem cells grafted in adult rat. Nat Neurosci. 5: 1271-1278.
Wu ZR, et al. (2007) Layer-by-layer assembly of polyelectrolyte films improving cytocompatibility to neural cells. J Biomed Mater Res A. 81: 355-362.
Wyart C, et al. (2002) Constrained synaptic connectivity m functional mammalian neuronal networks grown on patterned surfaces. J Neurosci Methods. 117: 123-131.
Xi J, et al. (2005) Self-assembled microdevices driven by muscle. Nat Mater. 4:180-184.
Xu C, et al. (2006) Growth and differentiation of human embryonic stem cells for cardiac cell replacement therapy. Curr Stem Cell Res Ther. 1: 173-187.
Xu H, et al. (2008) Development of a stable dual cell-line GFP expression system to study estrogenic endocrine disruptors. Biotechnol Bioeng. 101: 1276-1287.
Xu L, et al. (2006) Human neural stem cell grafts ameliorate motor neuron disease in SOD-I transgenic rats. Transplantation. 82: 865-875.
Xu T, et al. (2004) Construction of high-density bacterial colony arrays and patterns by the ink-jet method. Biotechnol Bioeng. 85: 29-33.
Xu T, et al. (2005) Inkjet printing of viable mammalian cells. Biomaterials. 26:93-99.
Xu T, et al. (2006) Viability and electrophysiology of neural cell structures generated by the inkjet printing method. Biomaterials. 27: 3580-3588.
Xu T, et al. (2009) Electrophysiological characterization of embryonic hippocampal neurons cultured in a 3D collagen hydrogel. Biomaterials. 30: 4377-4383.
Yablonka-Reuveni Z. (1995) Development and postnatal regulation of adult myoblasts. Microsc Res Tech. 30: 366-380.
Yan J, et al. (2007) Extensive neuronal differentiation of human neural stem cell grafts in adult rat spinal cord. PLoS Med. 4: 318-33.
Yan Z, et al. (2002) Roscovitine: a novel regulator of P/Q-type calcium channels and transmitter release in central neurons. J Physiol. 540: 761-770.
Yang FS, et al. (2005) Curcumin inhibits formation of amyloid beta oligomers and fibrils, binds plaques, and reduces amyloid in vivo. J Biol Chem. 280: 5892-5901.
Yang J, et al. (2006) Synthesis and evaluation of poly( diol citrate) biodegradable elastomers. Biomaterials. 27: 1889-1898.
Yang L, et al. (2007) Increased asynchronous release and aberrant calcium channel activation m amyloid precursor protein deficient neuromuscular synapses. Neuroscience. 149: 768-778.
Yang LX and Nelson PG. (2004) Glia cell line-derived neurotrophic factor regulates the distribution of acetylcholine receptors in mouse primary skeletal muscle cells. Neuroscience. 128: 497-509.
Yang SY, et al. (2003) New class of ultrathin, highly cell-adhesion-resistant polyelectrolyte multilayers with micropatterning capabilities. Biomacromolecules. 4: 987-994.
Yang Y, et al. (2003) Neuronal cell death is preceded by cell cycle events at all stages of Alzheimer's disease. J Neurosci. 23: 2557-2563.
Yang Z, et al. (1999) Protein Interactions with Poly(ethylene glycol) Self-Assembled Monolayers on Glass Substrates: Diffusion and Adsorption. Langmuir. 15: 8405-8411.
Yankner BA. (1996) Mechanisms of neuronal degeneration in Alzheimer's disease. Neuron. 16: 921-932.
Yap FL and Zhang Y. (2007) Protein and cell micropatterning and its integration with micro/nanoparticles assembly. Biosens Bioelectron. 22: 775-788.
Yasuda SI, et al. (2001) A novel method to study contraction characteristics of a single cardiac myocyte using carbon fibers. Am J Physiol Heart Circ Physiol. 281: H1442-H1446.
Yeung CK, et al. (2007) Drug profiling using planar microelectrode arrays. Anal Bioanal Chem. 387: 2673-2680.
Yin SH, et al. (2005) Measuring single cardiac myocyte contractile force via moving a magnetic bead. Biophys J. 88: 1489-1495.
Zhao BL, et al. (1989) Scavenging effect of extracts of green tea and natural antioxidants on active oxygen radicals. Cell Biophys. 14: 175-185.

(56) References Cited

OTHER PUBLICATIONS

Zhou L, et al. (2005) Mechanistic model of cardiac energy metabolism predicts localization of glycolysis to cytosolic subdomain during ischemia. Am J Physiol Heart Circ Physiol. 288: H2400-H2411.
Zhou Z, et al. (1999) Block of HERG potassium channels by the antihistamine astemizole and its metabolites desmethylastemizole and norastemizole. J Cardiovasc Electrophysiol. 10: 836-843.
Zimmermann WH, et al. (2000) Three-dimensional engineered heart tissue from neonatal rat cardiac myocytes. Biotechnol Bioeng. 68: 106-114.
Zimmermann WH, et al. (2002) Tissue Engineering of a Differentiated Cardiac Muscle Construct. Circ Res. 90: 223-230.
Zorzano A, et al. (2003) Intracellular signals involved in the effects of insulin-A957. like growth factors and neuregulins on myofibre formation. Cell Signal. 15: 141-149.
Zurn AD, et al. (1996) Combined effects of GDNF, BDNF, and CNTF on motoneuron differentiation in vitro. J Neurosci Res. 44: 133-141.
Zweigerdt R, et al. (2003) Generation of confluent cardiomyocyte monolayers derived from embryonic stem cells in suspension: a cell source for new therapies and screening strategies. Cytotherapy. 5: 399-413.
Shuler ML. (Mar. 19, 2012) Functional In Vitro System for Drug Discovery. https://www.nibib.nih.gov/sites/default/files/S2_MShuler_FunctionalInvitroSystemsForDrugDiscovery.pdf.
Hierlemann et al., "CMOS-Based Bio/Chemosensor and Bioelectronic Microsystems", Procedia Chemistry, Elsevier, Amsterdam, NL, vol. 1, No. 1, Sep. 2009, pp. 5-8.
Jose Francisco Saenz Cogollo et al., "A Novel AFM-MEA Platform for Studying the Real Time Mechano-Electrical Behavior of Cardiac Myocytes", MRS Proceedings, vol. 1261, 2010, pp. 17-22.
Park et al., Neuromuscular Junction in a Micrifluidic Device, 35th Annual International Conference of the IEEE EMBS Osaka, Japan, Jul. 3-7, 2013.
Smith et al., A functional system for high-content screening of neuromuscular junctions in vitro, Technology (Singap World Sci) 2013; 1(1):37-48. doi:10.1142/S2339547813500015.
Natarajan et al., Patterned Cardiomyocytes on Microelectrode Arrays for High-Throughput Functional Side Effect Screening with Enhanced Information Content, Oct. 21-23, 2008.
Todorova et al., Transducers and Eurosensors '07, 2007 International Solid-State Sensors, Actuators and Microsystems Conference (2007).
Liu et al., Current Organic Chemistry, vol. 15, pp. 477-485 (2011).
Pramanik et al., Journal of Micromechanics and Microengineering, vol. 16, No. 10, pp. 2060-2066 (2006).
Cogollo, Jose F. Saenz, et al. "A new integrated system combining atomic force microscopy and micro-electrode array for measuring the mechanical properties of living cardiac myocytes." Biomedical microdevices 13.4 (2011): 613-621. (electronically published Apr. 1, 2011).
Office action issued for U.S. Appl. No. 14/764,683, dated Aug. 2, 2018.
Office action issued for U.S. Appl. No. 14/764,683, dated Feb. 20, 2019.
Office action issued for U.S. Appl. No. 14/764,683, dated Jun. 13, 2019.
Office action issued for U.S. Appl. No. 14/764,683, dated Jan. 7, 2020.
Advisory action issued for U.S. Appl. No. 14/764,683, dated Apr. 13, 2020.
Office action issued for U.S. Appl. No. 14/422,082, dated May 9, 2016.
Office action issued for U.S. Appl. No. 14/422,082, dated Nov. 28, 2016.
Office action issued for U.S. Appl. No. 14/422,082, dated Oct. 5, 2017.
Office action issued for U.S. Appl. No. 14/422,082, dated Jul. 27, 2018.
Advisory action issued for U.S. Appl. No. 14/422,082, dated Jan. 4, 2019.
Office action issued for U.S. Appl. No. 14/422,082, dated Feb. 6, 2020.
Advisory action issued for U.S. Appl. No. 14/422,082, dated Apr. 5, 2017.
Office action issued for U.S. Appl. No. 14/422,082, dated May 31, 2019.
Office action issued for U.S. Appl. No. 15/190,958, dated Aug. 31, 2018.
Office action issued for U.S. Appl. No. 15/190,958, dated Jun. 3, 2019.
Office action issued for U.S. Appl. No. 15/190,958, dated Mar. 16, 2020.
Advisory action issued for U.S. Appl. No. 15/190,958, dated May 18, 2020.
Office action issued for U.S. Appl. No. 14/821,675, dated Sep. 20, 2017.
Office action issued for U.S. Appl. No. 14/821,675, dated May 31, 2018.
Office action issued for U.S. Appl. No. 14/821,675, dated Mar. 14, 2019.
Advisory action issued for U.S. Appl. No. 14/821,675, dated Sep. 13, 2019.
Office action issued for U.S. Appl. No. 14/821,675, dated Apr. 4, 2020.
Notice of Allowance issued for U.S. Appl. No. 15/594,697, dated Apr. 19, 2019.
Office action issued for U.S. Appl. No. 12/661,323, dated Mar. 13, 2013.
Office action issued for U.S. Appl. No. 12/661,323, dated Nov. 5, 2013.
Office action issued for U.S. Appl. No. 12/661,323, dated Mar. 18, 2015.
Office action issued for U.S. Appl. No. 12/661,323, dated Aug. 7, 2015.
Office action issued for U.S. Appl. No. 12/661,323, dated May 5, 2016.
Office action issued for U.S. Appl. No. 12/661,323, dated Dec. 13, 2016.
Advisory action issued for U.S. Appl. No. 12/661,323, dated Nov. 4, 2015.
Office Action issued in Canadian Patent Application No. 2,899,445 dated Nov. 6, 2019, 3 pages.
Supplementary European Search Report issued in European Application No. EP 14745661, dated Aug. 10, 2016.
Extended European Search Report issued in European Application No. EP 14745661, dated Aug. 19, 2016.
Communication Pursuant to Article 94(3) issued in European Application No. EP 14745661, dated Apr. 10, 2017.
Communication Pursuant to Article 94(3) issued in European Application No. EP 14745661, dated Aug. 18, 2017.
International Search Report and Written Opinion of the International Searching Authority from Application No. PCT/US2013/055617, dated Dec. 17, 2013 (10 pages).
International Search Report and Written Opinion for International Application No. PCT/US2014/013903 dated May 15, 2014, 13 pages.

\* cited by examiner

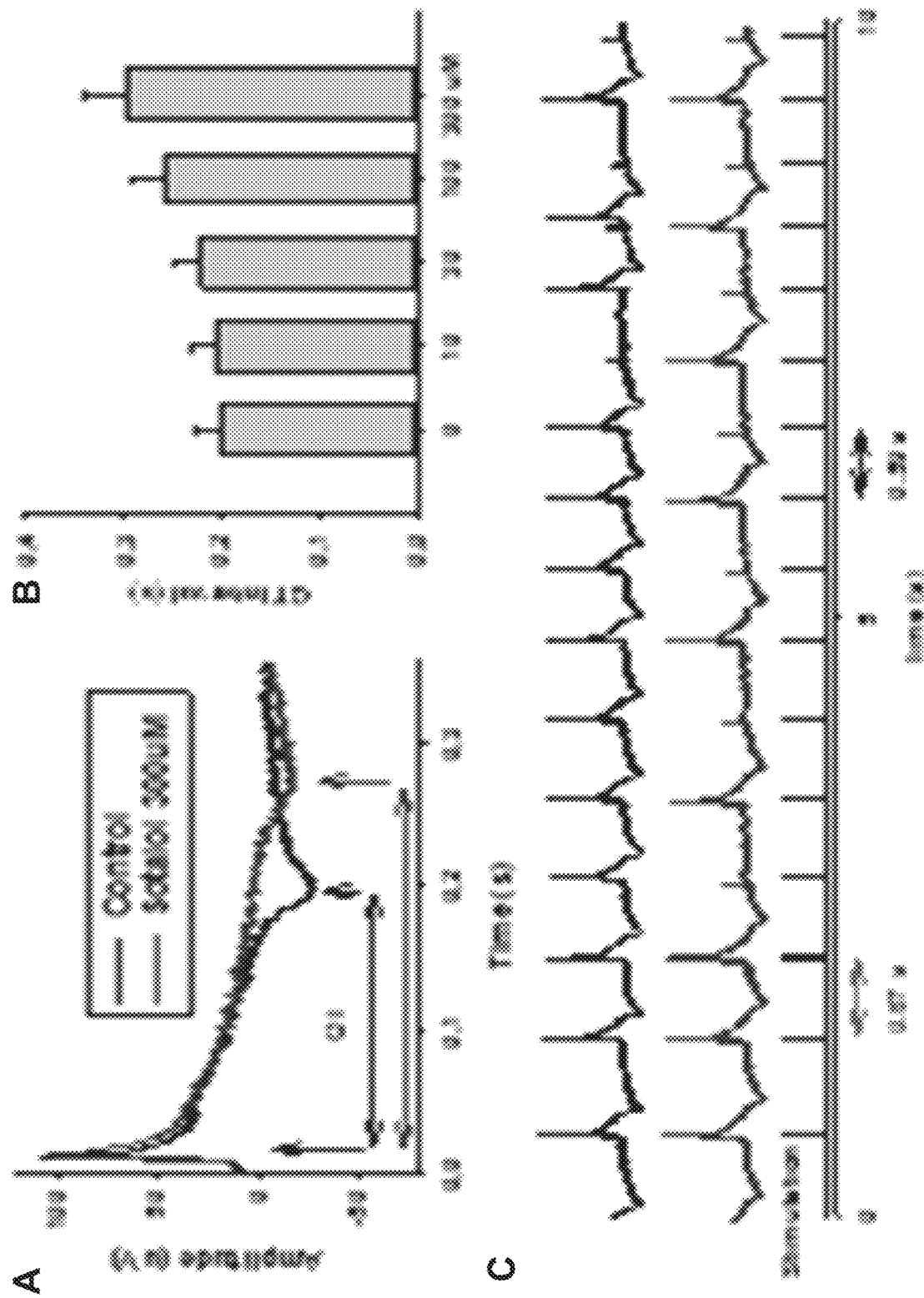
FIG. 11A, FIG. 11B, and FIG. 11C

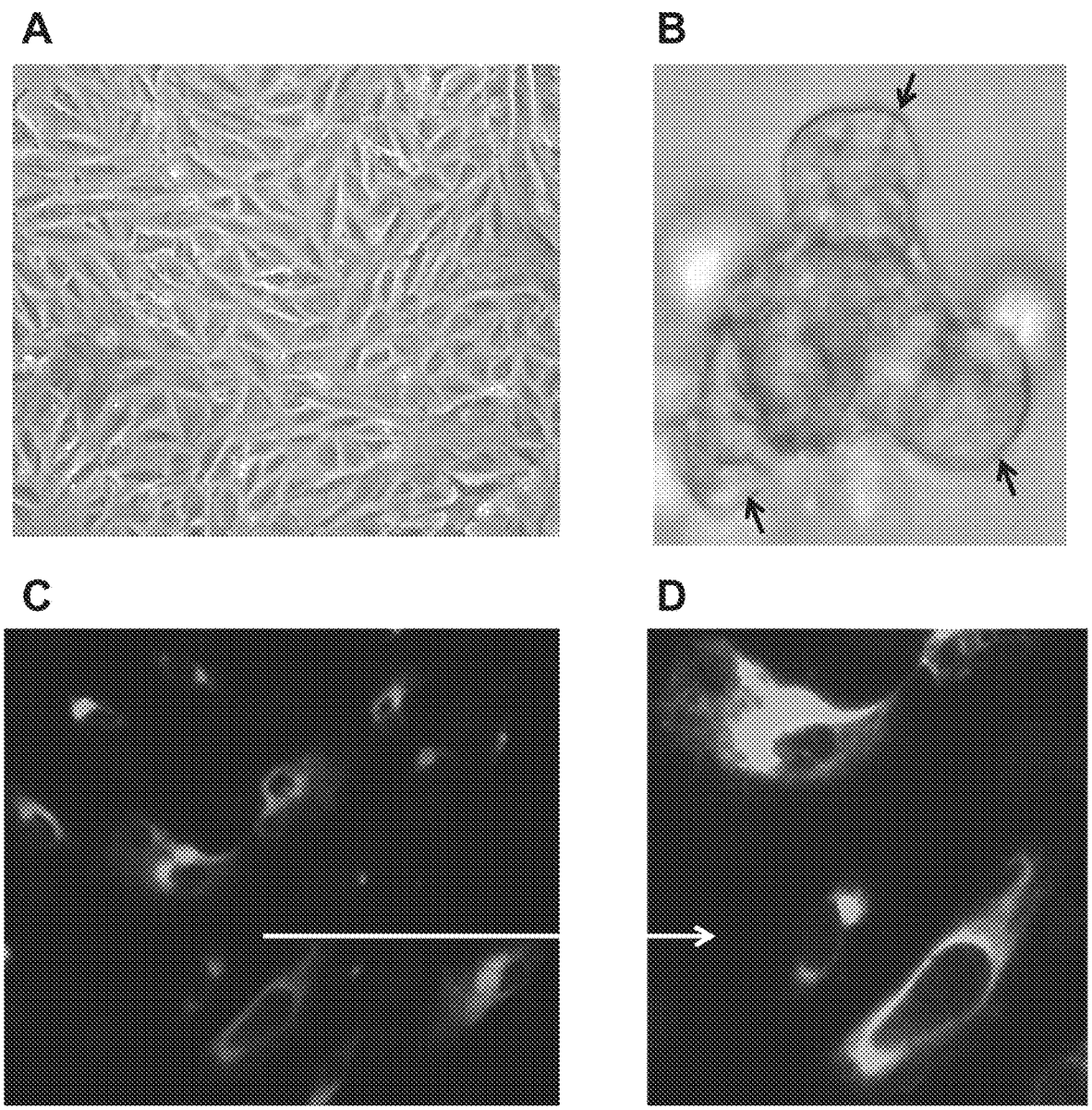
FIG. 15A, FIG. 15B, FIG. 15C, and FIG. 15D

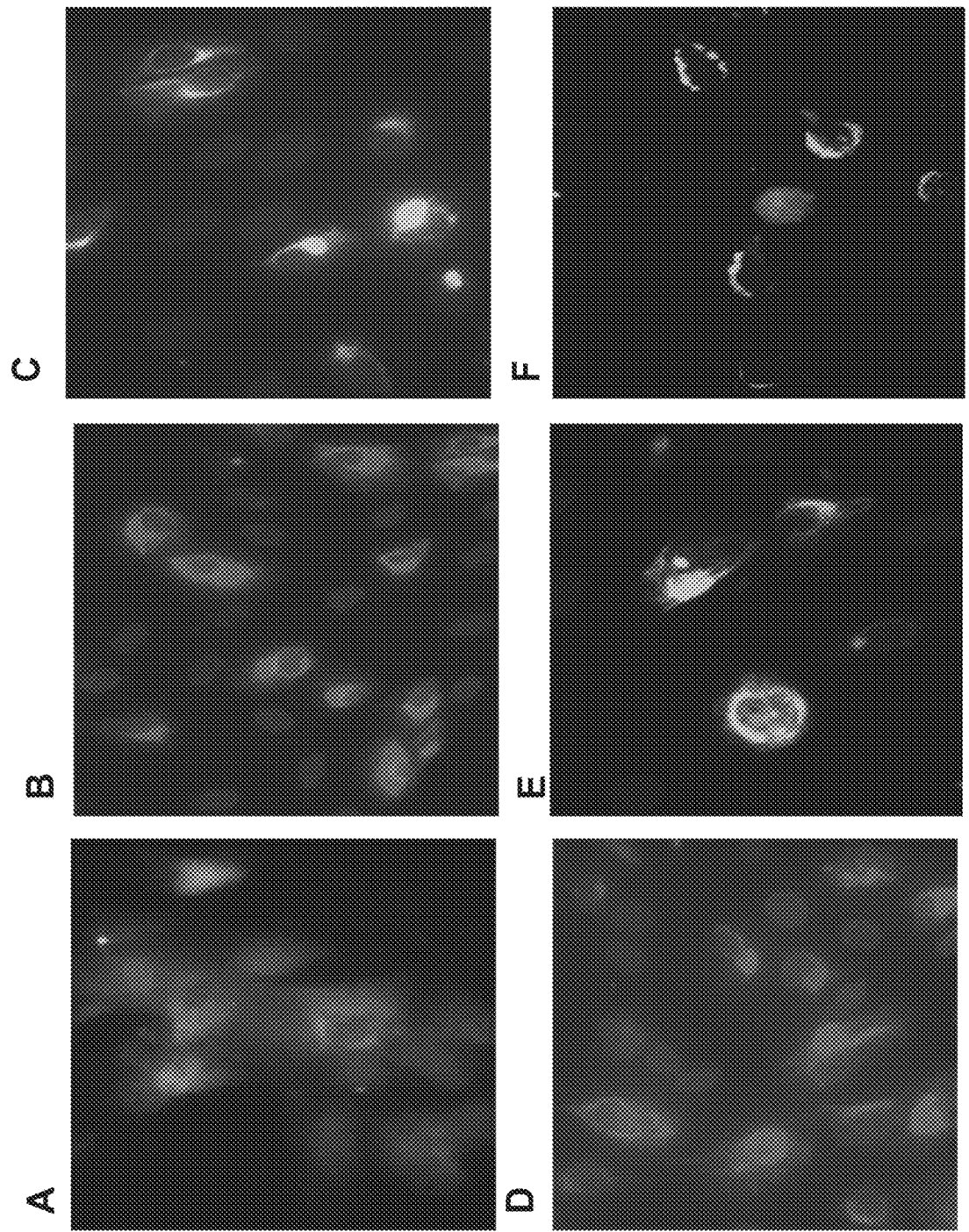
FIG. 16A, FIG. 16B, FIG. 16C, FIG. 16D, FIG. 16E, and FIG. 16F

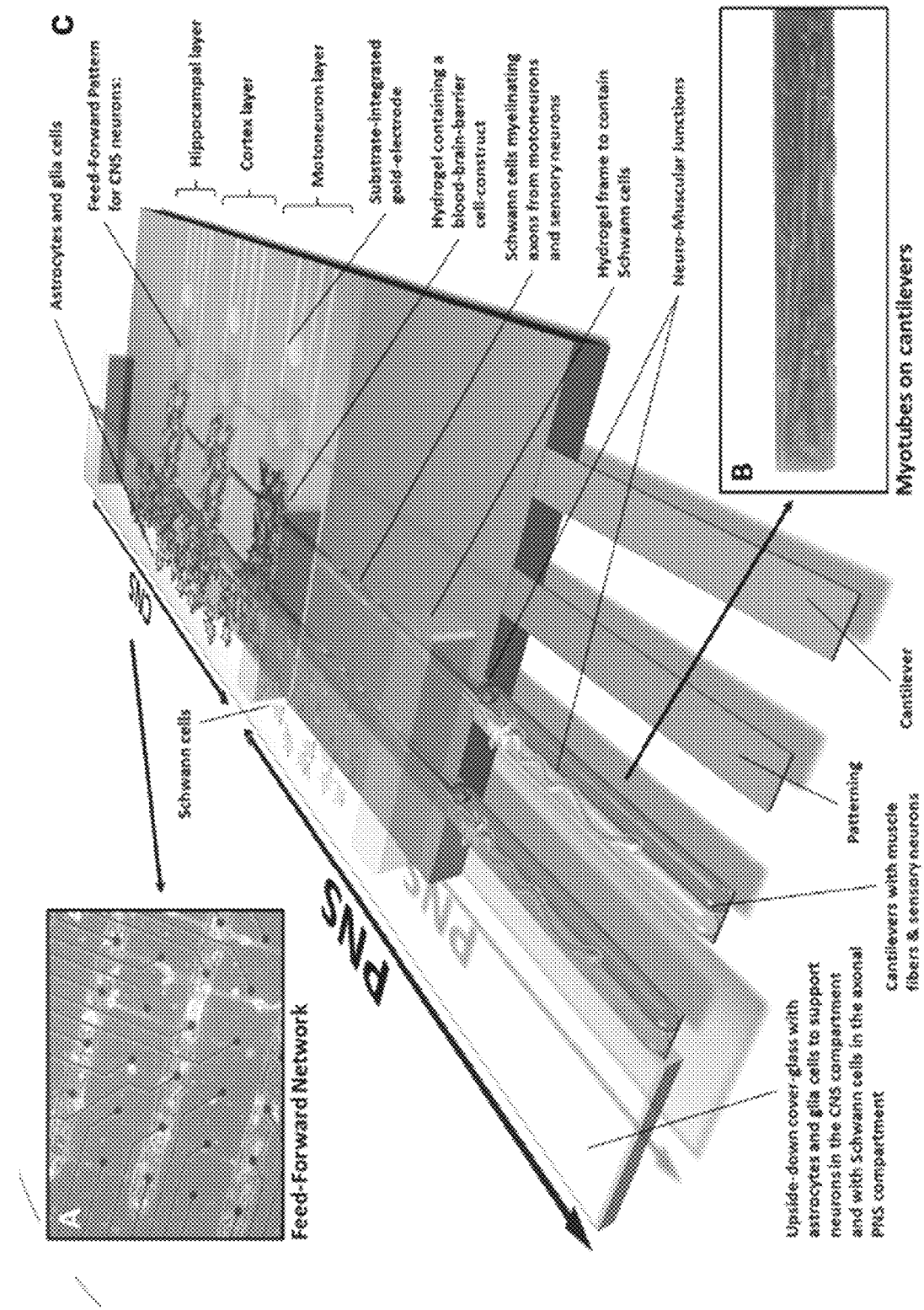
FIG. 17A, FIG. 17B, and FIG. 17C

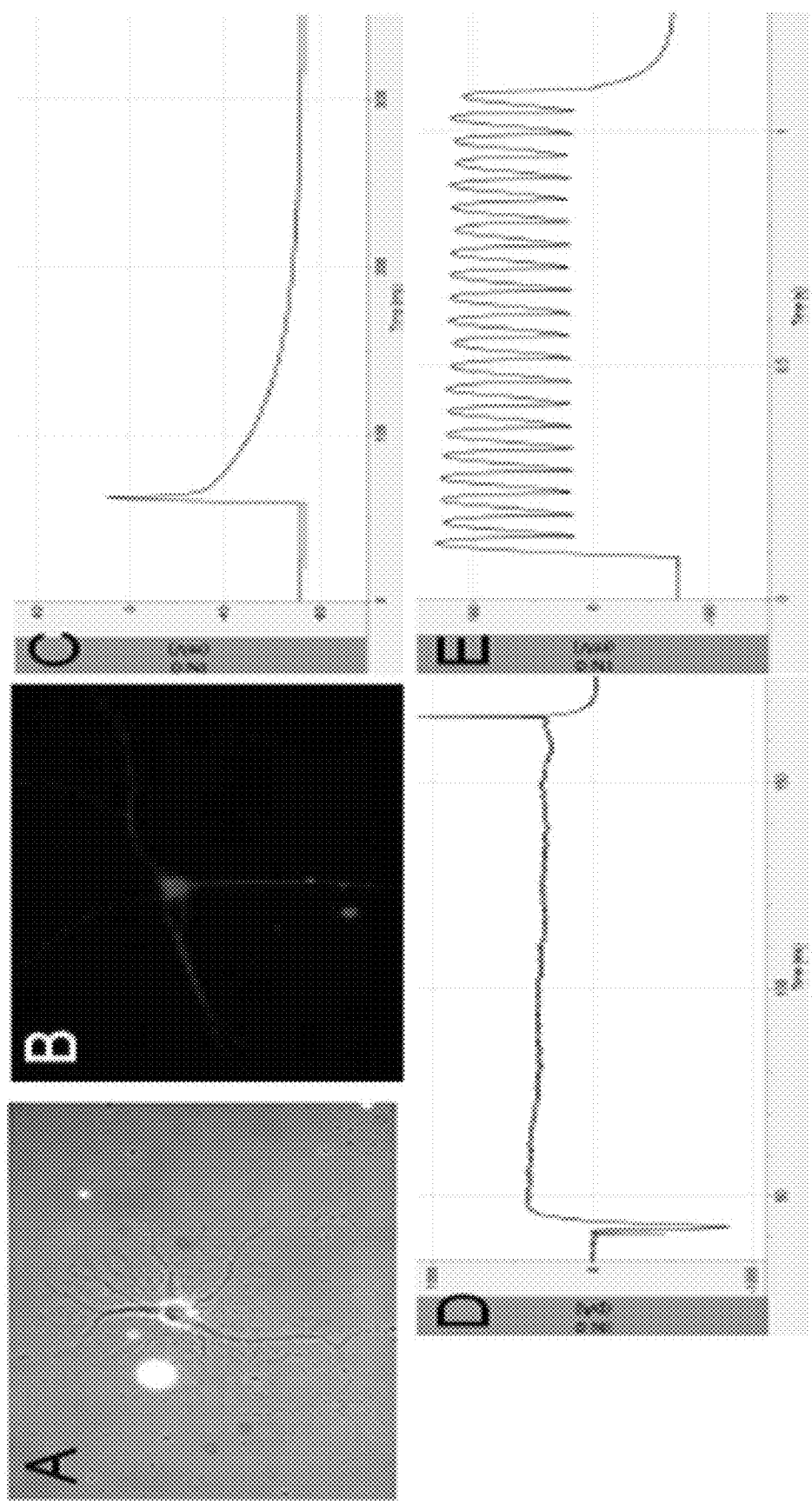
FIG. 18A, FIG. 18B, FIG. 18C, FIG. 18D, and FIG. 18E

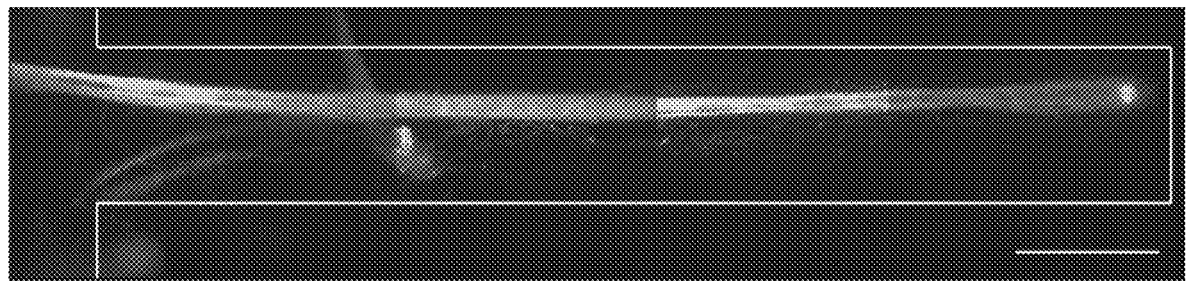
FIG. 19
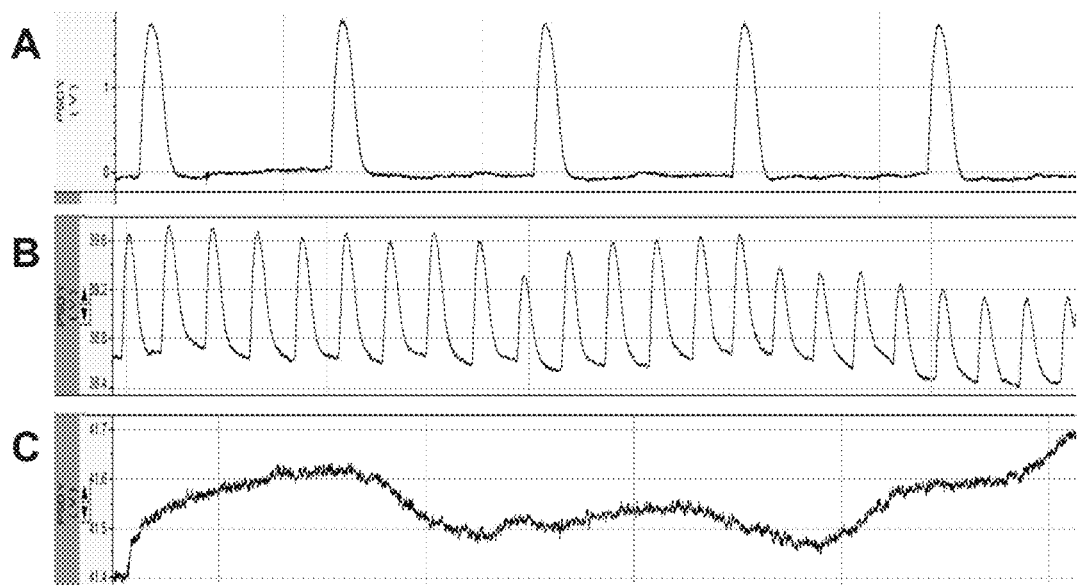
FIG. 20A, FIG. 20B, and FIG. 20C
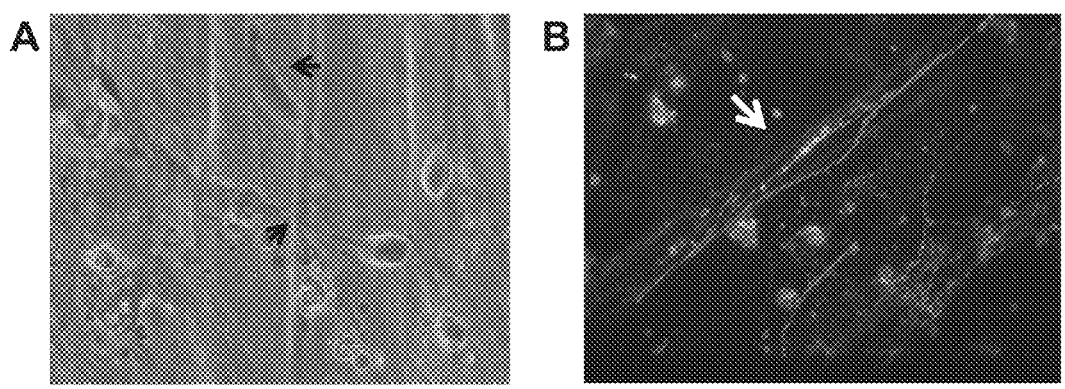
FIG. 21A and FIG. 21B

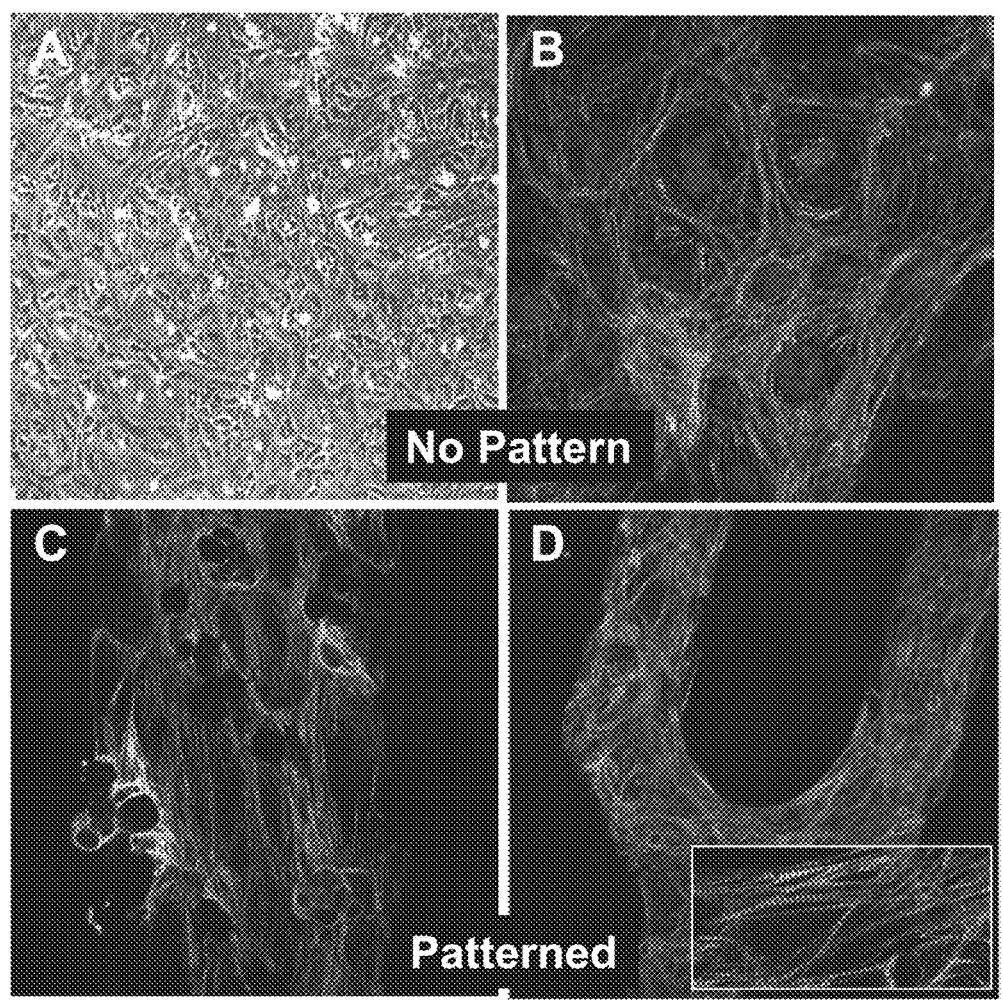
FIG. 22A, FIG. 22B, FIG. 22C, FIG. 22D, and FIG. 22E

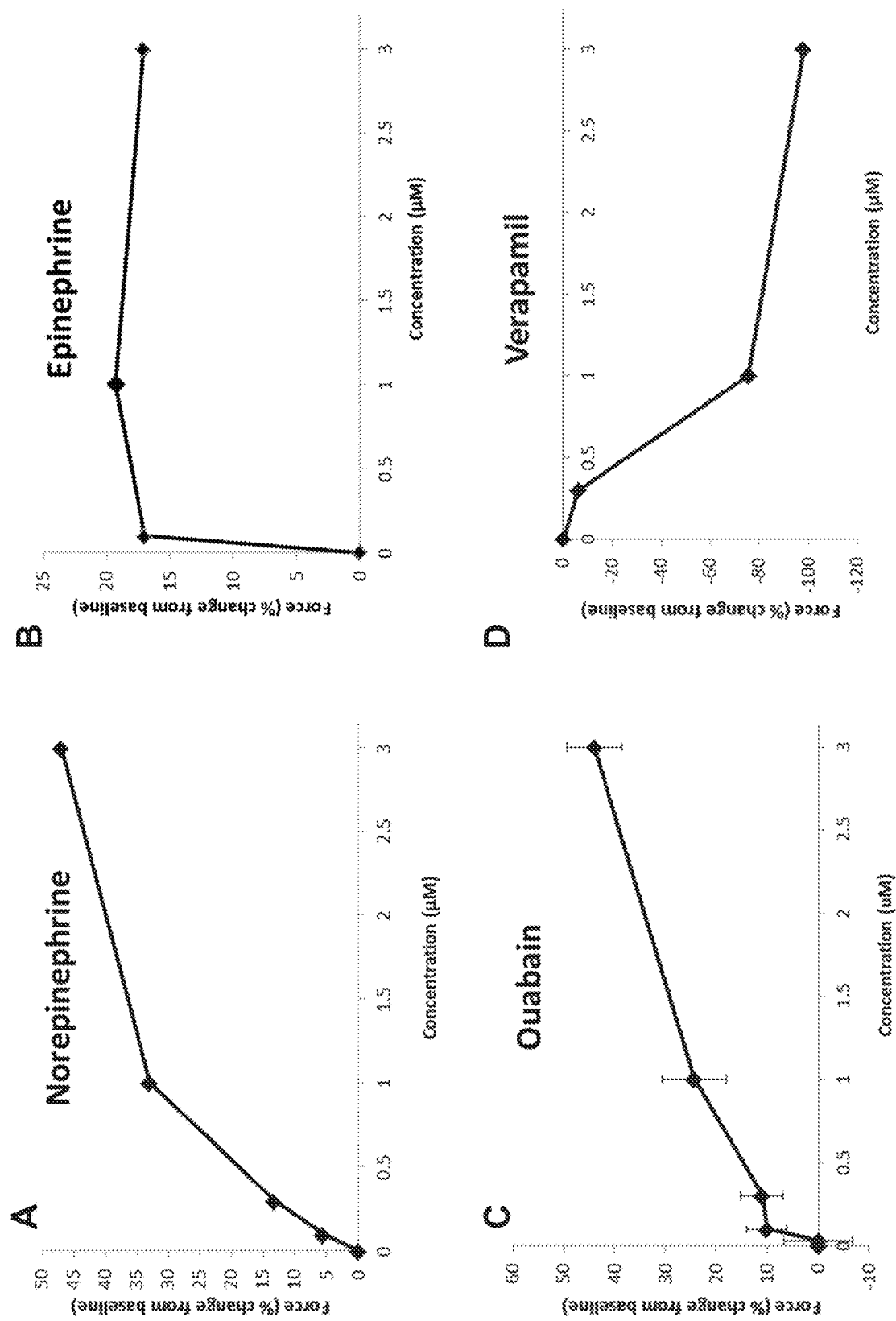
FIG. 30A, FIG. 30B, FIG. 30C, and FIG. 30D

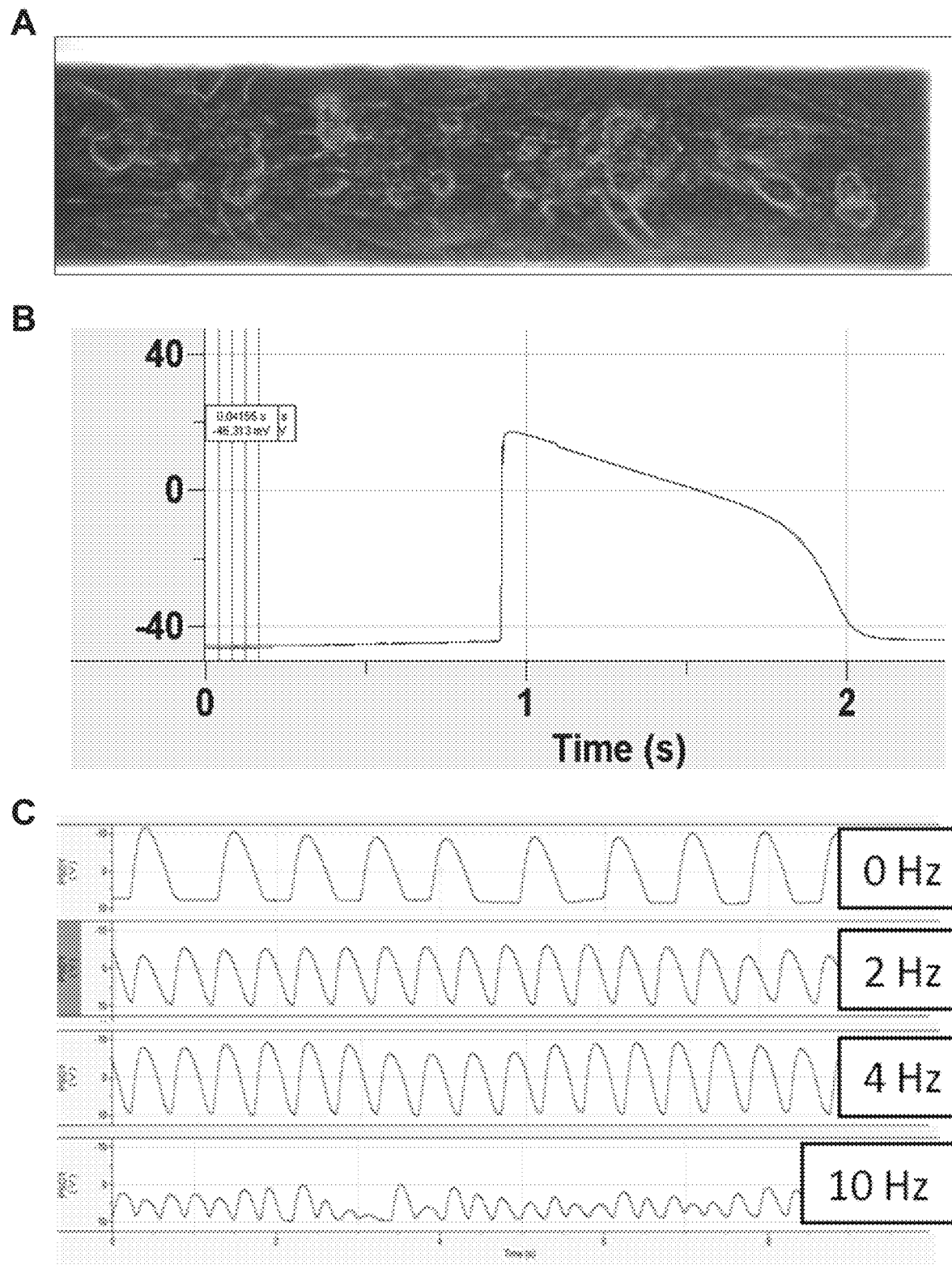
FIG. 31A, FIG. 31B, and FIG. 31C

DEVICES, SYSTEMS, AND METHODS FOR EVALUATING CARDIAC PARAMETERS

CROSS-REFERENCE TO RELATED APPLICATIONS

The present application is a continuation of U.S. patent application Ser. No. 14/764,683, filed Jul. 30, 2015, which is a 371 National Phase of International Application No. PCT/US2014/013903, filed Jan. 30, 2014, which claims the benefit of priority of U.S. Provisional Patent Application No. 61/758,628 filed Jan. 30, 2013 and of U.S. Provisional Patent Application No. 61/790,061 filed Mar. 15, 2013, each of which is incorporated herein by reference in its entirety.

STATEMENT REGARDING FEDERALLY SPONSORED RESEARCH

This invention was made with government support under UH2-TR000516, R01-NS050452, and R01-EB005459 awarded by the National Institutes of Health. The United States government has certain rights in the invention.

BACKGROUND OF THE INVENTION

The current drug development process is costly (e.g., approximately 1.2 billion dollars per drug) and time consuming (e.g., approximately 10-15 years per drug). Effective drug development to meet emergencies arising from pandemics or terrorism does not yet exist. There are several aspects of effective drug development. First, a drug screening device should identify key biomarkers and cellular responses that report physiological states. Second, to ensure accurate reporting of drug toxicology and efficacy, a device should provide physiologically relevant predictive modeling based on known clinical responses to drugs. Third, the cost should be bearable.

For example, cardiac main and side effects are major targets of pharmacological screening. The most commonly used screens with the highest predictive value are in vivo measurements on dogs, guinea pigs, or rabbits (De Clerck, 2002). However, these studies are low throughput, expensive, and suffer from interspecies differences (i.e., studies on conducted on non-humans). In most cases, animal research does not translate well to the human condition. However, the application of a high-throughput cardiac screen would save significant time and money. This would also eliminate drug failures in the clinical phase of drug development, thereby resulting in safer and cheaper drugs on the market. Therefore, a human-based in vitro system can provide the key technology necessary to speed up the drug discovery process by developing function-based human cell models that accurately capture and predict complex organ function.

These needs and other needs are satisfied by the present invention.

BRIEF SUMMARY OF THE INVENTION

Disclosed herein are in vitro physiological systems comprising a microelectrode array; one or more cantilevers; cardiac myocytes; and a medium, wherein the system measures one or more cardiac parameters.

Disclosed herein are in vitro physiological systems comprising a microelectrode array; one or more cantilevers; cardiac myocytes; and a medium, wherein the system measures one or more arrhythmogenic mechanisms.

Disclosed herein are kits comprising an in vitro physiological system and instructions for using the in vitro physiological system to measure one or more cardiac parameters.

Disclosed herein are kits comprising an in vitro physiological system and instructions for using the in vitro physiological system to measure one or more arrhythmogenic mechanisms.

Disclosed herein are processes for synthesizing one or more components of a disclosed system, wherein the one or more components comprise cantilevers.

Disclosed herein are processes for synthesizing one or more components of a disclosed system, wherein the one or more components comprise microelectrode arrays.

Disclosed herein are methods of using a disclosed system.

Disclosed herein are methods of using a disclosed system to measure one or more cardiac parameters.

Disclosed herein are methods of using a disclosed system to measure one or more arrhythmogenic mechanisms.

Disclosed herein are methods of using a disclosed system to recapitulate the electrical and contractile properties of a heart.

Disclosed herein are various uses for a disclosed in vitro physiological system.

Disclosed herein are uses of a disclosed system in one or more biomedical applications.

Disclosed herein are uses of a disclosed system in one or more toxicology studies Disclosed herein are uses of a disclosed system for drug screening.

Disclosed herein are uses of a disclosed system in lab-on-a-chip applications.

Disclosed herein are uses of a disclosed system in screening for individual medicines.

Disclosed herein are uses of a disclosed system for assessment or examination of genetic variances in the cells of a subject (e.g., induced adult cells iPSC).

BRIEF DESCRIPTION OF THE SEVERAL VIEWS OF THE DRAWINGS

The accompanying Figures, which are incorporated in and constitute a part of this specification, illustrate several aspects of the invention and together with the description serve to explain the principles of the invention.

FIG. 11A-FIG. 11C shows the effect of sotalol on various cardiac parameters such as QT interval and amplitude.

FIG. 15A shows an image of an in vitro culture of cells after immortalization by knock-in of telomerase reverse transcriptase (TERT).

FIG. 15B shows a magnified image of the image shown in FIG. 15A.

FIG. 15C shows an image of cultured cells stained for the stem cell marker Lgr5.

FIG. 15D shows a magnified image of the image shown in FIG. 15C.

FIG. 16A shows a fluorescent microscopy image of primary human colon epithelial cells stained for A33.

FIG. 16B shows a fluorescent microscopy image of primary human colon epithelial cells stained for cytokeratin 18.

FIG. 16C shows a fluorescent microscopy image of primary human colon epithelial cells stained for cytokeratin 20.

FIG. 16D shows a fluorescent microscopy image of primary human colon epithelial cells stained for villin.

FIG. 16E shows a fluorescent microscopy image of primary human colon epithelial cells stained for Muc2.

FIG. 16F shows a fluorescent microscopy image of primary human colon epithelial cells stained for chromogranin A.

FIG. 17A shows a feed-forward network as a component of a disclosed system used to examine the nervous system.

FIG. 17B shows an image of myotubes on cantilevers in a disclosed system used to examine the nervous system.

FIG. 17C shows a schematic of a disclosed system used to measure characteristics of cells in the nervous system.

FIG. 18A show an image of a neuron that displayed spine growth and extensive branching characteristic of mature neurons.

FIG. 18B shows immunocytochemical characterization of pyramidal cell using β-III tubulin.

FIG. 18C show the current flow of a cell that was cultured for 30 days in vitro.

FIG. 18D show the action potential generation of a cell that was cultured for 30 days in vitro.

FIG. 18E shows that a cell that was cultured for 30 days in vitro retained the ability to repeatedly fire.

FIG. 19 shows a composite image of a primary rat myotube co-cultured with primary rat motoneurons on a cantilever for 13 DIV and immunostained for Myosin Heavy Chain and β-III-Tubulin (cantilever edges were reinforced artificially to give an indication of their scale in relation to the cultured cells; scale bar=100 μm).

FIG. 20A shows a representative trace recording (in Volts) using laser deflection, indicating lengthwise strain on the cantilever from a myotube stimulated using broad field electrical pulses.

FIG. 20B shows the measurement of myotube contraction following neuronal stimulation via the addition of 200 μM glutamate.

FIG. 20C shows the measurement of myotube contraction following the addition of glutamate and 12.5 μM curare.

FIG. 21A shows an image of neuromuscular junction formation between human motoneurons and muscle derived from stem cells (40× magnification).

FIG. 21B shows an image of a potential synaptic site (arrow) in a day 15 co-culture demonstrated by co-localization of nerve terminals (indicated by synaptophysin) and AchR (indicated by BTX-488).

FIG. 22A shows an image of human cardiomyocytes 14 days in vitro (derived from human iPSCs, cultured in serum-free medium) obtained using light microscopy.

FIG. 22B shows an image of random (unpatterned) cardiomyocytes (derived from human iPSCs, cultured in serum-free medium) immunostained with troponin T and actin.

FIG. 22C shows an image of cardiomyocytes (derived from human iPSCs, cultured in serum-free medium) on patterned glass slides immunostained with troponin T and actin.

FIG. 22D shows an image of cardiomyocytes (derived from human iPSCs, cultured in serum-free medium) on patterned glass slides immunostained with troponin T and actin so as to demonstrate the directional alignment of muscle fibers.

FIG. 22E shows an enlarged image of the patterned cardiomyocytes on an MEA (derived from human iPSCs, cultured in serum-free medium).

FIG. 30A-FIG. 30D shows the response of cardiomyocytes cultured on silicon cantilevers comprising a DETA modification and fibronectin deposition as measured by contractile force (% change) following administration of norepinephrine (A), epinephrine (B), ouabain (C), and verapamil (D).

FIG. 31A shows a phase contrast image of human cardiomyocytes cultured in silicon cantilevers.

FIG. 31B shows a single action potential recording of cultured cardiomyocytes, which demonstrated a ventricular phenotype.

FIG. 31C shows that the beating rhythm and contractile force of cultured cardiomyocytes can be controlled with electrical stimulation (i.e., increasing stimulation frequencies from 0 Hz to 10 Hz increased beat frequency and decreased contractile forces).

Figure 1:
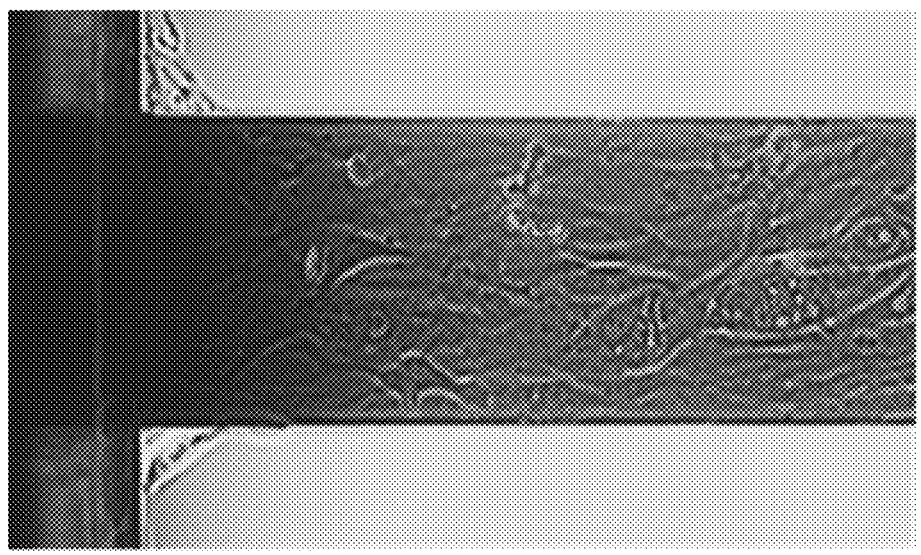
FIG. 1 shows a phase image of a monolayer of human cardiomyocytes cultured on a cantilever.
Figure 2:
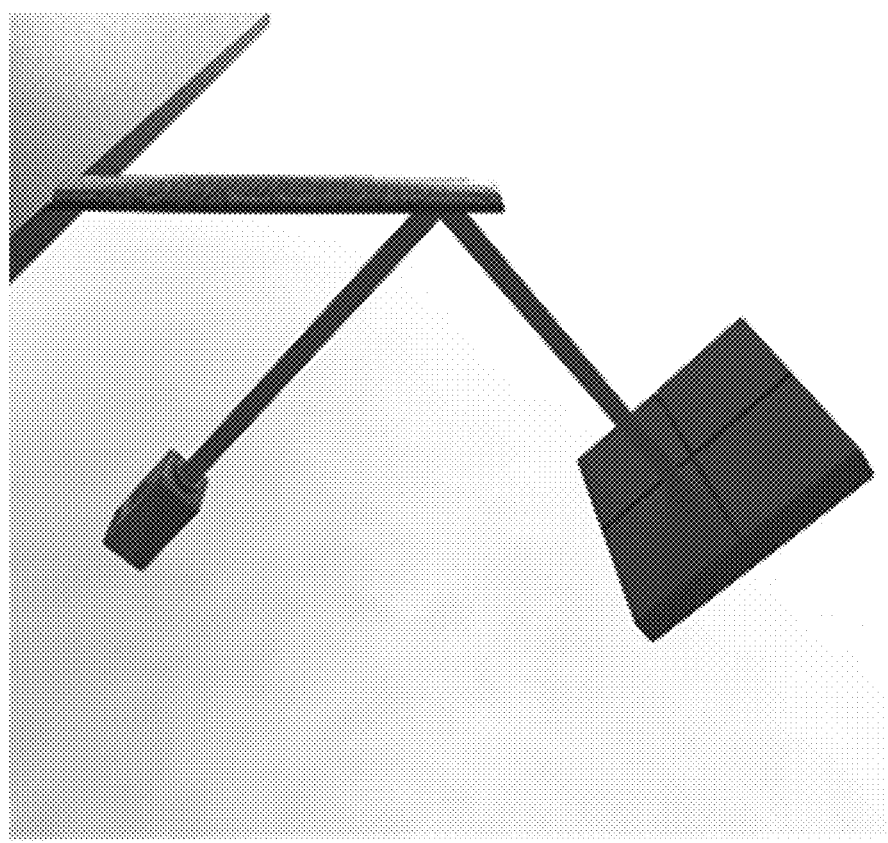
FIG. 2 shows a schematic representation of force measurement using an optical detection method.
Figure 3A:
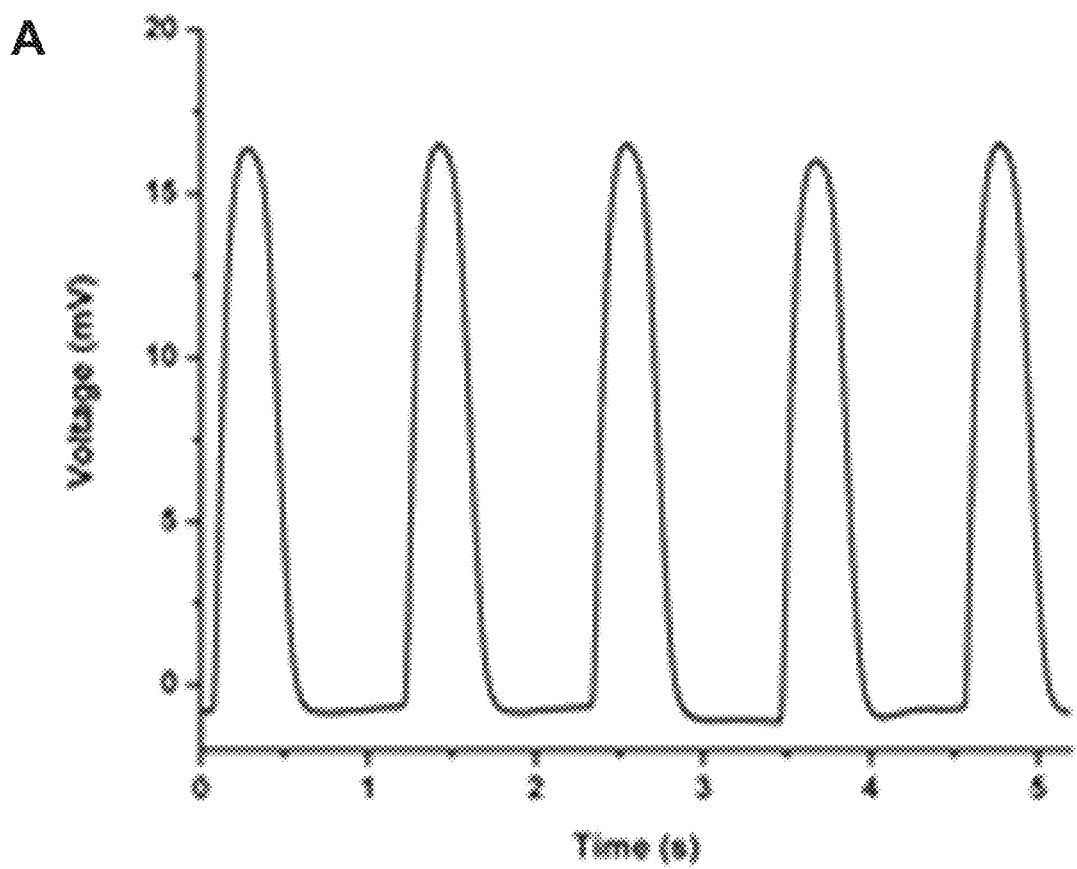
FIG. 3A shows a representative voltage recording of human cardiomyocytes seeded on cantilevers before adding 3 μM of verapamil.
Figure 3B:
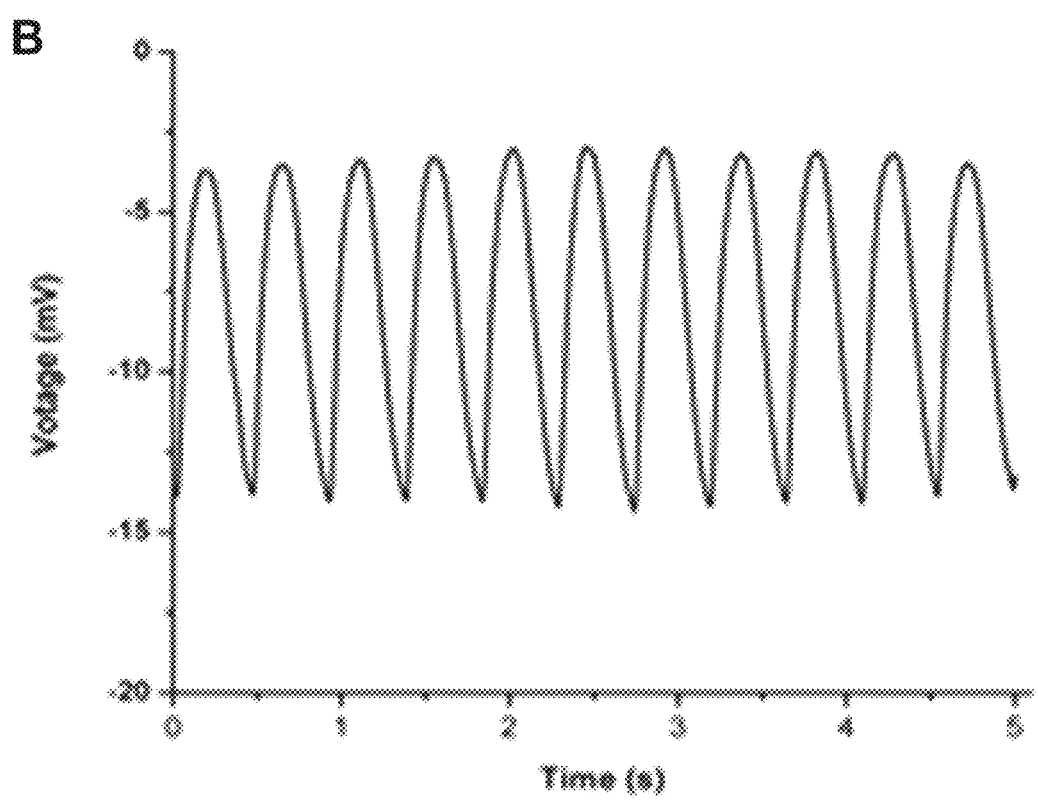
FIG. 3B shows a representative voltage recording of human cardiomyocytes seeded on cantilevers after adding 3 μM of verapamil.
Figures 4A, 4B, 4C:
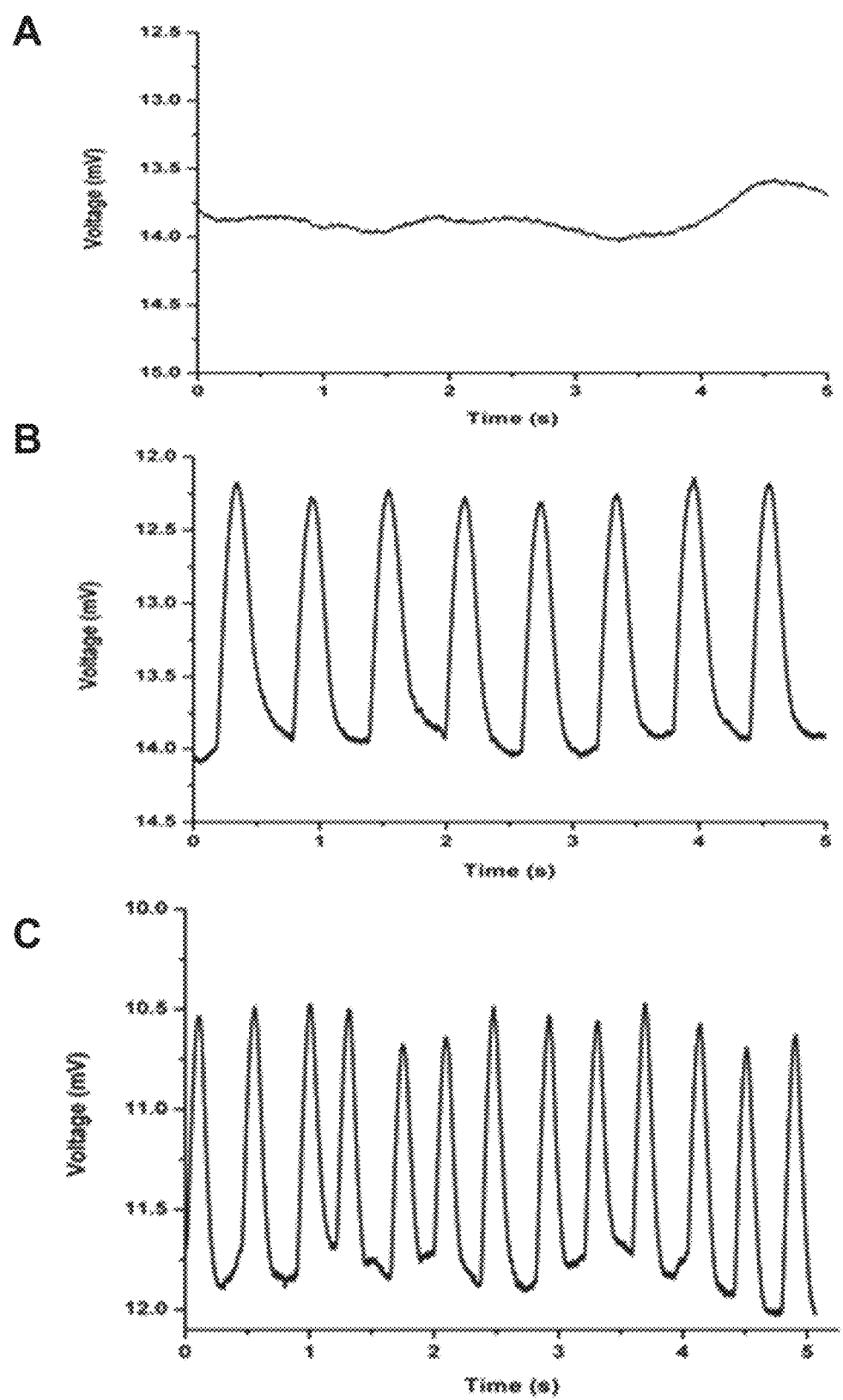
FIG. 4A shows representative voltage changes detected in human cardiomyocytes seeded on cantilevers in extracellular solution containing 0 mM $Ca^{2+}$.
FIG. 4B shows representative voltage changes detected in human cardiomyocytes seeded on cantilevers in extracellular solution containing 1 mM $Ca^{2+}$.
FIG. 4C shows representative voltage changes detected in human cardiomyocytes seeded on cantilevers in extracellular solution after adding 1 μM norepinephrine.

Additional advantages of the invention are set forth in part in the description that follows, and in part will be obvious from the description, or can be learned by practice of the invention. It is to be understood that both the foregoing general description and the following detailed description are exemplary and are not restrictive of the invention as claimed.

DETAILED DESCRIPTION OF THE INVENTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

Cardiac side effects are one of the major causes of failure for drug candidates in preclinical drug development or in clinical trials. Cardiac side effects are also responsible for the retraction of several marketed therapeutics. More than 850,000 people are hospitalized for arrhythmias each year and ventricular fibrillation (VF) is a leading cause of cardiac death (Jackson et al., 2004). Despite the intensive research in this area, the mechanism of VF is still poorly understood (Lin et al., 2008; Moe et al., 1962; Nash et al., 2006; and Pijnappels et al., 2007). Arrhythmia is a known side effect of commercial drugs. One of the mechanisms by which drugs can cause a potentially fatal form of ventricular tachy arrhythmia, called Torsades depointes (Tdp), is through the prolongation of the QT interval (in an ECG the length of the ventricular action potential). It has been reported that approximately 2-3% of all prescribed drugs can cause long QT syndrome (Recanatini et al., 2005; Sala et al., 2009). A broad range of cardiovascular drugs and antibiotics also have the potential risk of causing drug induced Tdp (Campbell et al., 2001; Hondeghem et al., 2007). At the same time, prolongation of the QT interval does not necessarily lead to Tdp; lengthening of the QT interval could even be anti-arrhythmogenic, as it is considered a mechanism of action of the class III anti-arrhythmics (Campbell et al., 2001; Hondeghem et al., 2007). Thus, a relatively high-throughput method to identify cardiac side effects and differentiate between arrhythmic and anti-arrhythmic effects at an early stage of drug development would have a significant impact on the field.

Gap junctions play an important role in the propagation of excitation in cardiac tissue. Changes in gap junction function affect major cardiac parameters, such as conduction velocity (CV). In several cardiovascular diseases, the expression of connexins (protein molecules that form gap junction channels) is decreased or their distribution is changed, leading to a malfunction in gap junction coupling. Understanding the pharmacological modulation of cardiac gap junction channels would further aid the drug development enterprise. The presently disclosed systems further aid this process.

A. DEFINITIONS

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, the terms "optional" or "optionally" can mean that the subsequently described event or circumstance can or cannot occur, and that the description includes instances where said event or circumstance occurs and instances where it does not. For example, in an aspect, in a method of using a disclosed system, the system can be optionally contacted with one or more second agents.

As used herein, the term "analog" can refer to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "subject" can refer to the target of administration, e.g., an animal. The term "subject" can include domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered.

As used herein, "cardiomyocytes" and "cardiac myocytes" can refer to the cells that constitute cardiac muscle. In an aspect, cardiomyocytes and cardiac myocytes can be used interchangeably.

As used herein, "cardiac output" can refer to the electrical rhythm generation and conduction system of the heart and/or by the force generation ability of the cardiac muscle. The skilled person in the art is familiar with "cardiac output" and the techniques available to measure cardiac output.

As used herein, the term "cardiac parameters" can refer to spontaneous beating rate, conduction velocity, field potential length (i.e., QT interval), (minimal inter-spike interval (i.e., shortest possible inter-spike interview), peak contractile force, speed of contraction, and/or time to relaxation. The skilled person in the art is familiar with "cardiac parameters" and the techniques available to measure cardiac parameters.

As used herein, "arrhythmogenic mechanisms" can refer to rhythm generation, conduction, and/or reentry. In an aspect, rhythm generation can comprise chronotropy and/or firing frequency dispersion. The skilled person in the art is familiar with "arrhythmogenic mechanisms" and the techniques available to measure arrhythmogenic mechanisms.

As used herein, "conduction" can refer to conduction velocity, conduction velocity dispersion, and/or frequency dependence of conduction velocity. The skilled person in the art is familiar with "conduction" and the techniques available to measure conduction.

As used herein, "reentry" can refer to QT interval, QT interval dispersion, reverse use dependence, absolute refractory period, and/or relative refractory period. The skilled person in the art is familiar with "reentry" and the techniques available to measure reentry.

A "patient" can refer to a subject afflicted with one or more diseases or disorders, such as, for example, a disease or disorder that affects the heart or affects cardiac muscle or affects cardiac parameters or arrhythmogenic mechanisms.

As used herein, the term "treatment" can refer to the medical management of a patient with the intent to cure, ameliorate, stabilize, and/or prevent a disease, pathological condition, or disorder (such as, for example, a disorder that affects the heart). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" can refer to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" can mean having been subjected to a physical examination by a person of skill, for example, a physician, and found to have a condition that can be diagnosed or treated by the devices, systems, and methods disclosed herein. For example, in an aspect, a subject can be diagnosed with one or more conditions that affect the heart, heart muscle, and/or heart function, and/or cause abnormalities in the subject's various cardiac parameters.

The term "contacting" as used herein can refer to bringing a disclosed composition, compound, or complex together with an intended target (such as, e.g., a cell or population of cells, a receptor, an antigen, or other biological entity) in such a manner that the disclosed composition, compound, or complex can affect the activity of the intended target (such as, e.g., a cell or population of cells, a receptor, an antigen, or other biological entity.), either directly (i.e., by interacting with the target itself), or indirectly (i.e., by interacting with another molecule, co-factor, factor, or protein on which the activity of the target is dependent). In an aspect, one or more agents can be contacted with a disclosed system or disclosed device, or cells (e.g., cardiomyocytes) contained therein.

As used herein, the term "determining" can refer to measuring or ascertaining an activity or an event or a quantity or an amount or a change in expression and/or in activity level or in prevalence and/or incidence. Determining can refer to measuring one or more cardiac parameters. Determining can refer to measuring one or more arrhythmogenic mechanisms. In an aspect, measuring one or more cardiac parameters and/or one or more arrhythmogenic mechanisms can comprise a computer or a computer system. The skilled person in the art is familiar with the use of computers and computer systems (i.e., hardware, software, other equipment, etc.) to measure one or more cardiac parameters and/or one or more arrhythmogenic mechanisms among other things.

Methods and techniques used to determining an activity or an event or a quantity or an amount or a change in expression and/or in activity level or in prevalence and/or incidence as used herein can refer to the steps that the skilled person would take to measure or ascertain some quantifiable value. The art is familiar with the ways to measure an activity or an event or a quantity or an amount or a change in expression and/or in activity level or in prevalence and/or incidence As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. For example, in an aspect, an effective amount of a disclosed composition or complex is the amount effective to alter one or more cardiac parameters and/or one or more arrhythmogenic mechanisms in a desired cell or population of cells or organ such as the heart. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a disclosed composition or complex at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. In an aspect, a preparation can be administered in a "prophylactically effective amount"; that is, an amount effective for prevention of a disease or condition.

As used herein, "growth factors" can refer to proteins that bind to receptors on the surface of one or more cells to effect cellular proliferation and/or differentiation. Growth factors are known to the art and can include, but are not limited to, the following: Epidermal Growth Factor (EGF), Platelet-Derived Growth Factor (PDGF), Fibroblast Growth Factors (FGFs), Transforming Growth Factors-β TGFs-β), Transforming Growth Factor-α (TGF-α), Erythropoietin (Epo), Insulin-Like Growth Factor-1 (IGF-1), Insulin-Like Growth Factor-2 (IGF-2), Interleukin-1 (IL-1), Interleukin-2 (IL-2), Interleukin-6 (IL-6), Interleukin-8 (IL-8), Tumor Necrosis Factor-α (TNF-α), Tumor Necrosis Factor-β (TNF-β), Interferon-γ (INF-γ), and Colony Stimulating Factors (CSFs). In an aspect, one or more growth factors can be added to the serum-free medium.

As used herein, "hormone" can refer to a chemical that interacts with a receptor in a target tissue to effect a change in the function of that tissue. Hormones are known to the art and can include, but are not limited to, the following: Adrenocorticotrophic hormone, Antidiuretic hormone, Cortisol, Dehydroepiandrostendione, Dihydrotestosterone, Estrogens (e.g., estradiol, estrone, estriol), Follicle Stimulating hormone, Growth Hormone, Inhibin, Insulin, Luteinizing Hormone, Melanocyte Stimulating Hormone, Melatonin, Progesterone, Prolactin, Proopiomelanocortin, Testosterone, Thyroid Stimulating Hormone, Thyroxine, and Triiodothyronine.

As used herein, "ouabain" refers to a cardiac glycoside that inhibits ATP-dependent sodium-potassium exchange across cell membranes. The binding of ouabain to the sodium-potassium pump (also called $Na^+/K^+$ ATPase) prevents the conformational changes necessary for proper function. The structural formula for ouabain is presented below:

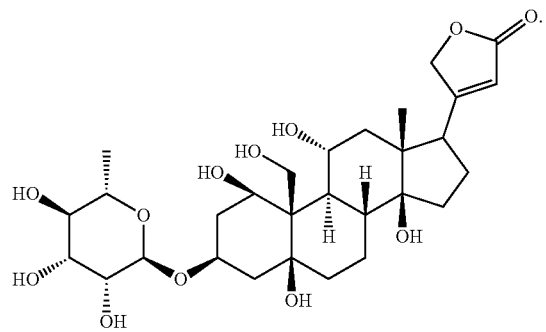

As used herein, "verapamil" or "verapamil hydrochloride" refers to a calcium ion influx inhibitor (slow-channel blocker or calcium ion antagonist) that exerts its pharmacologic effects by modulating the influx of ionic calcium across the cell membrane of the arterial smooth muscle as well as in conductile and contractile myocardial cells. The structural formula for verapamil is Presented below:

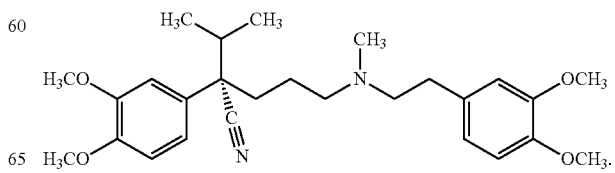

As used herein, "norepinephrine" refers to a precursor of epinephrine that is secreted by the adrenal medulla and is a widespread central and autonomic neurotransmitter. Norepinephrine is the principal transmitter of most postganglionic sympathetic fibers and of the diffuse projection system in the brain arising from the locus ceruleus. The structural formula of norepinephrine is presented below:

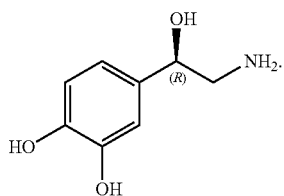

As used herein, "epinephrine" is a hormone and a neurotransmitter. Epinephrine is also referred to as adrenaline, adrenalin, or 4,5-β-trihydroxy-N-methylphenethylamine. Epinephrine is one of a group of monoamines called the catecholamines. The structural formula of epinephrine is presented below:

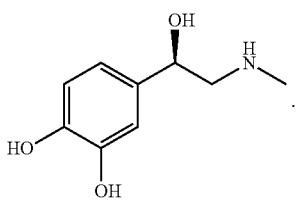

As used herein, "sotalol" or "sotalol hydrochloride" refers to an antiarrhythmic drug with Class II (beta-adrenoreceptor blocking) and Class III (cardiac action potential duration prolongation) properties. Chemically, sotalol hydrochloride is d,1-N-[4-[1-hydroxy-2-[(1-methylethyl) amino]ethyl] phenyl]methane-sulfonamide monohydrochloride. The structural formula of sotalol is presented below:

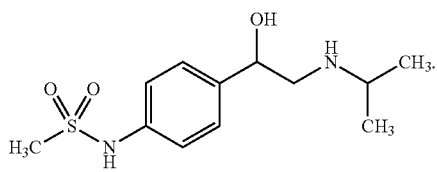 [SMILES: CC(C)NCC(O)c1ccc(NS(C)(=O)=O)cc1]

As used herein, the term "transducer" can refer to a device that converts one type of energy into another. This conversion can be to or from electrical, electromechanical, electromagnetic, photonic, photovoltaic, and other forms of energy. The skilled person in the art is familiar with transducers. For example, in an aspect, a disclosed transducer employs a piezoelectric microcantilever having a cardiac myocyte attached thereto. When the cardiac myocyte contracts, it can bend the microcantilever generating a piezoelectric signal. Conversely, if an electric signal is applied to the piezoelectric microcantilever, it can bend in response to the applied electric signal.

As used herein, the terms "cantilever" and "microcantilever" can be used interchangeably and can be used to identify the same component of a disclosed system.

As used herein, the term "piezoelectricity" can refer to the ability of certain materials (crystals and certain ceramics) to generate an electric potential in response to applied mechanical stress. The skilled person in the art is familiar with piezoelectric microcantilever fabrication and function.

B. SYSTEMS

Disclosed herein are in vitro physiological systems comprising a microelectrode array, one or more cantilevers, cardiac myocytes, and a medium, wherein the system measures one or more cardiac parameters. Disclosed herein are in vitro physiological systems comprising a microelectrode array, one or more cantilevers, cardiac myocytes, and a medium, wherein the system measures one or more arrhythmogenic mechanisms. Disclosed herein are in vitro physiological systems comprising a microelectrode array, one or more cantilevers, cardiac myocytes, and a medium, wherein the system measures one or more cardiac parameters and one or more arrhythmogenic mechanisms. In an aspect, a disclosed system can represent a two-dimensional model of a human heart. In a disclosed system, cantilevers can be generated using a photolithographic process. A disclosed cantilever can comprise silicon. A disclosed cantilever can comprise a surface modification. Surface modifications are known to the skilled person in the art. In an aspect, a surface modification can comprise a coating of (3-Trimethoxysilylpropyl)diethylenetriamine. In an aspect, a cantilever can be contacted with fibronectin (i.e., fibronectin deposition).

In a disclosed system, microelectrode arrays can comprises glass. In an aspect, a disclosed microelectrode array can comprise one or more surface modifications. Surface modifications are known to the skilled person in the art. In the art, a surface modification can be generated using traditional protein absorption or can be generated using self-assembled monolayers (SAMs). In an aspect, SAMs comprise extracellular matrix components. Extracellular matrix components are known to the skilled person in the art and can comprise fibronectin, collagen, organo silanes containing amine moieties, and polyethylene-glycol moieties. Organo silanes containing amine moieties can comprise (3-Trimethoxysilylpropyl)diethylenetriamine. Polyethylene-glycol moieties can comprise 2-[Methoxy(polyethyleneoxy)propyl]trimethoxysilane. In an aspect, a disclosed microelectrode array can comprise patterning. Methods of patterning are known to the skilled person in the art. In an aspect, patterning on the microelectrode array can be generated using a 193 nm deep-UV excimer laser through a quartz photomask. In an aspect, a disclosed microelectrode array can be contacted with fibronectin.

In a disclosed system, cardiac myocytes can be human derived cardiac myocytes. In an aspect, human derived cardiac myocytes can be derived from differentiated human embryonic stem cells. In an aspect, human derived cardiac myocytes can be derived from adult induced pluripotent stem cells. In an aspect of a disclosed system, cardiac myocytes can be cultured on a microelectrode array. In an aspect, cardiac myocytes can be commercially purchased or can be cultured from a precursor cell type.

In a disclosed system, a medium can be serum-free. Mediums, including serum-free mediums, are known to the skilled person in the art. Methods and techniques to optimize one or more mediums for a particular cell type or a particular set of culture conditions are known to the skilled person in the art. For example, a disclosed medium can be optimized via the use of additional components, such as, for example, growth factors and/or hormones and/or antibiotics.

In an aspect, a medium of a disclosed system can comprise one or more growth factors. Growth factors are known to the art and include proteins that bind to receptors on the surface of one or more cells to effect cellular proliferation and/or differentiations. Growth factors can include, but are not limited to, the following: Epidermal Growth Factor (EGF), Platelet-Derived Growth Factor (PDGF), Fibroblast Growth Factors (FGFs), Transforming Growth Factors-β TGFs-β), Transforming Growth Factor-α (TGF-α), Erythropoietin (Epo), Insulin-Like Growth Factor-1 (IGF-1), Insulin-Like Growth Factor-2 (IGF-2), Interleukin-1 (IL-1), Interleukin-2, Interleukin-6 (IL-6), Interleukin-8 (IL-8), Tumor Necrosis Factor-α (TNF-α), Tumor Necrosis Factor-β (TNF-β), Interferon-γ (NF-γ), and Colony Stimulating Factors (CSFs). In an aspect, one or more growth factors can be added to the serum-free medium. In an aspect, a medium can comprise epidermal growth factor (EGF). The skilled person is familiar with various growth factors.

In an aspect, a medium of a disclosed system can comprise one or more hormones. Hormones can include, but are not limited to, the following: Adrenocorticotrophic hormone, Antidiuretic hormone, Cortisol, Dehydroepiandrostendione, Dihydrotestosterone, Estrogens (e.g., estradiol, estrone, estriol), Follicle Stimulating Hormone, Growth Hormone, Inhibin, Insulin, Luteinizing Hormone, Melanocyte stimulating hormone, Melatonin, Progesterone, Prolactin, Proopiomelanocortin, Testosterone, Thyroid Stimulating Hormone, Thyroxine, and Triiodothyronine. In an aspect, a disclosed medium can comprise L-thyroxin. In an aspect, a disclosed medium can comprise hydrocortisone. The skilled person is familiar with various hormones.

In an aspect, a disclosed system can measure contractile force of the cardiac myocytes. In an aspect, a disclosed system can measure electrical properties of the cardiac myocytes. In an aspect, a disclosed system can measure both contractile force and electrical properties of the cardiac myocytes.

One or more agents can be introduced into a disclosed system. Agents are known to the skilled person in the art. For example, agents include, but are not limited to, the following: metabolic inhibitors, nutritional supplements, therapeutic compounds, compositions, and drugs, investigational compounds, compositions, and drugs, biosimilars, agonists, antagonists, hormones, growth factors, small molecules, monoclonal antibodies, and combinations thereof.

In an aspect, one or more agents can be introduced to a disclosed system. In an aspect, following the introduction of one or more agents, a disclosed system can measure contractile force of the cardiac myocytes. In an aspect, following the introduction of one or more agents, a disclosed system can measure electrical properties of the cardiac myocytes. In an aspect, following the introduction of one or more agents, a disclosed system can measure both contractile force and electrical properties of the cardiac myocytes.

In an aspect, a disclosed system can evaluate arrhythmogenic mechanisms. In an aspect, following the introduction of one or more agents, a disclosed system can evaluate arrhythmogenic mechanisms. Arrhythmogenic mechanisms are known to the art and can comprise rhythm generation, conduction, and reentry. In an aspect, rhythm generation can comprise chronotropy and firing frequency dispersion. In an aspect, conduction can comprise conduction velocity, conduction velocity dispersion, and frequency dependence of conduction velocity. In an aspect, reentry can comprise QT interval, QT interval dispersion, reverse use dependence, absolute refractory period, and relative refractory period.

In an aspect, a disclosed system can evaluate parameters of cardiac function. In an aspect, following the introduction of one or more agents, a disclosed system can evaluate parameters of cardiac function. Parameters of cardiac function are known to the skilled person in the art. Parameters of cardiac function can comprise spontaneous beating rate, conduction velocity, QT interval, minimal inter-spike interval (upon high frequency stimulation), peak contractile force, speed of contraction, and time to relaxation. Thus, in an aspect, a disclosed system can evaluate one or more parameters of cardiac functions, wherein the one or more parameters comprise spontaneous beating rate, conduction velocity, QT interval, minimal inter-spike interval (upon high frequency stimulation), peak contractile force, speed of contraction, and time to relaxation.

In an aspect, a disclosed system can be used in conjunction with SCREENIT.

C. KITS

Disclosed herein are kits comprising an in vitro physiological system and instructions for using the in vitro physiological system to measure one or more cardiac parameters. Disclosed herein are kits comprising an in vitro physiological system and instructions for using the in vitro physiological system to measure one or more arrhythmogenic mechanisms. In a disclosed kit, an in vitro physiological system can comprise a microelectrode array, one or more cantilevers, cardiac myocytes, and a medium.

Cantilevers of a disclosed kit can be generated using a photolithographic process. A disclosed cantilever can comprise silicon. A disclosed cantilever can comprise a surface modification. Surface modifications are known to the skilled person in the art. In an aspect, a surface modification can comprise a coating of (3-Trimethoxysilylpropyl)diethylenetriamine. In an aspect, a cantilever can be contacted with fibronectin.

A microelectrode array of a disclosed kit can comprise glass. In an aspect, a disclosed microelectrode array can comprise one or more surface modifications. Surface modifications are known to the skilled person in the art. In the art, a surface modification can be generated using traditional protein absorption or can be generated using self-assembled monolayers (SAMs). In an aspect, SAMs comprise extracellular matrix components. Extracellular matrix components are known to the skilled person in the art and can comprise fibronectin, collagen, organo silanes containing amine moieties, and polyethylene-glycol moieties. Organo silanes containing amine moieties can comprise (3-Trimethoxysilylpropyl)diethylenetriamine.

Polyethylene-glycol moieties can comprise 2-[Methoxy (polyethyleneoxy)propyl]trimethoxysilane. In an aspect, a microelectrode array of a disclosed kit can comprise patterning. Methods of patterning are known to the skilled person in the art. In an aspect, patterning on the microelectrode array can be generated using a 193 nm deep-UV excimer laser through a quartz photomask. In an aspect, a disclosed microelectrode array can be contacted with fibronectin.

Cardiac myocytes of a disclosed kit can be human derived cardiac myocytes. In an aspect, human derived cardiac myocytes can be derived from differentiated human embryonic stem cells. In an aspect, human derived cardiac myocytes can be derived from adult induced pluripotent stem cells. In an aspect of a disclosed system, cardiac myocytes can be cultured on a microelectrode array. In an aspect, cardiac myocytes can be commercially purchased or can be cultured from a precursor cell type.

The medium of a disclosed kit can be serum-free. Mediums, including serum-free mediums, are known to the skilled person in the art. Methods and techniques to optimize one or more mediums for a particular cell type or a particular set of culture conditions are known to the skilled person in the art. For example, a medium of a disclosed kit can be optimized via the use of additional components, such as, for example, growth factors and/or hormones and/or antibiotics.

For example, in an aspect, a medium of a disclosed kit can comprise one or more growth factors. Growth factors are known to the art and include proteins that bind to receptors on the surface of one or more cells to effect cellular proliferation and/or differentiations. Growth factors can include, but are not limited to, the following: Epidermal Growth Factor (EGF), Platelet-Derived Growth Factor (PDGF), Fibroblast Growth Factors (FGFs), Transforming Growth Factors-β TGFs-β), Transforming Growth Factor-α (TGF-α), Erythropoietin (Epo), Insulin-Like Growth Factor-1 (IGF-1), Insulin-Like Growth Factor-2 (IGF-2), Interleukin-1 (IL-1), Interleukin-2 (IL-2), Interleukin-6 (IL-6), Interleukin-8 (IL-8), Tumor Necrosis Factor-α (TNF-α), Tumor Necrosis Factor-β (TNF-β), Interferon-γ (INF-γ), and Colony Stimulating Factors (CSFs). In an aspect, one or more growth factors can be added to the serum-free medium. In an aspect, a medium can comprise epidermal growth factor (EGF).

For example, in an aspect, a medium of a disclosed kit can comprise one or more hormones. Hormones can include, but are not limited to, the following: Adrenocorticotrophic hormone, Antidiuretic Hormone, Cortisol, Dehydroepiandrostendione, Dihydrotestosterone, Estrogens (e.g., estradiol, estrone, estriol), Follicle Stimulating Hormone, Growth Hormone, Inhibin, Insulin, Luteinizing Hormone, Melanocyte Stimulating Hormone, Melatonin, Progesterone, Prolactin, Proopiomelanocortin, Testosterone, Thyroid Stimulating Hormone, Thyroxine, and Triiodothyronine. In an aspect, a medium of a disclosed kit can comprise L-thyroxin. In an aspect, a medium of a disclosed kit can comprise hydrocortisone.

In an aspect, components of a disclosed kit can be used measure contractile force of the cardiac myocytes. In an aspect, components of a disclosed kit can be used can measure electrical properties of the cardiac myocytes. In an aspect, components of a disclosed kit can be used to measure both contractile force and electrical properties of the cardiac myocytes.

One or more agents can be introduced into the in vitro physiological system of a disclosed kit Agents are known to the skilled person in the art. For example, agents include, but are not limited to, the following: metabolic inhibitors, nutritional supplements, therapeutic compounds, compositions, and drugs, investigational compounds, compositions, and drugs, biosimilars, agonists, antagonists, hormones, growth factors, small molecules, monoclonal antibodies, and combinations thereof.

In an aspect, one or more agents can be introduced to the in vitro physiological system of a disclosed kit. In an aspect, following the introduction of one or more agents, components of a disclosed kit can be used measure contractile force of the cardiac myocytes. In an aspect, following the introduction of one or more agents, components of a disclosed system can be used to measure electrical properties of the cardiac myocytes. In an aspect, following the introduction of one or more agents, components of a disclosed system can be used to measure both contractile force and electrical properties of the cardiac myocytes.

In an aspect, components of a disclosed kit can be used to evaluate arrhythmogenic mechanisms. In an aspect, following the introduction of one or more agents, components of a disclosed kit can be used to evaluate arrhythmogenic mechanisms. Arrhythmogenic mechanisms are known to the art and can comprise rhythm generation, conduction, and reentry. In an aspect, rhythm generation can comprise chronotropy and firing frequency dispersion. In an aspect, conduction can comprise conduction velocity, conduction velocity dispersion, and frequency dependence of conduction velocity. In an aspect, reentry can comprise QT interval, QT interval dispersion, reverse use dependence, absolute refractory period, and relative refractory period.

In an aspect, components of a disclosed kit can be used to evaluate parameters of cardiac function. In an aspect, following the introduction of one or more agents, components of a disclosed kit can be used to evaluate parameters of cardiac function. Parameters of cardiac function are known to the skilled person in the art. Parameters of cardiac function can comprise spontaneous beating rate, conduction velocity, QT interval, minimal inter-spike interval (upon high frequency stimulation), peak contractile force, speed of contraction, and time to relaxation. Thus, in an aspect, a disclosed kit can be used to evaluate one or more parameters of cardiac functions, wherein the one or more parameters comprise spontaneous beating rate, conduction velocity, QT interval, minimal inter-spike interval (upon high frequency stimulation), peak contractile force, speed of contraction, and time to relaxation.

In an aspect, a disclosed kit can be used in conjunction with SCREENIT.

D. METHODS USING THE DISCLOSED SYSTEMS

Disclosed herein are methods of using a disclosed system. In an aspect, disclosed herein is a method of using a disclosed system to measure one or more cardiac parameters. In an aspect, disclosed herein is a method of using a disclosed system measure one or more arrhythmogenic mechanisms. Disclosed herein is a method of using a disclosed system to measure one or more cardiac parameters and to measure one or more arrhythmogenic mechanisms. In an aspect, disclosed herein is a method of using a disclosed system to recapitulate the electrical and contractile properties of a human heart.

E. USES OF THE DISCLOSED SYSTEMS

Disclosed herein are various uses for the disclosed in vitro physiological systems.

Disclosed herein are uses of a disclosed system in one or more biomedical applications. For example, disclosed herein is a use of a disclosed system in drug discovery. In an aspect, drug discovery can refer to discovery of drugs or agents or compounds that target cardiac output. In an aspect, cardiac output can be enhanced. In an aspect, cardiac output can be determined by the electrical rhythm generation and conduction system of the heart and by the force generation ability of the cardiac muscle. The general concept of drug discovery is known to the art.

Disclosed herein are uses of a disclosed system in one or more toxicology studies. In an aspect, toxicology studies can refer to the examination or assessment of drugs or agents or compounds that target cardiac output. In an aspect, cardiac output can be determined by the electrical rhythm generation and conduction system of the heart and by the force generation ability of the cardiac muscle. The general concept of toxicology studies is known to the art.

Disclosed herein are uses of a disclosed system for drug screening. The general concept of drug screening is known to the art. In an aspect, drug screening can refer to the screening of one or more drugs or agents or compounds for an ability to elicit cardiac effects and/or cardiac side effects.

Disclosed herein are uses of a disclosed system in lab-on-a-chip applications. Disclosed herein are uses of a disclosed system in screening for individual medicines. Disclosed herein are uses of a disclosed system for assessment or examination of genetic variances in the cells of a subject (e.g., induced pluripotent stem cells or iPSCs).

F. SYNTHESIS

Disclosed herein are processes for synthesizing one or more components of a disclosed system. For example, processes for synthesizing a patterned microelectrode array are described in Natarajan et al., 2011, which is incorporated herein by reference in its entirety for its teachings regarding the synthesis of a patterned microelectrode array. For example, processes for synthesizing a silicon cantilever are described in Wilson et al., 2010, which is incorporated herein by reference in its entirety for its teachings regarding the synthesis of a silicon cantilever.

It is contemplated that each disclosed method can further comprise additional steps, manipulations, and/or components. It is also contemplated that any one or more step, manipulation, and/or component can be optionally omitted. It is understood that a disclosed methods can be used to provide the disclosed compounds. It is also understood that the products of the disclosed methods can be employed in the disclosed methods of using.

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention. Efforts have been made to ensure accuracy with respect to numbers (e.g., amounts, temperature, etc.), but some errors and deviations should be accounted for.

The disclosed systems are based on human cardiac myocytes, though the invention contemplates cardiac myocytes from subjects not limited to humans, for example, subjects listed herein, including but not limited to animals. As described herein, the incorporation of a functional cardiac system based on patterned cardiac cells integrated with microelectrode assays enabled the measurement of several cardiac parameters including conduction velocity, peak amplitude and spontaneous frequency, QT interval, and relative refractory period (which is related to triangulation). In doing so, the disclosed systems demonstrated high predictive value for cardiac side effects, electrical conduction, and cardiac muscle force generation.

i) Materials and Devices
a. Preparation of Cell Culture Medium

In the disclosed system, the human-derived cardiac myocytes were cultured in a serum-free medium. The medium was optimized to enhance human cardiac myocyte growth and differentiation. Specifically, the medium was supplemented with specific growth factor such as epidermal growth factor (EGF) or hormones such as hydrocortizone and L-thyroxin. In an aspect, the serum-free medium can comprise 100 mL Ultraculture medium (Bio Whittaker Cambrex) supplemented with 10 mL B27, 1 mL L-glutamine (Gibco/Invitrogen), 1 mL Penicillin Streptomycin, 0.375 g dextrose (Fisher Scientific) in 800 µL water, 1 mL non-essential amino acids and 1 mL of Hepes buffer (Gibco/Invitrogen) (Sathaye et al., 2006). Additional growth factors can also added to improve cell survival in the serum-free conditions including 0.1 µg/mL of L-thyroxine, 10 ng/mL of epidermal growth factor (Sigma-Aldrich), and 0.5 µg/mL of hydrocortisone (BD biosciences).

b. Fabrication of Cantilever

The layout for the cantilevers was generated using AutoCAD 2004. The patterns were written to chrome coated 5-inch sodalime glass masks for front and backside photolithography. Cantilevers were fabricated from 6-inch double-sided polished silicon-on-insulator (SOI) wafers with a 5 µm crystalline silicon layer (front side) and a 500 µm silicon dioxide layer (back side). The front side was primed with a 10 nm layer of hexamethyldisilazane (HMDS) to promote resist adhesion. A 5 µm layer of the photoresist AZ 5214 E (Clariant, Muttenz, Switzerland) was spun onto the device layer followed by softbake, alignment, exposure, and development. The device layer was etched using the deep reactive ion etch (DRIE) process at a rate of 2 µm/min. Resist was stripped and a 0.5 µm thick layer of silicon dioxide was deposited via Plasma Enhanced Chemical Vapor Deposition (PECVD) to protect the device layer during subsequent processing. The wafer was then flipped over and was primed with a 10 nm layer of HMDS and spun with 4.15 µm layer of AZ 9245 photoresist (Clariant, Muttenz, Switzerland). Coating was followed by softbake, front-back alignment, development, and DRIE etch at 4 µm/min until the bulk of the back side had been etched through leaving only the buried native oxide layer. The devices were then subjected to a buffered HF dip to remove the buried native oxide layer as well as the silicon dioxide that had been deposited onto the device layer. Individual devices were separated by breaking connecting tabs that were incorporated into the device design. Cantilever dimensions were measured using a JEOL 6400 scanning electron microscope (SEM) at a take-off angle of 50° off normal.

The silicon cantilevers were coated with the amine-terminated alkylsilane, (3-Trimethoxysilylpropyl)diethylenetriamine (United Chemical Technologies, Bristol, Pa.) to promote cell adhesion and differentiation (Ravenscroft et al., 1998). Cantilevers were cleaned in serial acid baths of concentrated HCl in methanol (1:1 dilution) for 30 minutes and concentrated $H_2SO_4$ for 1 hour, followed by 30 minutes in boiling de-ionized water. Cleaned cantilevers were dried overnight in an 80° C. oven. Surface modification was performed according to a previously published protocol (Das et al., 2008). Briefly, the cantilevers were incubated in 0.1% solution of (3-Trimethoxysilylpropyl)diethylenetriamine in toluene for 30 minutes under gentle heating (approximately 70° C.), followed by 3× wash in fresh toluene. The coated cantilevers were then heated in fresh toluene for 30 minutes followed by drying overnight in an 80° C. oven. Coated samples were stored in a desiccator until use. X-ray photoelectron spectroscopy (XPS) and contact angle measurements were used to characterize the surface coating.

c. Fabrication of Piezoelectric Elements For Cantilevers

The skilled person in the art is familiar with piezoelectric microcantilever fabrication and function (see, e.g., Choudhury et al., 2007 and Datar et al., 2009). Piezoelectricity is the ability of certain materials (crystals and certain ceramics) to generate an electric potential in response to applied mechanical stress (Holler et al., 2007). The piezoelectric effect is used in various sensors to measure stresses or geometrical deformations in various mechanical devices. The reverse piezoelectric effect turns piezoelectric material into actuators, when an external voltage is applied to the crystal (King et al., 2000). Piezoelectric materials are known to the art and include, but are not limited to, the following: quartz, bone, sodium tungstate, zinc oxide, or lead zirconate titanate (PZT) (Lou 2009). A similar effect is the piezoresistive phenomenon. When subjected to mechanical stress, these materials change their resistivity (Mutyala et al., 2009).

Silicon wafers with silicon on insulator can serve as base material in the fabrication of piezoelectric cantilevers. An additional layer of 100-200 nm $SiO_2$ can be deposited onto the base material to insulate conductive materials from the semi-conductive silicon. Metal layers can be fabricated to connect the piezoelectric components with microelectronics. Layers of piezoelectric materials, such as ZnO and PTZ sol-gel, can be deposited exactly in those areas where microcantilevers remain after the etching process. Another conductive layer contacts the piezoelectric components from top to apply voltages for actuation or current read out during sensor mode. An insulation layer of silicon-ONO-stacks (oxide-nitride-oxide) can protect conductive elements from aqueous solutions during cell culture. Alternatively, piezoelectric elements can be replaced by piezoresistive materials. This alternative approach can offer a higher sensitivity during readout; however, piezoresistive materials do not provide the usage of the cantilevers as actuators and a field stimulator would be needed.

d. Fabrication of Microelectrode Array

Generally, the amount of information that could be obtained using traditional MEAs was limited. Not only contact interaction with the surface, but also the shape of the attachment area determines the physiology of cardiac myocytes. Pattern geometries determine the extent of the alignment of the long axis of cardiac myocytes, alignment determines CV and other physiological and pharmacological properties of cardiac tissues (Parker et al., 2008; Bourgeious et al., 2009; Badie et al., 2009). Therefore, in the experiments described herein, the cardiac myocytes were patterned on the top of the microelectrodes. In doing so, the measurement of conduction velocity along a well defined path became possible, which extended the capability of MEA measurements by including field potential (AP) length. Consequently, the amount of information that could be obtained using MEAs increased. As described herein, the incorporation of a functional cardiac system based on patterned cardiac cells integrated with MEAs enabled the measurement of conduction velocity, peak amplitude and spontaneous frequency, QT interval and relative refractory period (which is related to triangulation).

Cardiac myocytes cultured on microelectrode arrays (MEA) have several benefits compared to either traditional patch clamp electrophysiology or isolated organ methods. The use of MEAs in the investigation of cardiac side effects is more cost effective when compared to standard patch-clamp electrophysiology. Furthermore, cardiac myocytes can be maintained over longer periods of time on MEAs, thus chronic experiments can be feasible. Furthermore, in the system disclosed herein, the serum-free medium used in to culture the cardiac myocytes increases the reproducibility of the disclosed system.

Cardiac myocytes can be patterned on glass using photolithography following surface modification with self-assembled monolayers (SAMs) for myocytes (Dhir et al., 2009, Molnar et al., 2007). The benefit of this method is the compatibility of the technique with cheap automated silicon manufacturing steps and the ability of the cells to self-assemble after random plating. Self-assembled monolayers or SAMs are one molecule thick monolayers attached to a surface composed of organic molecules. Surface modification with SAMs is also compatible with advanced photolithography methods (Ravesncroft et al., 1998; Corey et al., 1991). Cells survive on patterned surfaces for extended periods of time (Das et al., 2008; Das et al., 2010), do not migrate off the patterned areas (Corey et al., 1991) and exhibit the typical morphology and physiology of the specific cell type (Das et al., 2004 Lochter et al., 1995).

MEA's containing sixty (60) electrodes (10 µm diameter) (Multichannel Systems, Germany) were cleaned by soaking the arrays in a detergent solution for 2 hours followed by sonication for 10 minutes. The arrays were then oxygen plasma cleaned for 20 minutes. Surface modification was completed by incubation of the MEAs in a 3 mM PEG silane, 2-[Methoxypoly(ethyleneoxy)propyl]trimethoxysilane (MW=460-590, Gelest), solution in toluene, with 37% concentrated HCl added to achieve a final value of 0.08% (0.8 mL HCl/L), for 45 minutes at room temperature. The arrays were then rinsed once in toluene, twice in ethanol, twice in water and sonicated in water for 2 minutes to remove the non-covalently linked material (Popat et al., 2004). The arrays were air dried with nitrogen and stored in a dessicator overnight.

The MEAs were patterned using a deep UV (193 nm) excimer laser (Lambda Physik) at a pulse power of 230 mW and a frequency of 10 Hz for 45 seconds through a quartz photomask (Bandwidth foundry, Eveleigh, Australia). The arrays were sterilized using 70% isopropanol and then incubated with 5 µg/mL of fibronectin in a phosphate buffered solution (Invitrogen) for 20 minutes at room temperature. The solution was removed and the surface was first rinsed with PBS, followed by the plating medium, and then dried before the cells were plated.

SAM-modified surfaces are characterized using XPS to demonstrate formation of the SAM and contact angle measurements to quantify wettability. Contact angle measurements are a rapid and simple measure of wettability. Contact angles are measured by application of static, sessile drops (5-30 µL) of deionized water to substrate surfaces with a micropipetter. The measurements are made visually on both sides of the drops using a Rame-Hart type goniometer. XPS is a technique for the elemental analysis and characterization of surfaces (Briggs 1992). Since the electrons of each clement possess characteristic binding energies, the energy pattern of emitted photoelectrons arising from a given element serves to unambiguously identify that element, while the precise peak positions, or chemical shifts, reflect the chemical environment (i.e., oxidation state) in which the element is found. XPS measurements are obtained on a FISONS 220i XL spectrometer. For each sample examined by XPS, a survey spectrum and high-resolution spectra for the elements Si, C, N, and any other clement that is unique to the SAM (F for 13F) was obtained. These measurements serve as (a) baseline quantities against which to contrast properties of the surface after cell culture, and (b) baseline quantities against which to contrast cell growth and survival from experiment to experiment for multivariate analysis.

e. Detection System Setup

Spontaneous or electrical stimulation-evoked force generation of cardiac myocytes was measured based on optical detection or electrical detection of cantilever-bending. Optical detection of displacement of the end of the cantilever was based on the principle routinely used in atomic force microscopes (AFM) in which a laser beam was reflected from the cantilever to a sensor. The sensor detected the displacement of the laser beam caused by changes in the position of the cantilever. In this optical detection method, an automated electrical shutter was placed in the beam path. This placement minimized the exposure of the cells to the reflected laser light. Electrical detection of the displacement was based on piezoelectric principle that requires special design and materials for the fabrication of the cantilevers. Both detection methods enabled automation and high-throughput screening on myocyte contraction force. Peak contraction force and force-contraction velocity relationships were calculated based on the geometry of the cantilevers and the thickness of cultured cardiac myocytes (determined from immunostaining data). Compounds (such as norepinephrine, epinephrine, ouabain, verapamil, and sotalol) were applied using traditional methods to the medium and possible changes in force or force-velocity relationship were detected and analyzed using standard statistical methods.

A detection system similar to those used in atomic force microscope (AFM) system was designed for measuring deflection of the cantilevers during contraction. The entire system was assembled around an upright Olympus BX51WI electrophysiology microscope (Olympus Inc., Center Valley, Pa.). The detection system consisted of a class 2 red photodiode laser (Newport, Irvine, Calif.), a stimulation chamber, a 4-quadrant photodetector (Noah Industries, Melbourne, Fla.), and a computer with pClamp 10.0 data acquisition software (Molecular Devices, Union City, Calif.). The laser and photodetector (PD) were mounted on x-y-z-h translators (Newport, Irvine, Calif.), which were mounted on the underside of the microscope stage. The stimulation chamber was fabricated from 5 mm thick polycarbonate sheet. An approximately 15 mm×15 mm square chamber was milled out of the sheet and fitted with silver wires (0.015 inch diameter) for field stimulation. The silver wires were mounted parallel to each other with a separation of 15 mm. The bottom of the chamber was sealed using a 22 mm×22 mm glass coverslip. This created a transparent base through which the laser beam could easily pass. The silver wires were connected to an external pulse generator (A-M systems, Sequim, Wash.) capable of producing field stimulation pulses of varying intensity, frequency, and waveform. Both the pulse generator and PD were connected to an Axon Instruments series 1440 digitizer (Molecular Devices, Union City, Calif.) which was interfaced with the computer.

The AFM system was calibrated using a modified version of the optical lever method. A bare microcantilever die, without cells, was placed in the stimulation chamber. The laser was focused on one of the microcantilevers and the PD was adjusted so that the laser fell on the diode surface. Using a digital volt meter to monitor the output voltage, the PD was adjusted so that the voltage being read was less than −7 volts. The PD was then moved vertically in 5 mm increments and the voltage recorded at each position. The results were plotted in Excel and a linear regression line was fitted to the linear region of the calibration curve, which was the region between −5 and 5 volts. The slope of this region was the detector sensitivity (ydetector). This value was used to calculate the angle, θ, of the deflection at the end of the microcantilever using the equation (Equation 1):

$$\theta = \frac{y_{measured}}{2\cos(\varphi)l \times y_{detector}} \quad (1)$$

where, y measured is the voltage measured from the PD, φ, is the angle of the detector to normal, and l, is the path length of the reflected laser beam.

Because of the large variability in the spring constants, cantilevers have to be further calibrated on an individual basis when used for precision force measurements. This variability is most likely caused by variations in thickness of the cantilever. Variability in the length and width is often quite small because typical lateral resolution in photolithography is on the submicrometer scale. For nominal spring constants greater than 0.1 N/m, the calibrated load displacement transducer of a nanoindenter can be used to measure the spring constant of each cantilever in an array. Measuring the resonance frequency of individual cantilevers and applying it to Sader's equation can provide detailed spring constants.

f. Multielectrode Extracellular Recordings

The cardiac myocytes were cultured on patterned metal MEAs (planar 10 μm electrodes, 200 μm separation, Multichannel-systems). A 60 channel amplifier (MEA1040, Multichannel-systems) was used to record electrical activity from the spontaneously beating cardiac cells. The same electrodes were also used for stimulation utilizing a stimulus generator (STG 1002, Multichannel systems). The cells were stimulated utilizing 500 mV, 1 ms wide bipolar pulses at 2 Hz. The recording medium was the same as the plating medium with the pH adjusted to 7.3 using HEPES buffer. After a 30 minute incubation period, APs were detected and recorded using built in functions of the Multichannel System software. For drug experiments, 50 μM 1-Heptanol (Gibco/Invitrogen) was added to the bathing medium and recordings were performed before and 15 minutes after drug administration with additional recordings done at 15 minute intervals. For Sparfloxacin (Sigma-Aldrich), 2 μM of the drug was added to the recording medium and recordings were taken in 15 minute intervals before and after drug administration. The data was further analyzed using software written using Matlab and Clampfit (Axon instruments).

g. Cell Culture

The serum-free medium comprised 100 mL Ultraculture medium (Bio Whittaker Cambrex) supplemented with 10 mL B27, 1 mL L-glutamine (Gibco/Invitrogen), 1 mL Penicillin Streptomycin, 0.375 g dextrose (Fisher Scientific) in 800 μL water, 1 mL non-essential amino acids and 1 mL of Hepes buffer (Gibco/Invitrogen) (Sathaye et al., 2006). Additional growth factors were also added to improve cell survival in the serum-free conditions. They included 0.1 μg/mL of L-thyroxine, 10 ng/mL of epidermal growth factor (Sigma-Aldrich) and 0.5 μg/mL of hydrocortisone (BD biosciences). Cells were plated at a density of 1000 cells/mm² on the MEAs. The medium was changed 24 hours after plating. Subsequent changing of the medium was performed every third day.

Human embryonic stem cell derived cell types including cardiomyocytes have been generated for pharmacology testing and toxicology screening. For example, GE markets cardiac myocytes. Before product release, each lot is highly characterized by flow cytometry, subcellular imaging, and electrophysiology. Each lot is demonstrated to express Gata4, Nkx2.5, MYH6/7, troponin I, aMHC and a-actinin, and negative for Oct4, TRA-1-81 and TRA-1-60. The cardiomyocyte population comprises ventricular, atrial, and nodal subtypes and has been documented to have an adult phenotype.

h. Immunostaining

Patterned cardiac myocytes can be immunostained. In a set of experiments, the patterned cardiac myocytes were immunostained for F-Actin with Rhodamine Phalloidin (Invitrogen, R415) using a protocol provided by the company. Briefly, the cells were washed with PBS and fixed using 3% Formaldehyde. The coverslips were extracted with 0.1 mL Triton X®. The staining solution (with 1% Bovine Serum Albumin to prevent background staining) was added at a dilution of 1:40 in PBS and coverslips were incubated for 30 minutes. Imaging was done using confocal microscopy.

ii) Experiment 1

In the experiments described herein, the integration of human cardiac myocytes into the two devices was achieved. The surface of the glass microelectrode arrays (MEAs) were coated with polyethylene-glycol (PEG) self-assembled monolayers (SAMs), which were then patterned with a 193 nm deep-UV excimer laser through a quartz photomask. The MEAs were incubated with fibronectin to create an attachment surface for the cardiac myocytes. The silicon cantilevers were treated with fibronectin. Human embryonic stem cell derived cardiac myocytes, which were obtained from a commercial source (GE), formed a monolayer on the surface of the two devices. The human derived cardiac myocytes displayed adult-like characteristics as verified by immunohistochemistry and electrophysiological and pharmacological experiments. Here, the cells differentiated to spontaneously contracting cardiac myocytes and showed stable activity for longer than a month.

Figure 25A:
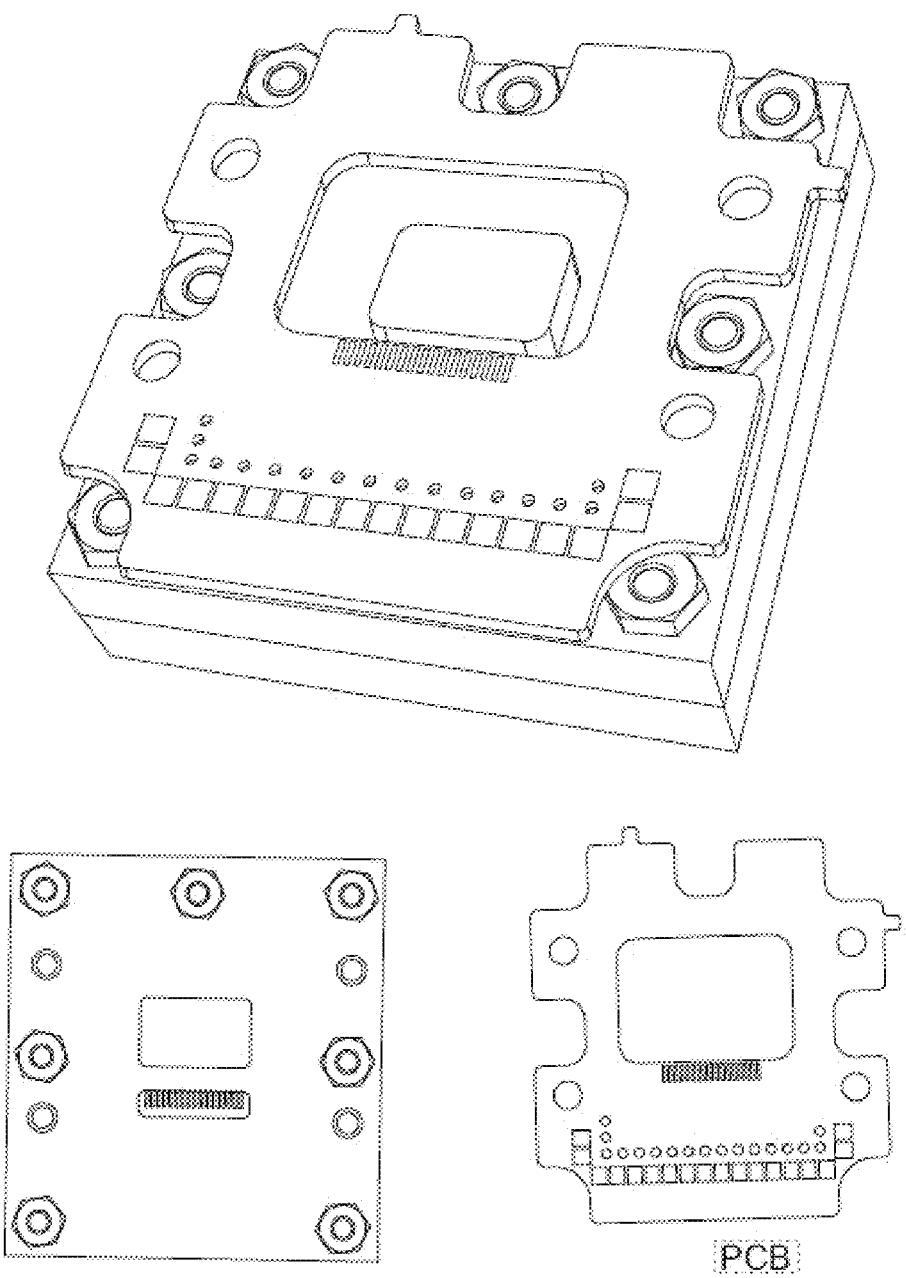
FIG. 25A shows representative images of a disclosed device (both panels) (e.g., "hybrid systems laboratory" or "HSL").
Figure 25B:
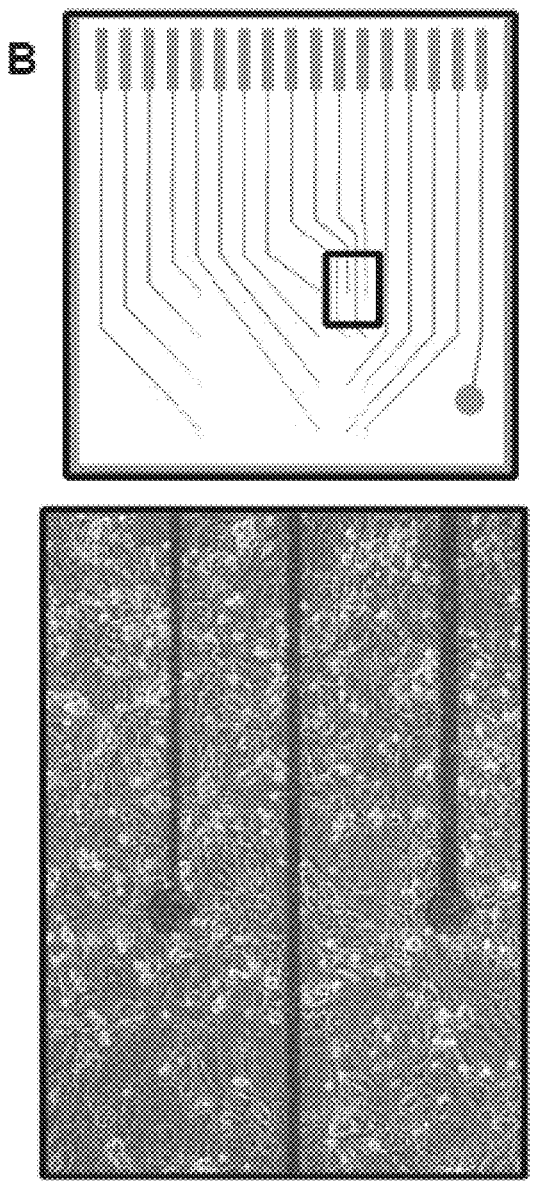
FIG. 25B shows a schematic of MEA chip (top panel) and a light micrograph of integrated cardiomyocytes 6 days in vitro (derived from human IPSCs) cultured on MEAs (bottom panel).
Figures 25C, 25D:
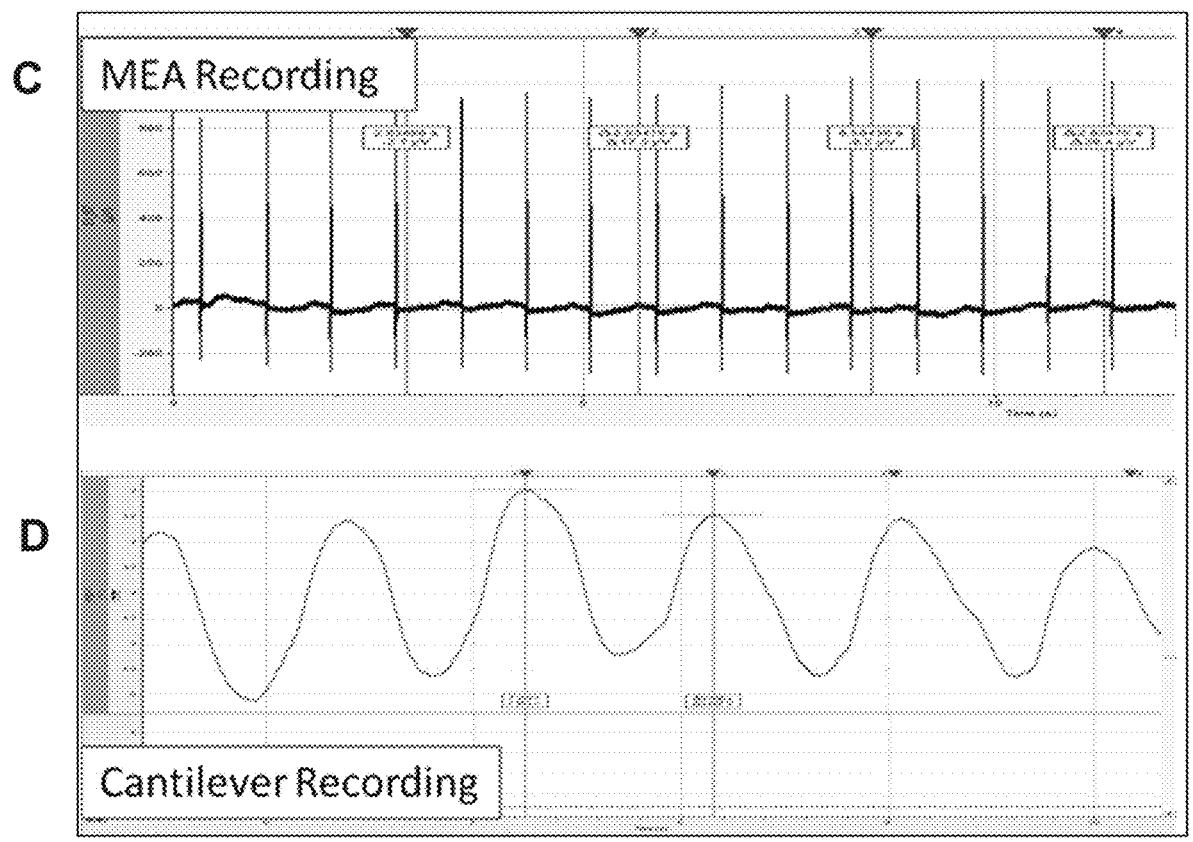
FIG. 25C shows a representative MEA recording of integrated cardiomyocytes 7 days in vitro using the device shown in FIG. 25A.
FIG. 25D shows a representative cantilever recording of integrated cardiomyocytes 7 days in vitro using the device shown in FIG. 25A.

For example, as shown in FIG. 25A, a disclosed device (which can also be referred to as a "hybrid systems laboratory" or "HSL") was comprised of the following components: a chip (a microelectrode array chip), a polycarbonate housing (bottom and top plates), two silicone gaskets, a printed circuit board (PCB), and a commercially available elastomeric connector. In FIG. 25A, the chip was made of fused silica and measured 15 mm×15 mm. Seventeen (17) titanium/platinum microelectrodes were microfabricated on the surface of the chip for measurements of the electrical activity of the cardiomyocytes plated on the chip surface. The MEA chip was placed between the two polycarbonate plates that were clamped together with screws. The silicone gaskets, placed between the polycarbonate plates and the cMEA chip, ensured tight sealing of the module. Two apertures were provided on the top polycarbonate plate. One aperture was used to access the portion of surface of the chip in which cardiomyocytes were plated and to perform medium changes. The other aperture provided access the contact pads of the chip microelectrodes. The PCB was placed on the top of the housing. Electrical contact between the cMEA chip and the PCB was made via an elastomeric connector placed in the aperture on the polycarbonate plate. Recording of the cardiomyocytes electrical activity were performed connecting the PCB to the Microelectrode Array System (Multichannel System). Data generated by integrated cardiomyocytes using the device are shown in FIG. 25C (field potential recordings via MEA) and FIG. 25D (force contraction recordings via cantilevers).

Figure 25E:
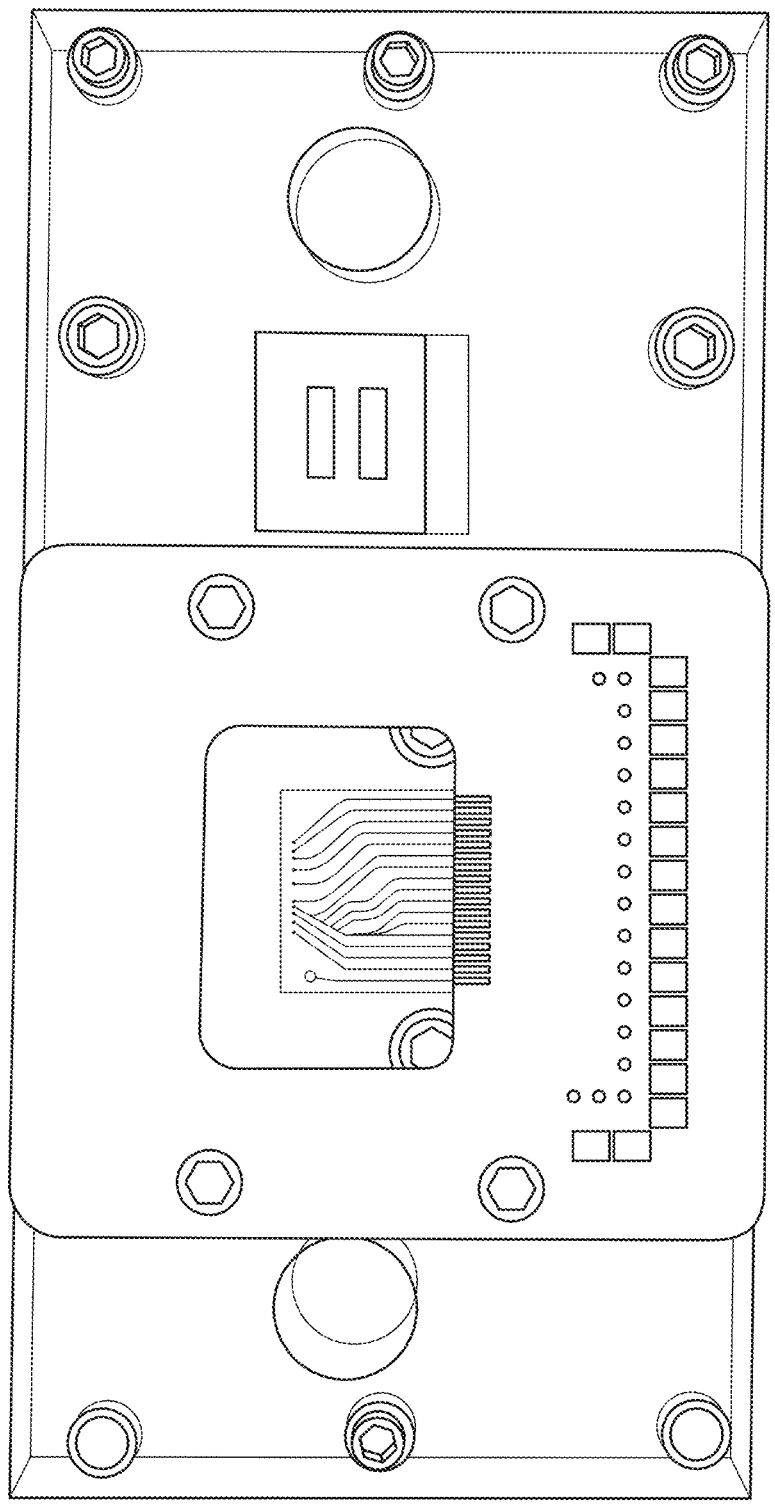
FIG. 25E shows a representative image of a disclosed device comprising all the components of the device shown in FIG. 25A and a cantilever chip for measuring the contractile force of the cultured cardiomyocytes.
Figures 26A, 26B:
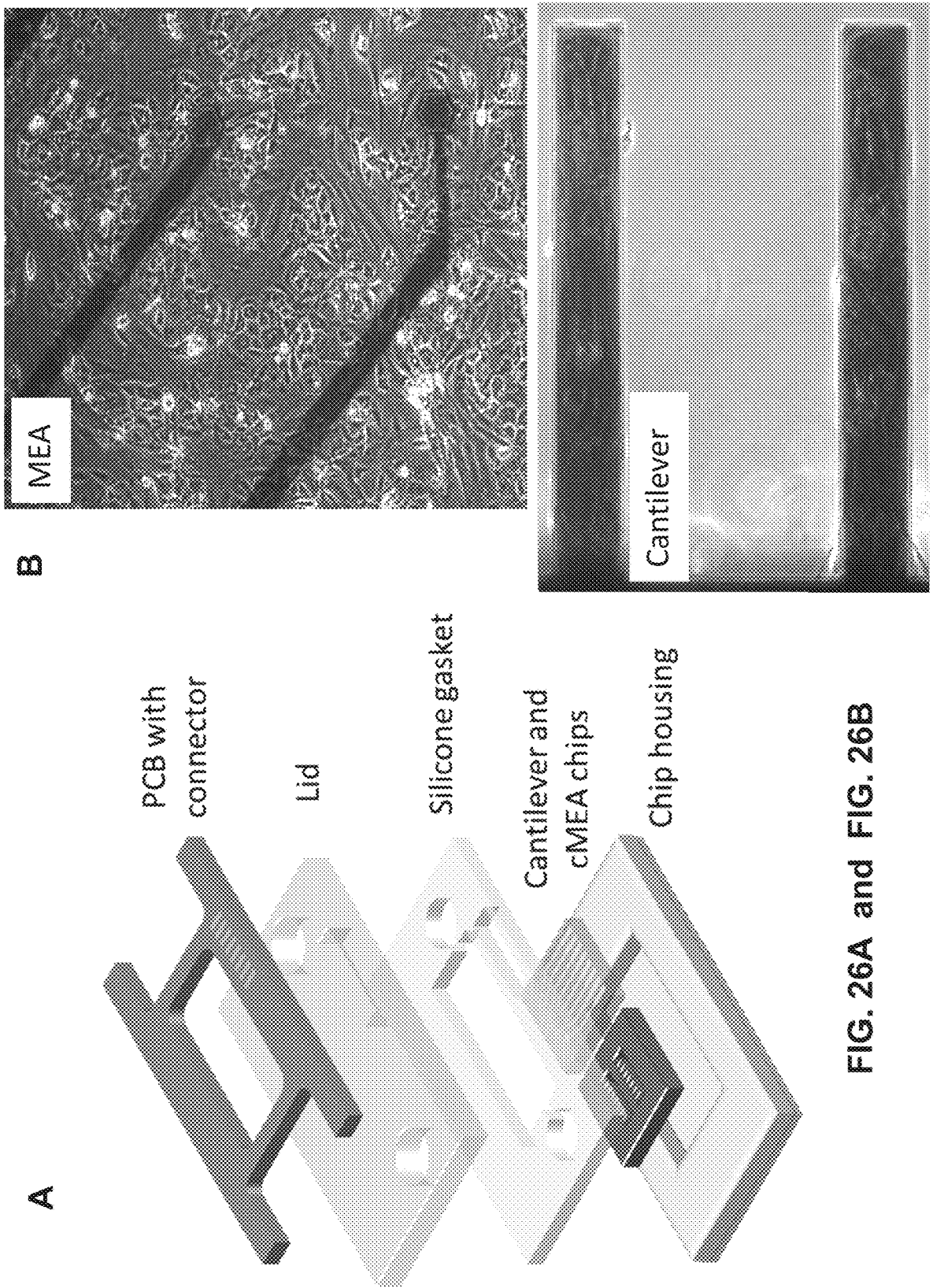
FIG. 26A shows the components of a representative disclosed device comprising both a cantilever chip for measuring contractile forces of cardiomyocytes and a MEA chip for measuring electrical activity of cardiomyocytes.
FIG. 26B shows an image of a cardiomyocytes cultured on an MEA for 2 days (top panel) and an image of cardiomyocytes cultured on cantilevers for 2 day (bottom panel).
Figure 27:
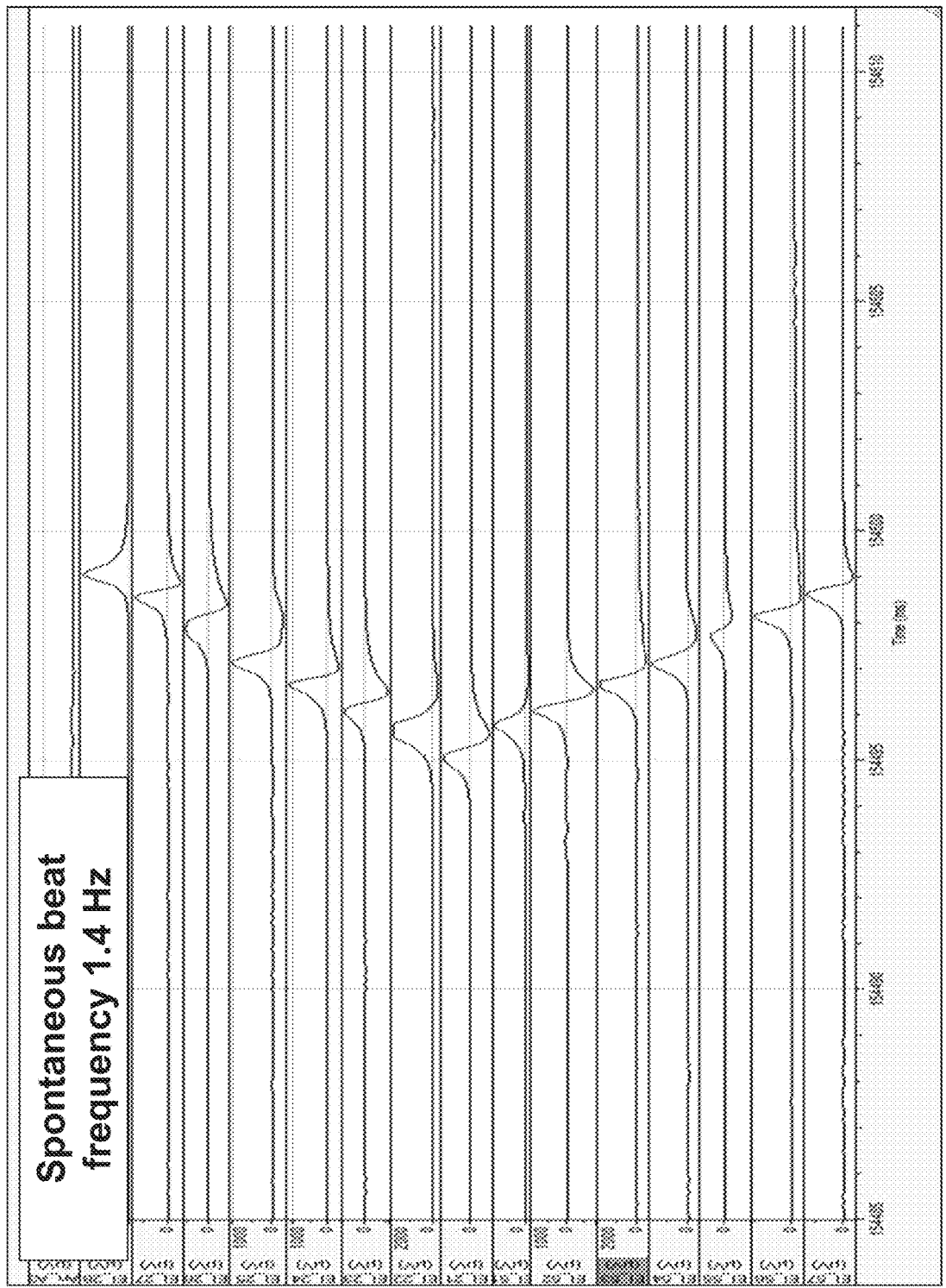
FIG. 27 shows the field potential of spontaneously beating cardiomyocytes (derived from human iPSCs) cultured on an MEA.
Figure 28:
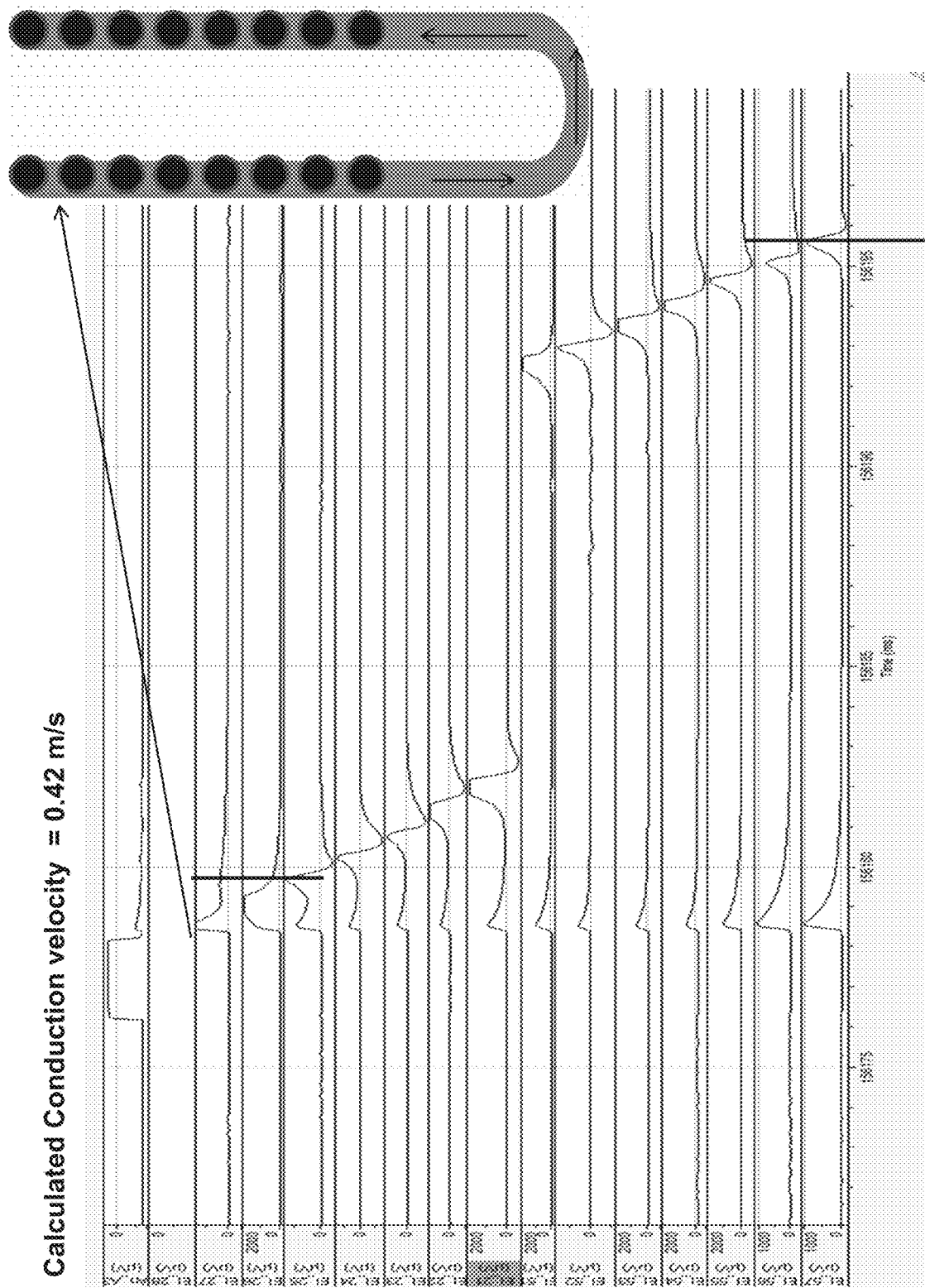
FIG. 28 shows measurement of conduction velocity for cardiomyocytes (derived from human iPSCs) cultured on an MEA following electrical stimulation (at 500 mV, 2 Hz) propagated along the long loop pattern schematically represented to the right.

FIG. 25E shows an expanded version of the HSL in which the device comprises a cantilever chip for measuring the contractile forces of the cultured cardiomyocytes (see also, schematic shown in FIG. 26A). The cardiomyocytes used in these experiments were derived from differentiated adult induced pluripotent stem cells purchased from Cellular Dynamics. In FIG. 27 and FIG. 28, the electrical activity of the human cardiomyocytes plated on patterned MEAs was recorded following 12 days in vitro using a Multichannel Systems 60 channel amplifier (MEA 1040, Multichannel Systems). Prior to recording, the cells were allowed to equilibrate for 15 min in the lab atmosphere at 37° C. Temperature was maintained with a TC02 temperature controller (Multichannel Systems). The cells were stimulated using a STG 1002 stimulator (Multichannel Systems) by applying 1 ms wide bipolar square pulses of 500 mV every 500 ms. The recording medium was the same as the plating medium. In FIG. 28, the electrical stimulus was applied on the electrode located at the end of the loop (channel 28). Conduction velocity was calculated as distance divided by the time difference between the recorded peaks.

A disclosed system can be used to assess or evaluate the effects on cardiac parameters and/or cardiac outcomes generated by at least, and without limitation, the following: metabolic inhibitors, nutritional supplements, therapeutic compounds, compositions, and drugs, investigational compounds, compositions, and drugs, biosimilars, agonists, antagonists, hormones, growth factors, small molecules, monoclonal antibodies, and combinations thereof. For example, in the examples discussed below, several compounds were selected for use in the disclosed system. These compounds were selected, in part, because of an ability to affect specific cardiac parameters (See, for example, FIG. 29 and FIG. 30A-30D).

Figure 29:
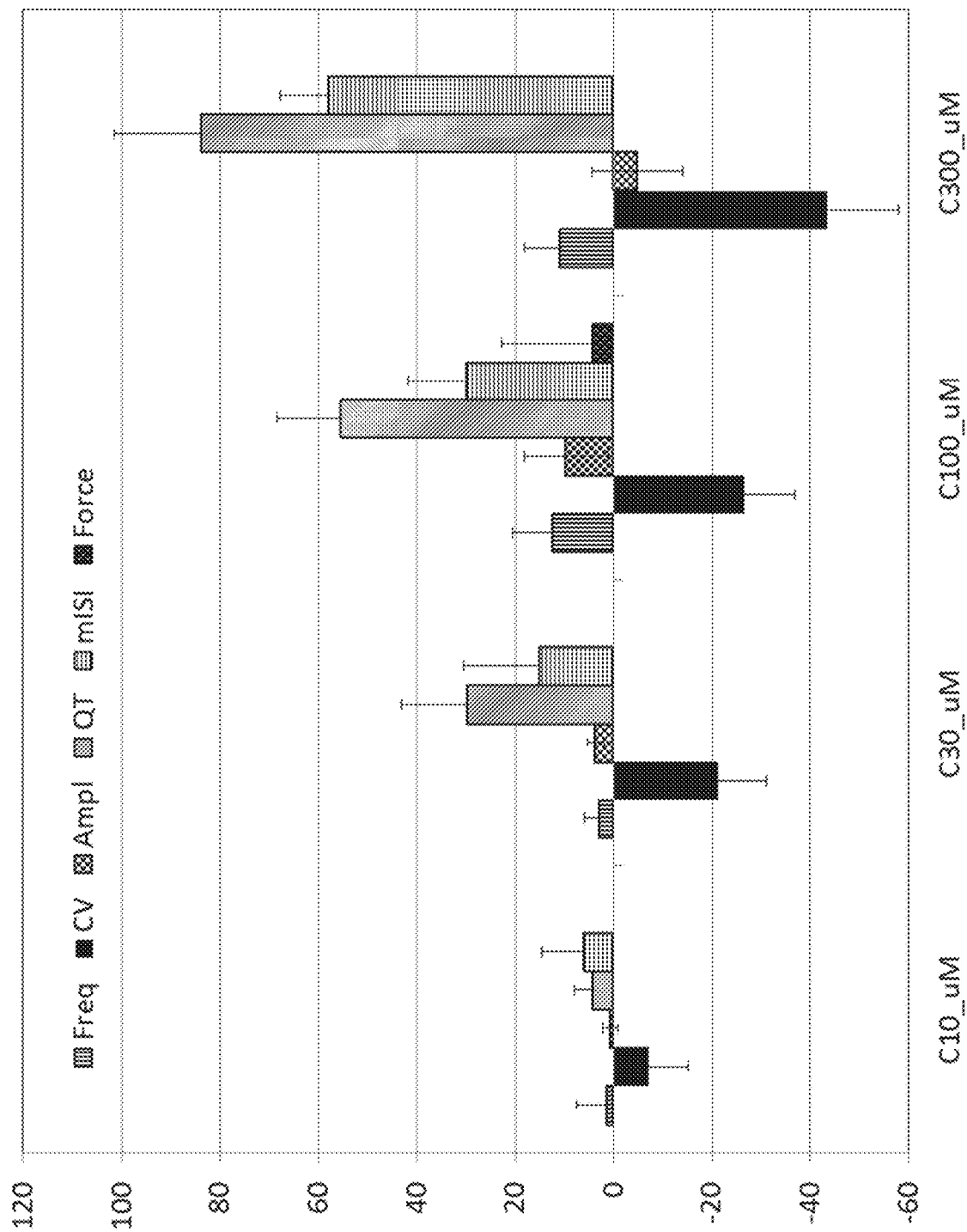
FIG. 29 shows the effect of sotalol on various cardiac parameters of cardiomyocytes (derived from human iPSCs) cultured for 12 days on an MEA.

In the disclosed system, sotalol significantly increased QT intervals and mISI parameters. However, sotalol concentrations above 100 µM concentrations decreased conduction velocity. Thus, sotalol affected the measured cardiac parameters in a unique and characteristic way (i.e., created a "fingerprints") according to its mechanism of action and physiological effects. For example, in FIG. 29, several cardiac parameters were measured including frequency (Freq), conduction velocity (CV), field potential amplitude (Ampl), QT interval, minimum interspike interval (mISI), and peak contraction force. Data are represented as percentage changes compared to the control and expressed as mean +/−SEM. In FIG. 29, electrical activity of the human cardiomyocytes plated on patterned MEAs was recorded following 12 days in vitro (DIV) using a Multichannel Systems 60 channel amplifier (MEA 1040, Multichannel Systems). Prior to recording, the cells were allowed to equilibrate for 15 min in the lab atmosphere at 37° C. Temperature was maintained with a TC02 temperature controller (Multichannel Systems). The cells were stimulated using a STG 1002 stimulator (Multichannel Systems) by applying 1 ms wide bipolar square pulses of 500 mV every 500 ms. The recording medium was the same as the plating medium. Sotalol (Sigma, cat#S0278) was added to the bathing medium in increasing concentrations of 0 µM, 10 µM, 30 µM, 100 µM, and 300 µM.

In the disclosed system, norepinephrine significantly increased spontaneous beating rate, decreased QT interval (and it analogue minimal ISI), and increased peak contraction force of human cardiac myocytes in the concentration range of 0.1-3 µM. Thus, norepinephrine affected the measured cardiac parameters in a unique and characteristic way (i.e., created a "fingerprints") according to its mechanism of action and physiological effects (FIG. 30A).

In the disclosed system, verapamil concentration dependently decreased contraction peak force. Thus, verapamil affected the measured cardiac parameters in a unique and characteristic way (i.e., created a "fingerprints") according to its mechanism of action and physiological effects (FIG. 30D).

In FIG. 30A-FIG. 30D, which also shows the effect of ouabain (C) and epinephrine (B) on contractile force, the contractile stress of human cardiomyocytes plated on cantilevers was recorded following 14 day in vitro. A detection system similar to that used in atomic force microscopy (AFM) was used in these experiments. Prior to recording, the cells were allowed to equilibrate for 15 min in the lab atmosphere at 37° C. Drugs were added cumulatively as follow: 0.1 µM, 0.3 µM, 1.0 µM, and 3.0 µM (norepinephrine); 0.1 µM, 1.0 µM, and 3.0 µM (epinephrine); 0.1 µM, 0.3 µM, 1.0 µM, and 3.0 µM (ouabain); and 0.3 µM, 1.0 µM, and 3.0 µM (verapamil). Washout was performed by rinsing the cells five (5) times with 1 mL of cell culture medium.

Thus, the effects on action potential (AP) length (analog to the QT interval on the EEG recordings) and AP shape can be used in in vivo and ex vivo cardiac screens to predict arrhythmogenic effects of drugs.

Figure 31D:
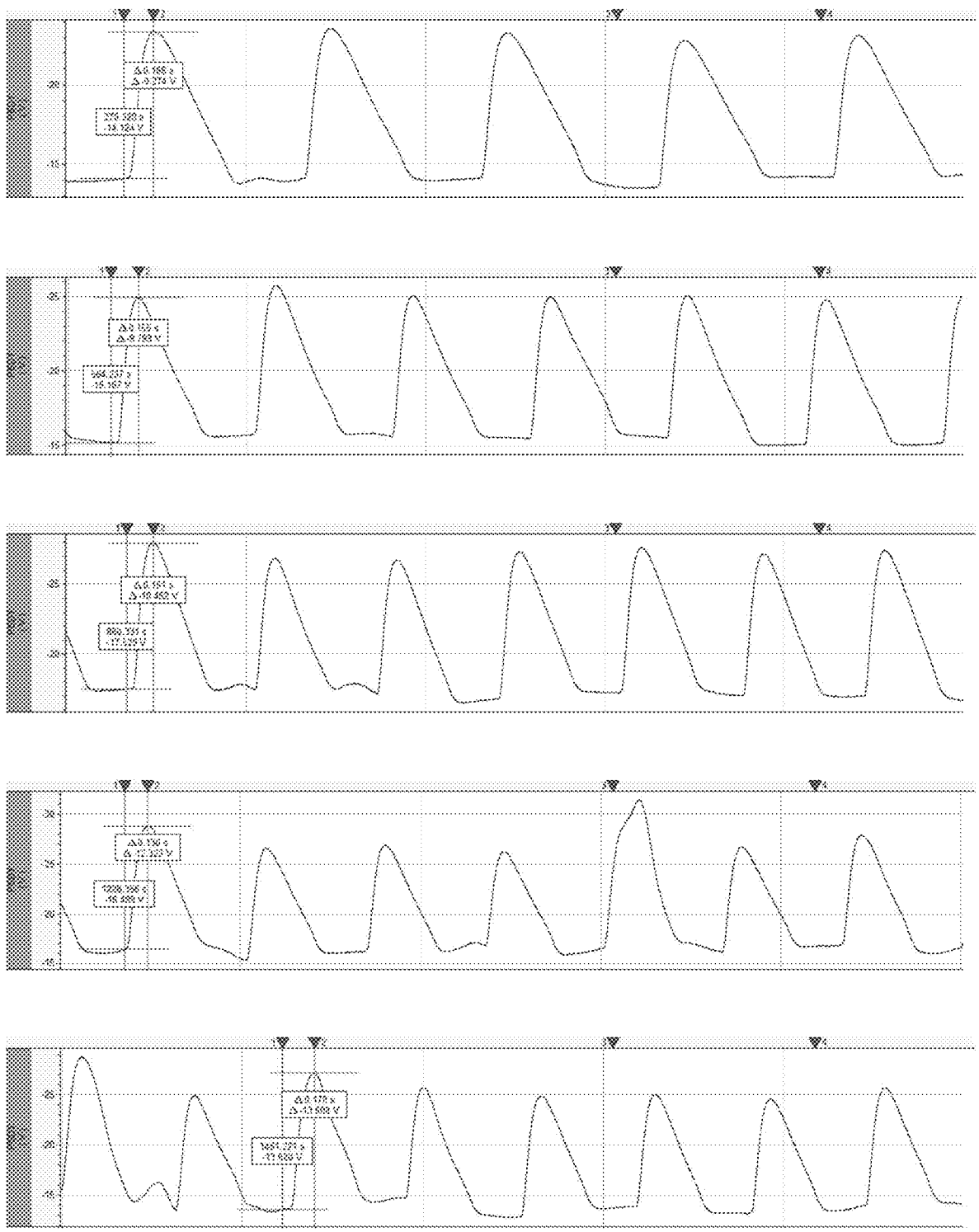
FIG. 31D shows that cardiomyocytes cultured on cantilevers respond to norepinephrine by increasing contractile force and contractile frequency.

FIG. 31A-FIG. 31D provide data relating to the functional characterization of cardiomyocytes derived from human iPSCs cells. In FIG. 31B, whole-cell patch clamp recordings were performed with an Axioscope FS2 upright microscope (Carl Zeiss, Gottingen, Germany). Cells were perfused with extracellular solution containing NaCl 140 mM, KCl 5 mM, $MgCl_2$ 1 mM, $CaCl_2$ 2 mM, D-Glucose 10 mM, and HEPES 10 mM. The pH was adjusted to 7.4 and the osmolarity was 330 mOsm. The intracellular solution was composed KCl 140 mM, NaCl 4 mM $CaCl_2$ 0.5 mM, $MgCl_2$ 1 mM, EGTA 1 mM HEPES 10 mM, and $Na_2ATP$ 5 mM. Patch pipettes were prepared from borosilicate glass (BF150-86-10; Sutter, Novato, Calif.) with a Sutter P97 pipette puller. Pipette resistance was 4-6 MOhm for intracellular patch clamp recordings. Voltage clamp and current clamp recordings were performed with a Multiclamp 700B amplifier (Axon Instruments, Foster City, Calif., USA). Signals were filtered at 2 kHz and digitized at 20 kHz with an Axon Digidata 1322A interface.

For stimulation experiments shown in FIG. 31C square electrical stimuli, 40 ms wide, 4-5 V in amplitude were applied with varying frequencies ranging from 0 to 10 Hz via an isolated pulse stimulator (A-M Systems, Sequim, Wash.). Prior to recording, the cells were allowed to equilibrate for 15 min in the lab atmosphere at a temperature of 37° C. maintained by a Delta T4 culture dish temperature controller (Bioptechs, Butler, Pa.).

iii) Experiment 2

Figure 5A:
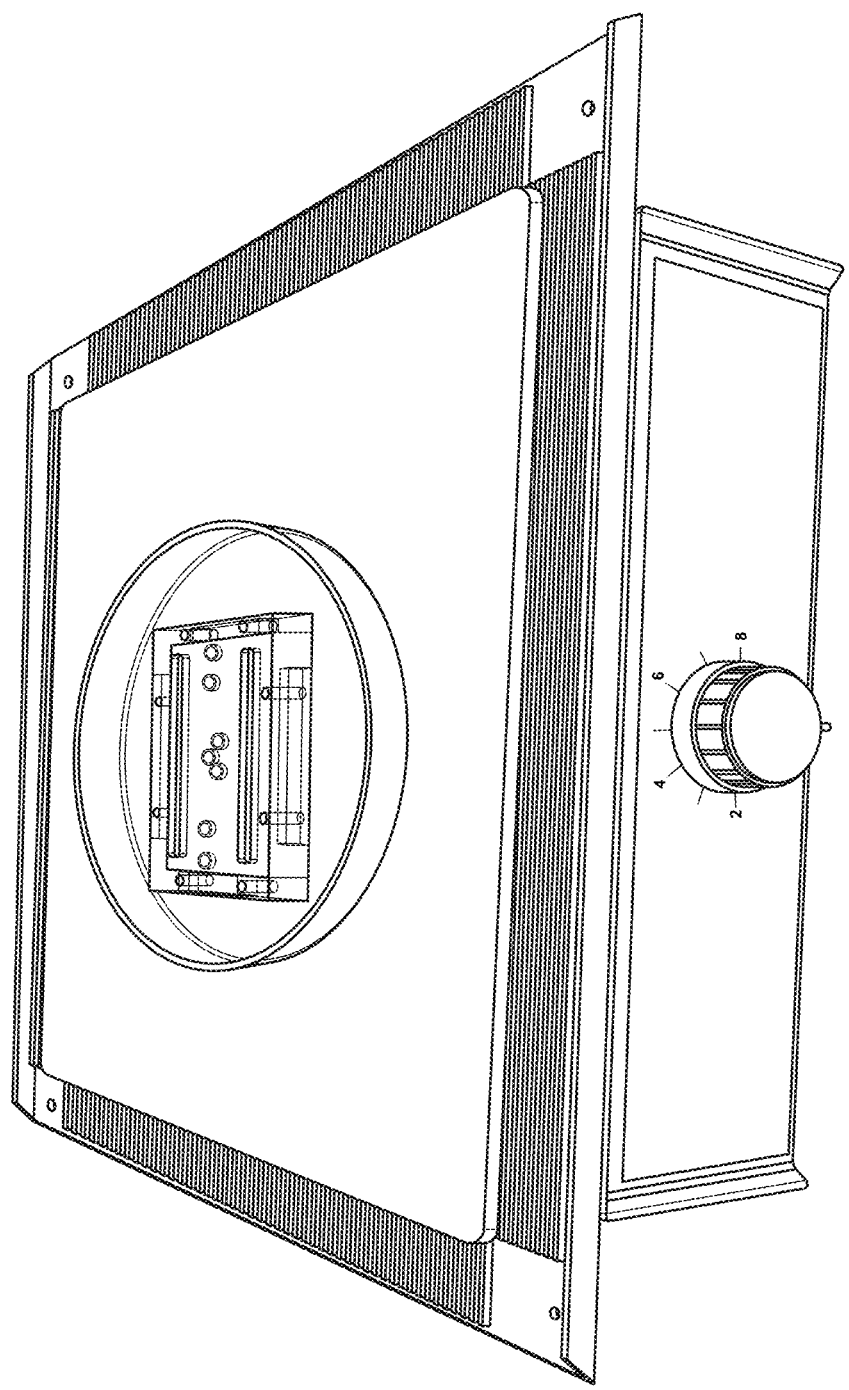
FIG. 5A shows an image of the multichamber device on a rocker platform (e.g., a 10 organ chip system).
Figure 5B:
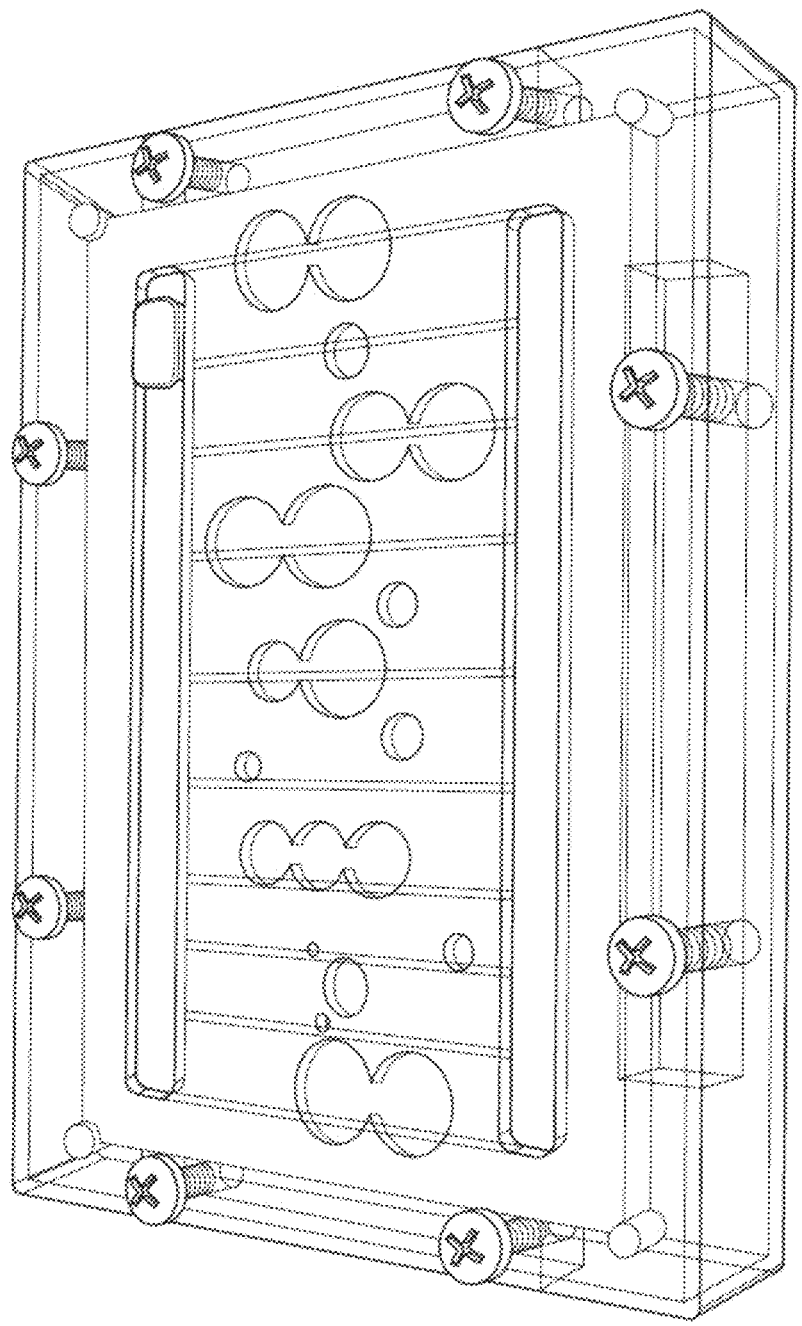
FIG. 5B shows an enlarged image of the multichamber device shown in FIG. 5A.

A low cost, easy to use platform to emulate human response to drugs and chemicals with 10 organ systems was constructed. The platform is "pumpless" and uses a rocker platform and gravity for the fluid motion force (FIG. 5A-5B). Since many units can be placed on a rocker platform and platforms can be stacked (FIG. 6), the system can be used for moderately high throughput studies. Studies have demonstrated that a platform can be constructed that is operational and can sustain viable cell cultures of HepG2/C3A cells in all compartments for at least 48 hours. Studies with dyes and without cells demonstrate appropriate transfer across polymeric membranes in compartments (e.g., the blood brain barrier). The mixing time to achieve near equilibrium in the system corresponds to physiologic values. The initial characterization studies indicate that such a platform system is feasible.

Figure 6:
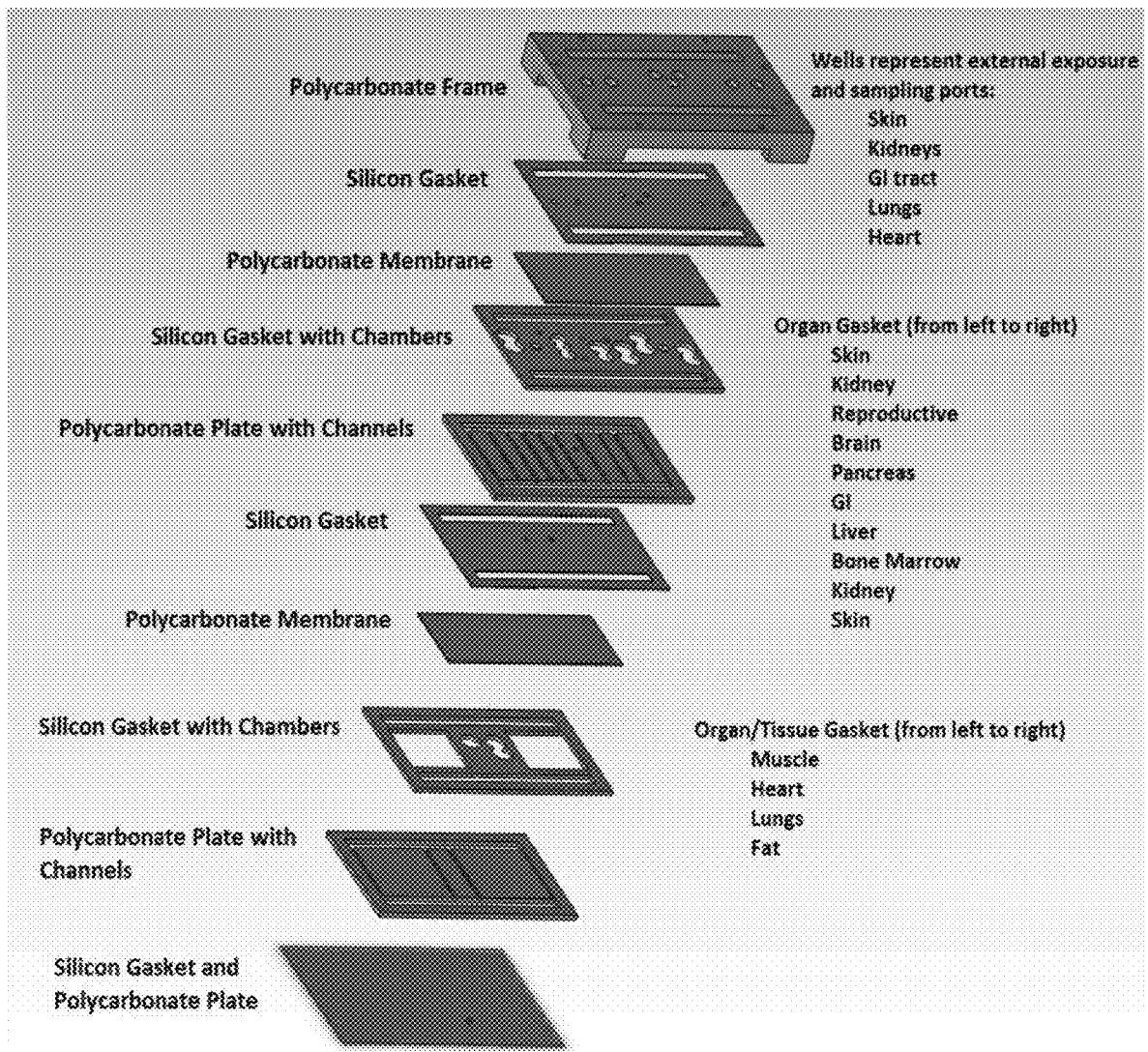
FIG. 6 shows an expanded view of a representative multichamber device, listing exemplary components of the device and exemplary tissues, cells, and/or organs for use in the device.

The "pumpless" cell culture platform is a multichamber device on a rocker platform made from silicone sheets and a polycarbonate frame (see, e.g., FIG. 5A, FIG. 5B, and FIG. 6). It is produced at a low cost and is easy to modify, easy to implement (rapid set-up and minimal operator training). The low cost format is due to no pump, multiple units on a rocker platform, and optical and electrical access. The platform has a robust operation that includes no gas bubbles, removes tubing that causes dead volumes and unphysiologic absorption, and no moving parts to fail. The platform can be highly predictive of human response and has a ratio of organ sizes, residence time of blood surrogate, removal of samples from blood surrogate, and the flow to each organ are physiologic.

When Hep G2/C3A cells were placed in each chamber all cell cultures retained high viability (85 to 95%) in a two day test. This test confirmed that this system provided sufficient delivery of oxygen and nutrients while emulating human physiology. Using a dye, flow pattern was as expected from the PBPK simulation; overall fluid turnover was physiologic. UH3 can populate a similar device with appropriate tissue mimics, electric connections, and fluid samplers. Other tissue mimics can be integrated with the current system design.

HepG2/C3A cell lines were used to demonstrate the ability to use the RegeneMed cell culture scaffold within the pumpless platform. Liver cells were co-cultivated with non-parenchymal cells for 14 days in dynamic conditions and showed a positive induction of CYP1A1 and CYP3A4 enzyme activity. The liver and the gastrointestinal tract can both be studied using the pumpless cell culture platform (see FIG. 13, FIG. 14B, FIG. 15A-FIG. 15D, and FIG. 16A-FIG. 16F).

Figure 7:
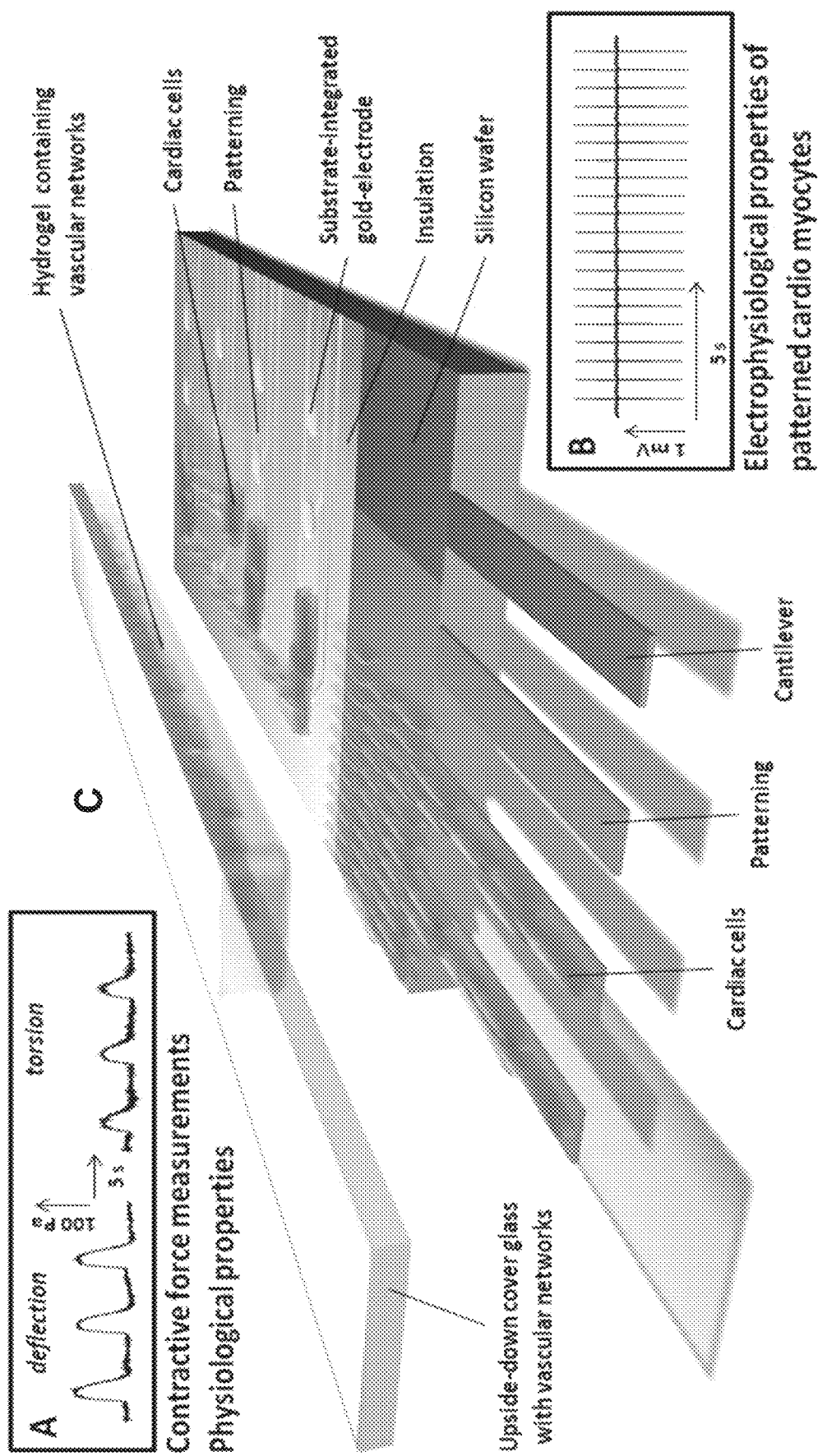
FIG. 7A shows how the disclosed system measures contractive force of patterned cardiomyocytes.
FIG. 7B shows how the disclosed system measures electrophysiological properties of patterned cardiomyocytes.
FIG. 7C shows a schematic of disclosed integrated system.
Figure 8:
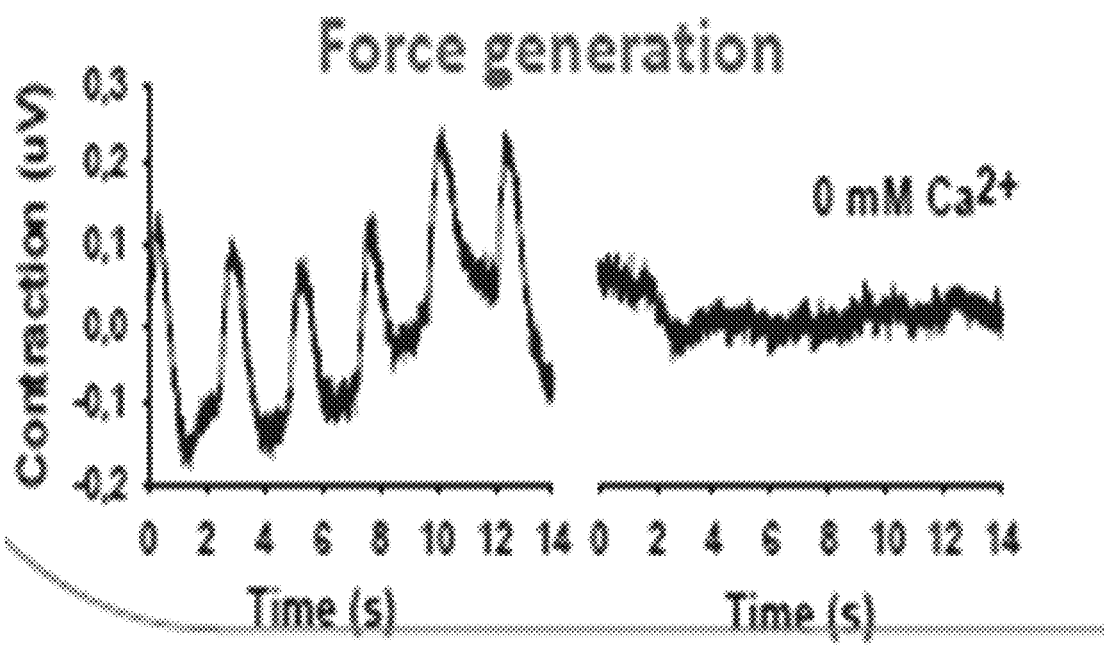
FIG. 8 shows the force generation (presented as contraction (uV) versus time (s)) of cardiomyocytes before (left panel) and after (right panel) addition of $Ca^{2+}$.
Figure 9:
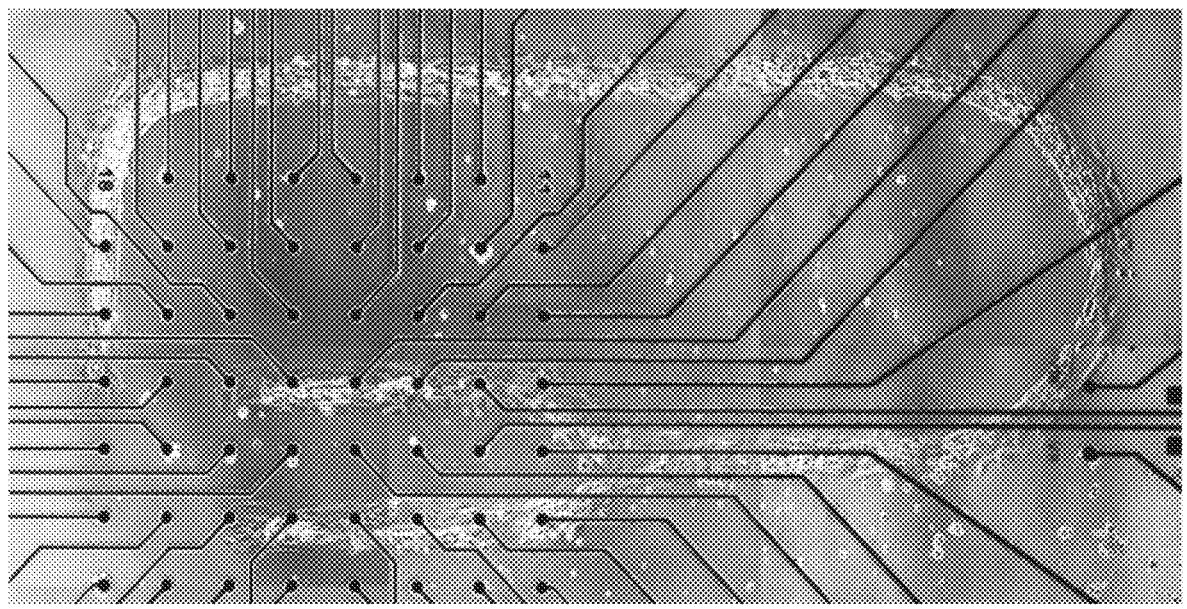
FIG. 9 shows an image of a patterned microelectrode array (MEA).
Figure 10A:
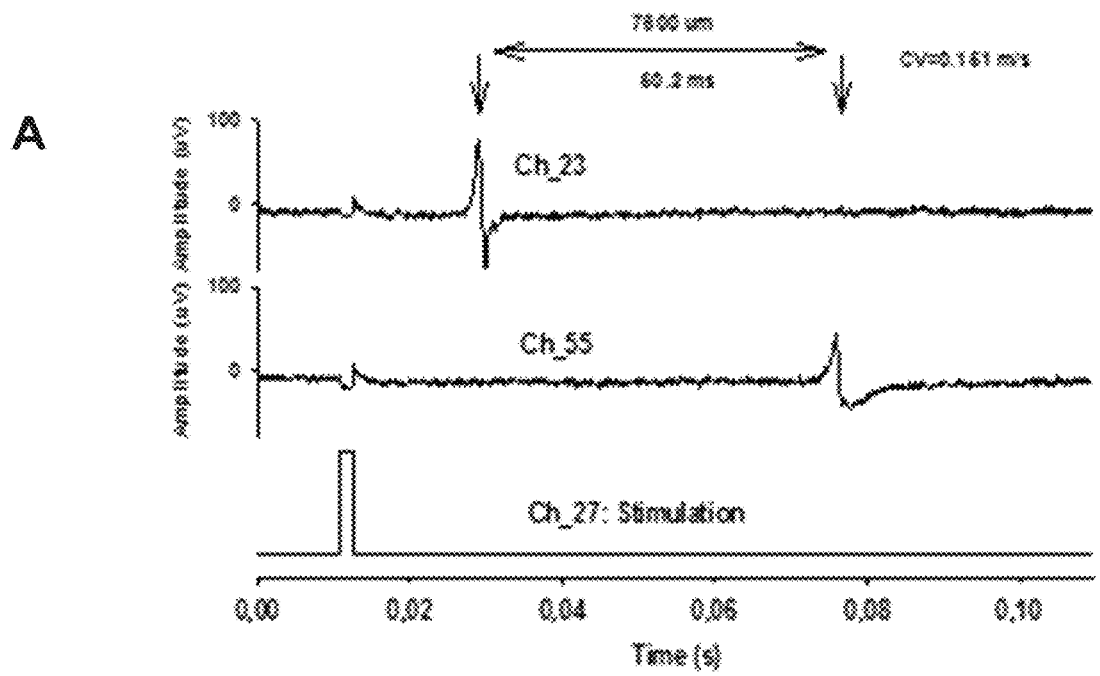
FIG. 10A shows the effect of norepinephrine on the conduction velocity of human cardiomyocytes.
Figure 10B:
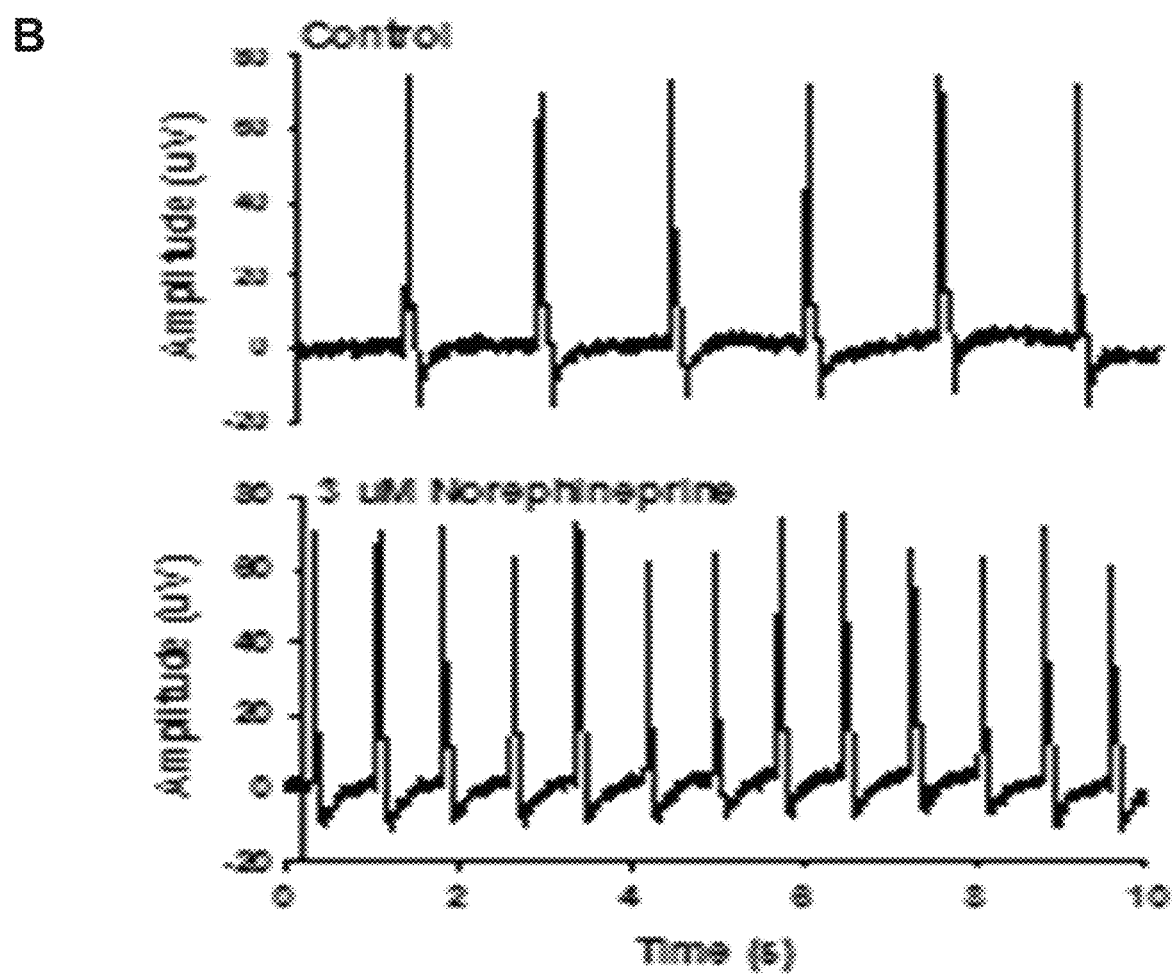
FIG. 10B shows the effect of norepinephrine on rhythm generation of human cardiomyocytes as compared to control.
Figure 10C:
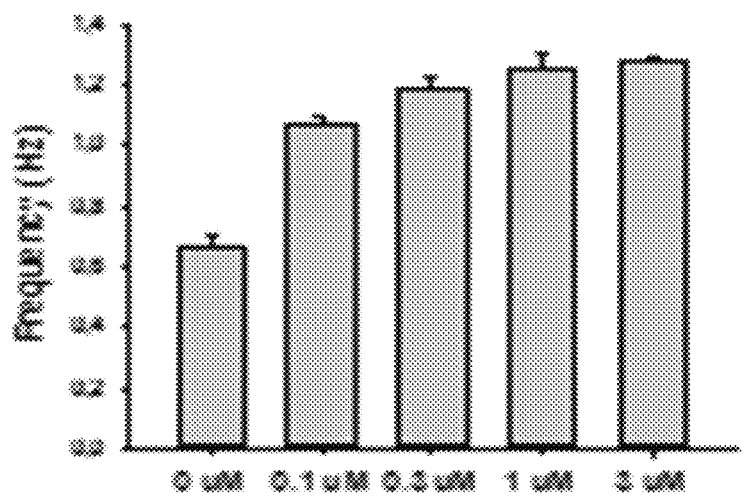
FIG. 10C shows a bar graph representing frequency (Hz) versus concentration of norepinephrine.
Figure 10D:
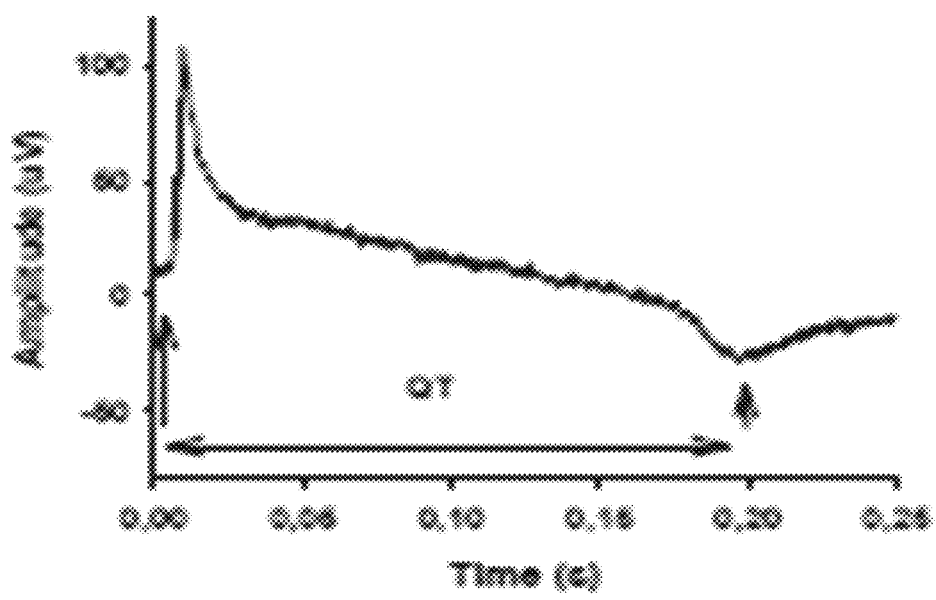
FIG. 10D shows the effect of norepinephrine on QT interval of human cardiomyocytes.
Figures 12A, 12B:
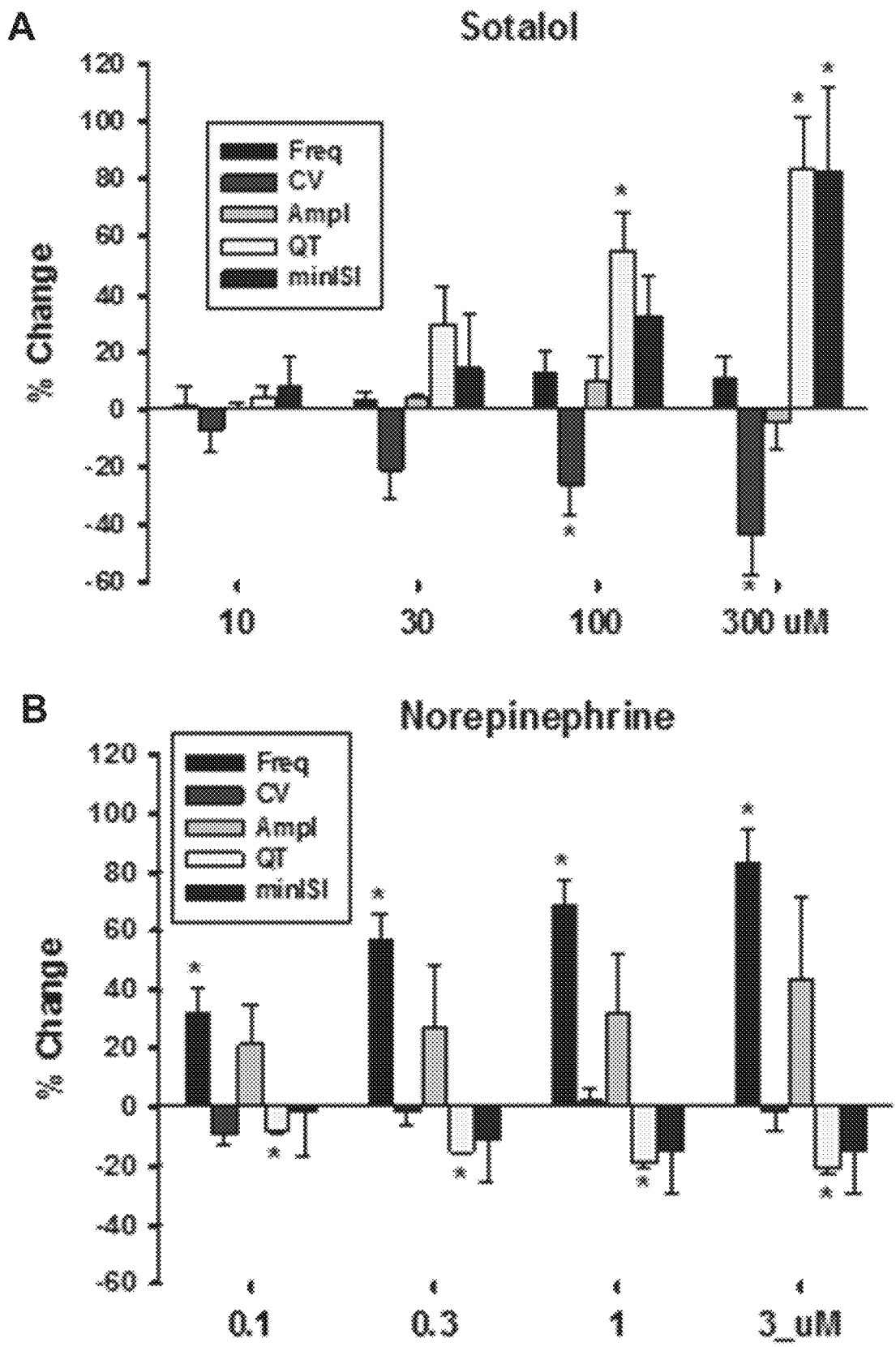
FIG. 12A shows a bar graph demonstrating % change versus concentration (μM) of sotalol.
FIG. 12B shows a bar graph demonstrating % change versus concentration (μM) of norepinephrine.
Figure 12C:
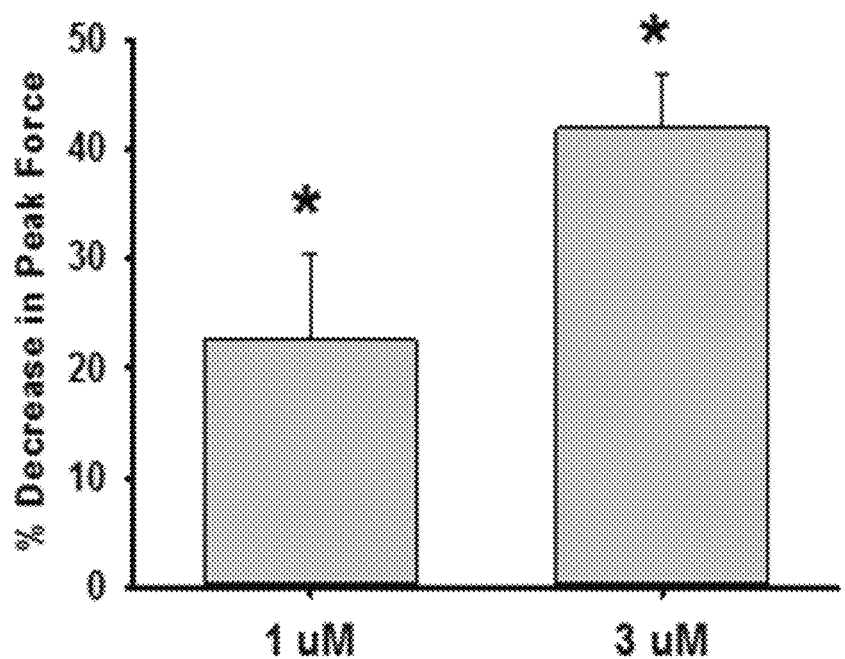
FIG. 12C shows a decrease in peak force versus concentration (μM) of human cardiomyocytes following administration of verapamil.
Figure 13:
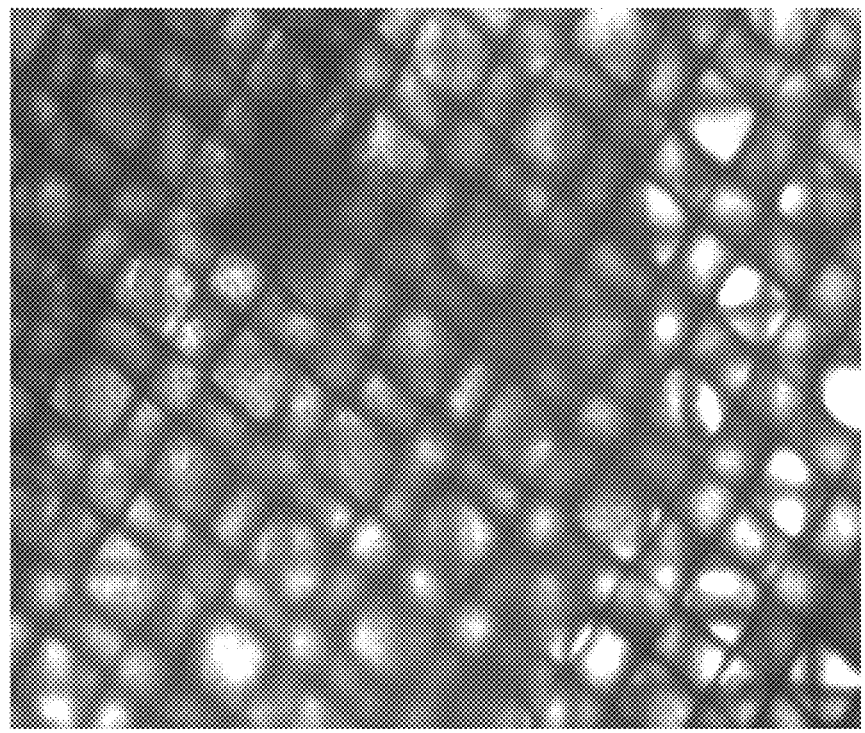
FIG. 13 shows the co-culture of liver cells (HepG2/C3A) and non-parenchymal cells within the RegeneMed scaffold inside the pumpless cell culture platform.
Figure 14A:
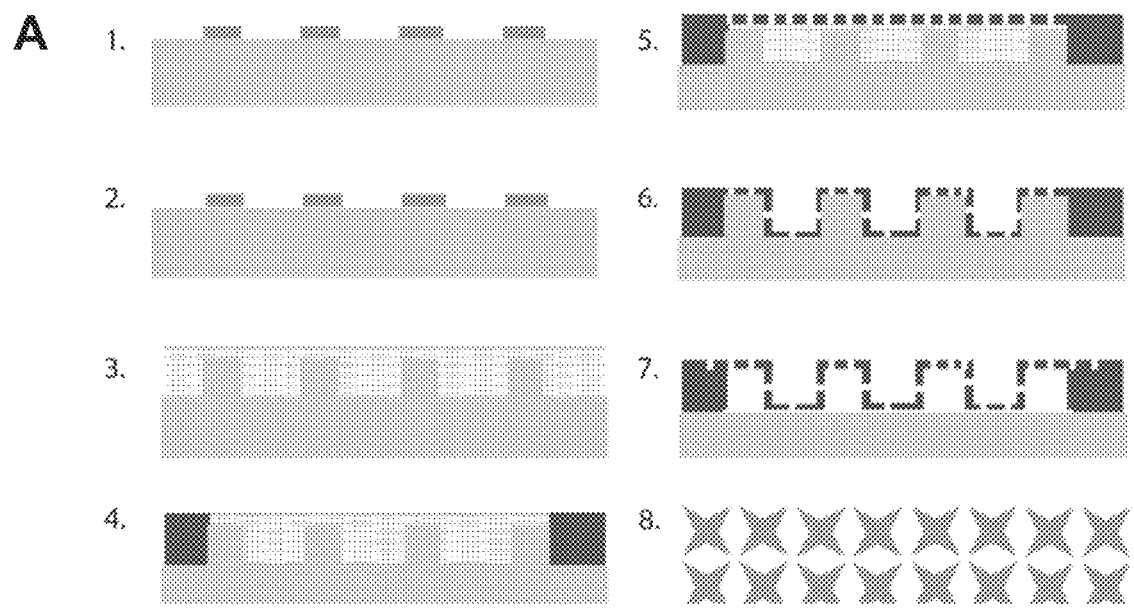
FIG. 14A shows examples of cell cultures on microfabricated membranes, specifically the fabrication of 3D membranes with macrovilli.
Figure 14B:
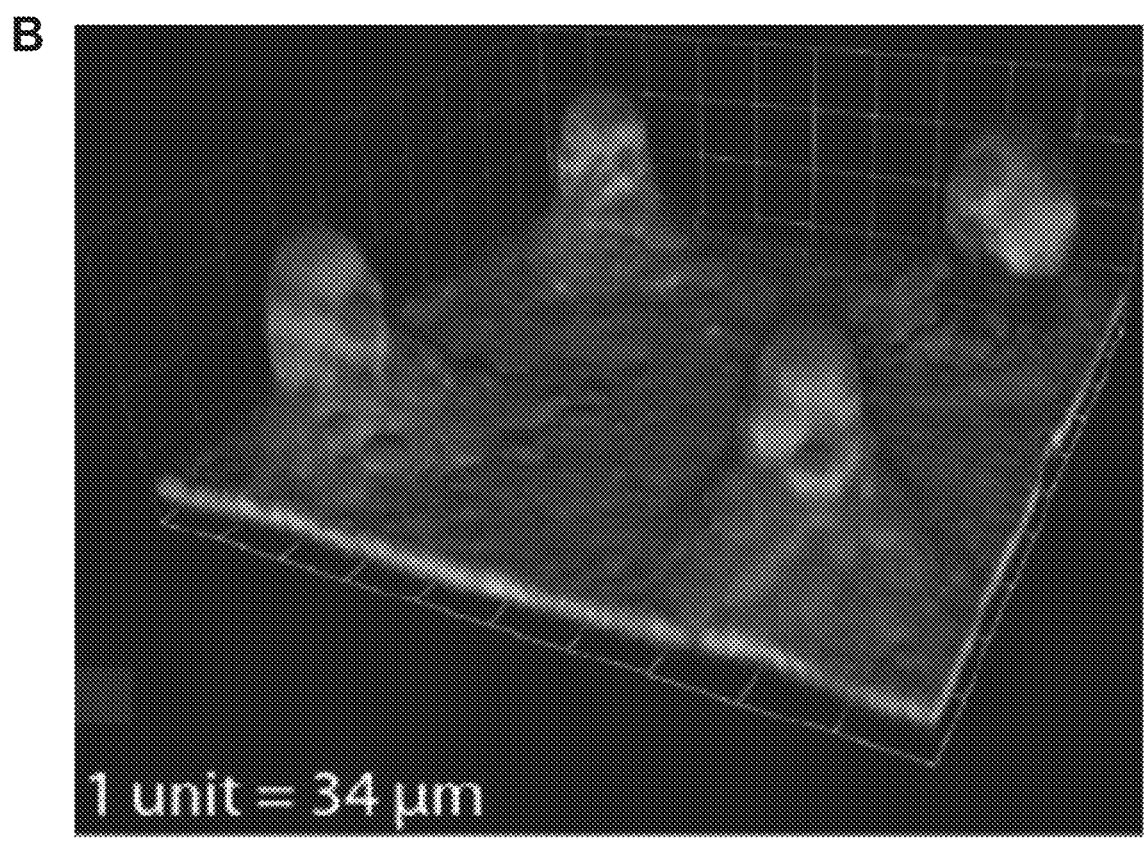
FIG. 14B shows that Caco-2 cells grown on SU-8 villi mimicked key aspects of the GI-tract epithelium.
Figure 23:
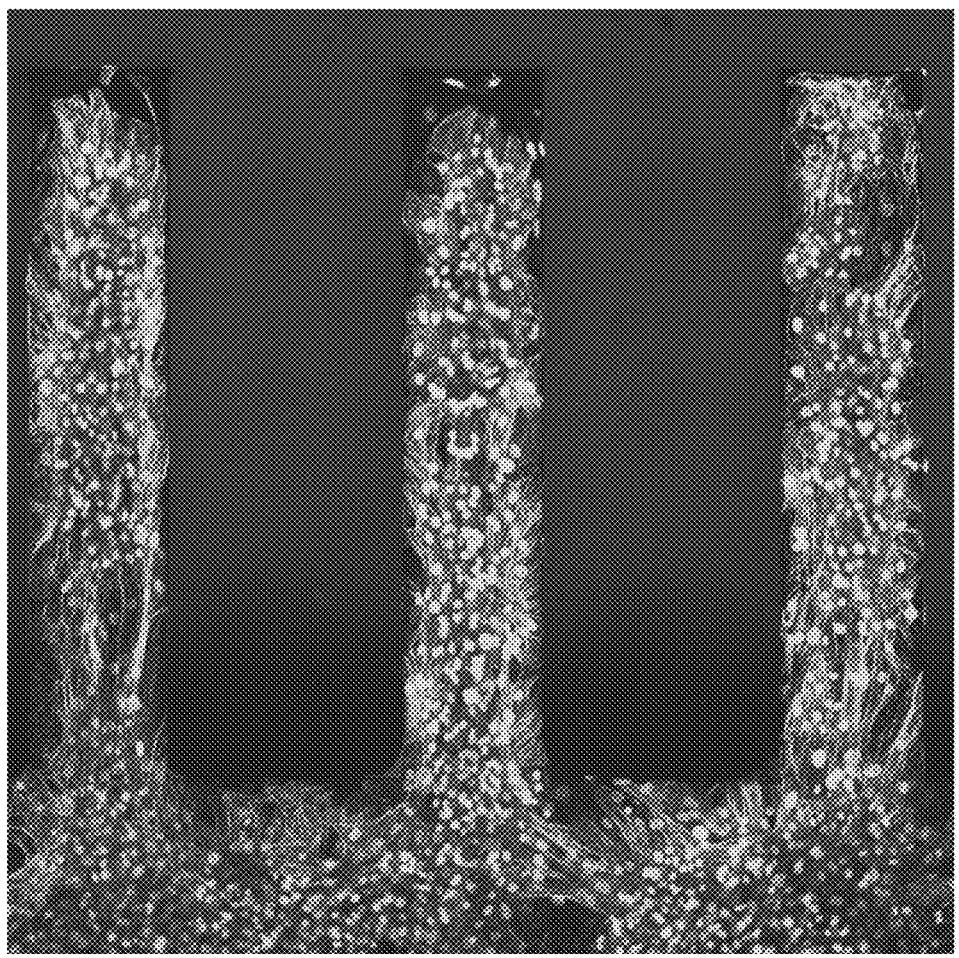
FIG. 23 shows an image of cardiomyocytes (derived from human iPSCs) cultured on cantilevers for 19 days and immunostained for troponin T.
Figure 24:
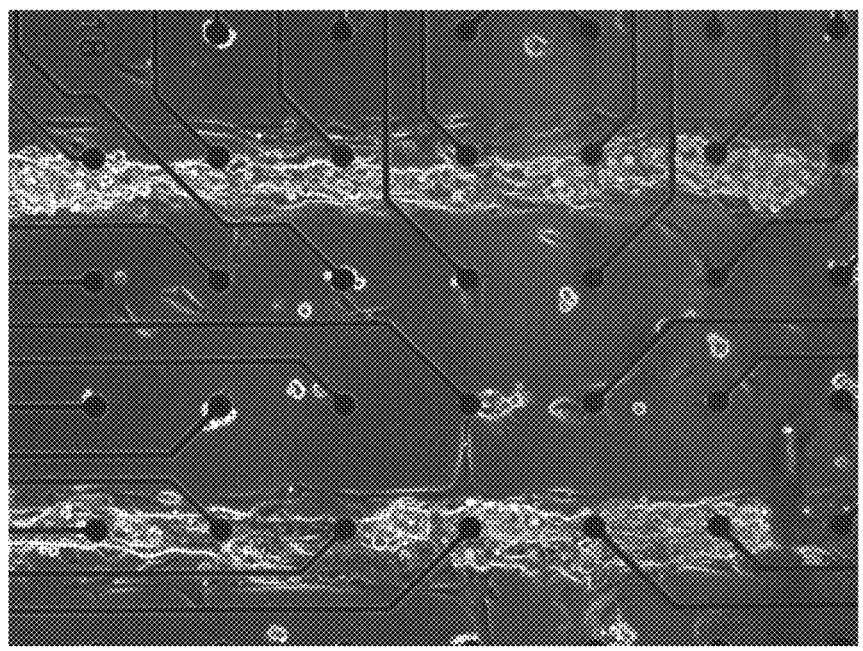
FIG. 24 shows a phase contrast micrograph of patterned cardiomyocytes 12 days in vitro (derived from human iPSCs) on top of substrate embedded extracellular electrodes.

Use of the pumpless cell culture platform for the nervous system is shown in FIG. 17 and use of the pumpless cell culture platform for the cardiac system is shown in FIG. 7.

iv) Experimental Advantages

An in vitro physiological system that represents cardiac function using a combination of chip based systems integrated with human stem cell derived cardiomyocytes was constructed and is described herein. A unique feature of the disclosed system is that the major determinants of human heart functions (e.g., rhythm generation, conduction, AP length, and force) were modeled by integrating 2-D cellular systems with silicon constructs. In other words, a potentially high-throughput 2-D cell culture-based integrated system that measures the major determinants of human cardiac function was generated. As electrical activity in the heart and cardiac muscle contraction are the primary focus of both pre-clinical toxicity and efficacy evaluation, the experiments provided herein deconstructed the heart into its primary functions and then reconstructed the data to predict drug effects in clinical trials.

To measure the relevant cardiac parameters, a platform was constructed using two devices: (1) extracellular surface-embedded microelectrodes for measuring the electrical properties of cardiac myocytes, and (2) AFM (Atomic Force Microscope) cantilevers for measuring the contractile force of the cardiac myocytes. The successful integration of cardiac myocytes into the force measurement platform described herein required several inventive steps including, but not limited to, the following: optimization of the serum-free medium for attachment and differentiation of human cardiac myocytes, adaptation and optimization of the surface-modification technique, adaptation of the force measurement and analysis system to cardiac myocytes, and validation of the system with selected reference compounds.

Thus, the disclosed system provides a novel, functional high-throughput human cardiac myocyte-based screen for cardiac force generation.

The advantages of the disclosed systems are numerous: (1) the systems can be constructed in large scalable quantities, (2) the cells are organized by self-assembly without intervention, (3) the cells can be organized in a multiple well format, (4) data recording can be automated, and (5) drug administration can be automated. Furthermore, the use of human cardiac myocytes in the disclosed system eliminated the extrapolation problems generated from interspecies differences. These advantages, and others, converge to generate a high-throughput screening system that can measure numerous cardiac parameters including spontaneous beating frequency and force and velocity-force relationships.

Concerning the predictive value of the disclosed system: the measured in vitro electrophysiological parameters are analogous to the parameters used in the SCREENIT scoring system introduced by Hondeghem and coworkers in 1994 based on a rabbit model. In the disclosed system, beating frequency, conduction velocity, QT interval and peak force, reverse use dependence, variability in QT intervals and relative refractory period (which is related to triangulation) were all measured, which the predictive value of the screen.

Each of the following patent applications is incorporated herein by reference in its entirety: (1) U.S. patent application Ser. No. 12/661,323 filed on Mar. 15, 2000 and titled "Bio-Microelectromechanical System Transducer and Associated Methods", (2) U.S. patent application Ser. No. 12/765,399 filed on Apr. 22, 2010 and titled "Method for Culturing Skeletal Muscle for Tissue Engineering", (3) U.S. patent application Ser. No. 12/938,701 filed Nov. 3, 2010 and titled "Patterned Cardiomyocyte Culture on Microelectrode Array", (4) U.S. patent application Ser. No. 13/102,672 filed on May 6, 2011 and titled "Formation of Neuromuscular Junctions in a Defined System", (5) U.S. patent application Ser. No. 12/145,810 filed Jun. 25, 2008 and titled "Cell Culture Media and Process for Differentiation of Human Spinal Cord Stem Cells into Functional Motor Neuron Cells", (6) U.S. patent application Ser. No. 13/576,442 filed Feb. 7, 2011 and titled "Model and Methods for Identifying Points of Action in Electrically Active Cells", (7) U.S. patent application Ser. No. 13/696,396 filed May 6, 2011 and titled "Formation of Neuromuscular Junctions", (8) U.S. patent application Ser. No. 12/117,339 filed May 8, 2008 and titled "Culture of Electrically Functional Adult Spinal Cord Neurons and Associated Methods", (9) U.S. patent application Ser. No. 12/788,732 filed May 27, 2010 and titled "Method of Myelinating Isolated Motoneurons", (10) U.S. patent application Ser. No. 12/765,996 filed Apr. 23, 2010 and titled "Long Term In Vitro Culture of Tissue Engineered Functional Neuromuscular Junctions" (11) U.S. patent application Ser. No. 13/322,903 filed on May 28, 2010 and titled "In Vitro Production of Oligodendrocytes from Human Umbilical Cord Stem Cells", (12) U.S. patent application Ser. No. 13/322,911 filed May 27, 2010 and titled "Method of Screening Drugs for Reversal of Amyloid Beta Neurotoxicity", (13) U.S. Provisional Patent Application No. 61/684,168 filed Aug. 17, 2012 and titled "Methods, Systems and Compositions for In Vitro Cellular Models of Mammalian Systems", (14) U.S. Provisional patent Application 61/758,628 filed Jan. 30, 2013 and titled "Compositions and Methods Comprising Cardiac Myocytes", (15) U.S. Provisional Patent Application No. 61/732,042 filed Nov. 30, 2012 and titled "Derivation of Sensory Neurons and Neural Crest Stem Cells from Human Neural Progenitor HNP1", (16) U.S. Provisional Patent Application No. 61/732,574 filed Dec. 3, 2012 and titled "Derivation of Sensory Neurons and Neural Crest Stem Cells from Human Neural Progenitor HNP1", (17) U.S. Provisional Patent Application Ser. No. 61/784,923 filed Mar. 14, 2013 titled "Compositions and Methods for Generating Neural Crest Cells", (18) U.S. Provisional Patent Application Ser. No. 61/78,9184, titled "Methods, Systems and Compositions for In Vitro Cellular Models of Mammalian Systems" filed Mar. 15, 2013, and (19) U.S. Provisional Patent Application Ser. No. 61/789,587, titled "Methods, Systems and Compositions for Concentric Cell Culture Analog Systems" filed Mar. 15, 2013, and applications concurrently filed herewith and each incorporated herein by reference in its entirety.

H. REFERENCES

Antzelevitch C. (2001) Transmural dispersion of repolarization and the T wave. Cardiovasc Res. 50: 426-431.

Antzelevitch C. (2005) Cardiac repolarization. The long and short of it. Europace. 7: 3-9.

Badie N, et al. (2009) A method to replicate the microstructure of heart tissue in vitro using DTMRI-based cell micropatterning. Ann Biomed Eng. 37: 2510-2521.

Belardinelli L, et al. (2003) Assessing predictors of drug-induced torsade de pointes. Trends Pharmacol Sci. 24: 619-625.

Bourgeois E B, et al. (2009) Change in conduction velocity due to fiber curvature in cultured neonatal rat ventricular myocytcs. IEEE Trans Biomed Eng. 56: 855-861.

Briggs M P, Practical Surface Analysis by Auger and X-ray Photoelectron Spectroscopy. New York, John Wiley and Sons (1992).

Campbell T J, et al. (2001) Therapeutic drug monitoring: antiarrhythmic drugs. Br J Clin Pharmacol. 52 Suppl 1: 21S-34S.

Carlsson L. (2006) In vitro and in vivo models for testing arrhythmogenesis in drugs. J Intern Med. 259: 70-80.

Choudhury A, et al. (2007) A piezoresistive microcantilever array for surface stress measurement: curvature model and fabrication. J Micromech Microeng. 17: 2065-2076.

Corey J M, et al. (1991) Compliance of hippocampal neurons to patterned substrate networks. J Neurosci Res. 30: 300-307.

Das M, et al. (2003) Electrophysiological and morphological characterization of rat embryonic motoneurons in a defined system. Biotechnol Prog. 19: 1756-1761.

Das M, et al. (2004) Long-term culture of embryonic rat cardiomyocytes on an organosilane surface in a serum-free medium. Biomaterials. 25: 5643-5647.

Das M, et al. (2005) Adult rat spinal cord culture on an organosilane surface in a novel serum-free medium. In Vitro Cell Dev Biol Anim. 41: 343-348.

Das M, et al. (2006) A defined system to allow skeletal muscle differentiation and subsequent integration with silicon microstructures. Biomaterials. 27: 4374-4380.

Das M, et al. (2007) Auto-catalytic ceria nanoparticles offer neuroprotection to adult rat spinal cord neurons. Biomaterials. 28: 1918-1925.

Das M, et al. (2007) Differentiation of skeletal muscle and integration of myotubes with silicon microstructures using serum-free medium and a synthetic silane substrate. Nat Protoc. 2: 1795-1801.

Das M, et al. (2007) Embryonic motoneuron-skeletal muscle co-culture in a defined system. Neuroscience. 146: 481-488.

Das M, et al. (2008) Temporal neurotransmitter conditioning restores the functional activity of adult spinal cord neurons in long-term culture. Exp Neurol. 209: 171-180.

Das M, et al. (2009) Developing a novel serum-free cell culture model of skeletal muscle differentiation by systematically studying the role of different growth factors in myotube formation. In Vitro Cell Dev Biol Anim. 45: 378-387.

Das M, et al. (2009) Skeletal Muscle Tissue Engineering: An Improved Model Promoting Long Term Survival of Myotubes, Structural Development of E-C Coupling Apparatus and Neonatal Myosin Heavy Chain (MHC) Expression. Biomaterials. 30: 5392-5402.

Das M, et al. (2010) A defined long-term in vitro tissue engineered model of neuromuscular junctions. Biomaterials. 31: 4880-4888.

Datar et al. MRS Bulletin. 34, 449 (2009).

De Clerck F, et al. (2002) In vivo measurement of QT prolongation, dispersion and arrhythmogenesis: application to the preclinical cardiovascular safety pharmacology of a new chemical entity. Fundam Clin Pharmacol. 16: 125-140.

Dhir V, et al. (2009) Patterning of diverse mammalian cell types in serum free medium with photoablation. Biotechnol Prog. 25: 594-603.

Edwards D, et al. (2010) Addition of glutamate to serum-free culture promotes recovery of electrical activity in adult hippocampal neurons in vitro. J Neurosci Methods. 190: 155-163

Guo X, et al. (2011) Neuromuscular junction formation between human stem cell-derived motoneurons and human skeletal muscle in a defined system. Biomaterials. 32: 9602-9611.

Guo X F, et al. (2010) Neuromuscular junction formation between human stem-cell-derived motoneurons and rat skeletal muscle in a defined system. Tissue Eng Part C Methods. 16: 1347-1355.

Hondeghem L M and Hoffman P. (2003) Blinded test in isolated female rabbit heart reliably identifies action potential duration prolongation and proarrhythmic drugs: importance of triangulation, reverse use dependence, and instability. J Cardiovasc Pharmacol. 41: 14-24.

Hondeghem L M, et al. (2001) Instability and triangulation of the action potential predict serious proarrhythmia, but action potential duration prolongation is antiarrhythmic. Circulation. 103: 2004-2013.

Hondeghem L M, et al. (2003) Detection of proarrhythmia in the female rabbit heart: blinded validation. J Cardiovasc Electrophysiol. 14: 287-294.

Hondeghem L M. (2006) Thorough QT/QTc not so thorough: removes torsadogenic predictors from the T-wave, incriminates safe drugs, and misses profibrillatory drugs. J Cardiovasc Electrophysiol. 17: 337-340.

Hondeghem L M. (2007) Relative contributions of TRIaD and QT to proarrhythmia. J Cardiovasc Electrophysiol. 18: 655-657. Jackson J H 4th, et al. (2004) Assessment of drug therapy management and the prevalence of heart failure in a managed care population with hypertension. J Manag Care Pharm. 10: 513-520.

King T, et al. (2000) Piezoactuators for 'real-world' applications—Can they deliver sufficient displacement? Power Engineering. 14: 105-110."\.

Lawrence C L, et al. (2005) Nonclinical proarrhythmia models: predicting Torsades de Pointes. J Pharmacol Toxicol Methods. 52: 46-59.

Lawrence C L, et al. (2006) A rabbit Langendorff heart proarrhythmia model: predictive value for clinical identification of Torsades de Pointes. Br J Pharmacol. 149: 845-860.

Lin J W, et al. (2008) Region [corrected] of slowed conduction acts as core for spiral wave reentry in cardiac cell monolayers. Am J Physiol Heart Circ Physiol. 294: H58-H65.

Liu T X, et al. (2006) Blinded validation of the isolated arterially perfused rabbit ventricular wedge in preclinical assessment of drug-induced proarrhythmias. Heart Rhythm. 3: 948-956.

Lochter A J, et al. (1995) Control of neuronal morphology in vitro: interplay between adhesive substrate forces and molecular instruction. J Neurosci Res. 42: 145-158.

Lou X J. (2009) Polarization fatigue in ferroelectric thin films and related materials. Journal of Applied Physics. 105: 024101-024124.

Moe G K. (1962) On the multiple wavelet hypothesis of atrial fibrillation. Arch Int Pharmacodyn Ther. 183-188.

Molnar P, et al. (2007) Photolithographic Patterning of C2C12 Myotubes using Vitronectin as Growth Substrate in Serum-Free Medium. Biotechnol Prog. 23: 265-268.

Mutyala M S K, et al. (2009) Mechanical and electronic approaches to improve the sensitivity of microcantilever sensors. Acta Mechanica Sinica. 25: 1-12.

Nash M P, et al. (2006) Evidence for multiple mechanisms in human ventricular fibrillation. Circulation. 114: 536-542.

Natarajan A, et al. (2006) Microelectrode array recordings of cardiac action potentials as a high throughput method to evaluate pesticide toxicity. Toxicol In Vitro. 20: 375-381.

Natarajan A, et al. (2008) Growth and electrophysiological properties of rat embryonic cardiomyocytes on hydroxyl- and carboxyl-modified surfaces. J Biomater Sci Polym Ed. 19: 1319-1331.

Natarajan A, et al. (2011) Patterned cardiomyocytes on microelectrode arrays as a functional, high information content drug screening platform. Biomaterials. 32: 4267-4274.

Nguemo F, et al. (2012) In vitro model for assessing arrhythmogenic properties of drugs based on high-resolution impedance measurements. Cell Physiol Biochem. 29: 819-832.

Parker K K, et al. (2008) Myofibrillar architecture in engineered cardiac myocytes. Circ Res. 103: 340-342.

Peng H B, et al. (2003) Differential effects of neurotrophins and schwann cell-derived signals on neuronal survival/growth and synaptogenesis. J Neurosci. 23: 5050-5060.

Pijnappels D A, et al. (2007) Resynchronization of separated rat cardiomyocyte fields with genetically modified human ventricular scar fibroblasts. Circulation. 116: 2018-2028.

Popat K C, et al. (2004) Surface modification of nanoporous alumina surfaces with poly(ethylene glycol). Langmuir. 20: 8035-8041.

Popat K C, et al. (2004) Quantitative xps analysis of peg-modified silicon surfaces. J Phys Chem. 108: 5185-5188. Ravenscroft M S, et al. J Am Chem Soc. 120, 12169 (1998)

Recanatini M, et al. (2005) QT prolongation through hERG K(+) channel blockade: current knowledge and strategies for the early prediction during drug development. Med Res Rev. 25: 133-166.

Rumsey J W, et al. (2008) Tissue Engineering Intrafusal Fibers: Dose and Time Dependent Differentiation of Nuclear Bag Fibers in a Defined In Vitro System using Neuregulin 1- beta-1. Biomaterials. 29: 994-1004.

Rumsey J W, et al. (2009) Node of Ranvier formation on motoneurons in vitro. Biomaterials. 30: 3567-3572.

Rumsey J W, et al. (2010) Tissue engineering the mechanosensory circuit of the stretch reflex are: sensory neuron innervation of intrafusal muscle fibers. Biomaterials. 31: 8218-8227. Sala M, et al. Ther Adv Cardiovasc Dis. 3, 29 (2009).

Sathaye A, et al. (2006) Electrical pacing counteracts intrinsic shortening of action potential duration of neonatal rat ventricular cells in culture. J Mol Cell Cardiol. 41: 633-641.

Suter W. (2006) Predictive value of in vitro safety studies. Curr Opin Chem Biol. 10: 362-366.

Valentin J P, et al. (2004) Review of the predictive value of the Langendorff heart model (Screenit system) in assessing the proarrhythmic potential of drugs. J Pharmacol Toxicol Methods. 49: 171-181.

Varghese K, et al. (2009) Regeneration and characterization of adult mouse hippocampal neurons in a defined in vitro system. J Neurosci Methods. 177: 51-59.

Varghese K, et al. (2010) A new target for amyloid beta toxicity validated by standard and high-throughput electrophysiology. PLoS One. 5: e8643.

Wilson K, et al. (2010) Measurement of contractile stress generated by cultured rat muscle on silicon cantilevers for toxin detection and muscle performance enhancement. PLoS One. 5: e11042.

What is claimed is:

1. A method of determining one or more parameters of a cardiac cell culture, the method comprising:
   detecting an electrical property from a monolayer of cardiac myocytes extending over a microelectrode array and a plurality of cantilevers, the electrical property detected using the microelectrode array;
   receiving a reading of the electrical property from the microelectrode array at a computing device;
   detecting a contractile property from the monolayer of cardiac myocytes using a piezoresistive or piezoelectric property of the plurality of cantilevers;
   receiving a reading of the contractile property from the plurality of cantilevers at the computing device;
   determining multiple cardiac parameters based on both the electrical property reading and the contractile property reading;
   contacting the monolayer of cardiac monocytes with an agent in a mixed medium;
   detecting both electrical properties and contractile properties of the monolayer in response to the agent;
   receiving readings of both electrical properties and contractile properties of the monolayer in response to the agent;
   measuring changes in conduction velocity and peak contractile force in response to the agent; and
   creating a fingerprint for the agent based on at least the changes in conduction velocity and peak contractile force.

2. The method of claim 1, wherein the agent is a metabolic inhibitor, a nutritional supplement, a therapeutic compound, composition, and drug, an investigational compound, composition, and drug, a biosimilar, an agonist, an antagonist, a hormone, a growth factor, a small molecule, a monoclonal antibody, and combinations thereof.

3. The method of claim 1, further comprising predicting cardiac side effects of the agent based on the one or more of the multiple cardiac parameters.

4. The method of claim 1, further comprising electrically stimulating the monolayer prior to detecting electrical properties and contractile properties.

5. The method of claim 1, wherein at least one cardiac parameter of the multiple cardiac parameters is spontaneous beating rate.

6. The method of claim 1, wherein at least one cardiac parameter of the multiple cardiac parameters is conduction velocity.

7. The method of claim 1, wherein at least one cardiac parameter of the multiple cardiac parameters is QT interval.

8. The method of claim 1, wherein at least one cardiac parameter of the multiple cardiac parameters is minimal interspike interval.

9. The method of claim 1, wherein at least one cardiac parameter of the multiple cardiac parameters is peak contractile force.

10. The method of claim 1, wherein at least one cardiac parameter of the multiple cardiac parameters is speed of contraction.

11. The method of claim 1, wherein at least one cardiac parameter of the multiple cardiac parameters is time to relaxation.

12. The method of claim 1, wherein at least one cardiac parameter of the multiple cardiac parameters is an arrhythmogenic mechanism.

13. The method of claim 12, wherein the arrhythmogenic mechanism is rhythm generation, and the method further comprises evaluating rhythm generation by measuring at least one of chronotropy and firing frequency dispersion from the monolayer.

14. The method of claim 12, wherein the arrhythmogenic mechanism is conduction, and the method further comprises evaluating conduction by measuring at least one of conduction velocity, conduction velocity dispersion, and frequency dependence of conduction velocity from the monolayer.

15. The method of claim 12, wherein the arrhythmogenic mechanism is reentry, and the method further comprises evaluating reentry by measuring at least one of QT interval, QT interval dispersion, reverse use dependence, absolute refractory period, and relative refractory period from the monolayer.

16. The method of claim 1, further comprising maintaining an environmental temperature of 37 degrees Celsius around the monolayer using a temperature controller.

17. The method of claim 1, further comprising contacting the monolayer with a mixed medium.

* * * * *